US012478682B2

(12) United States Patent
Bhat et al.

(10) Patent No.: US 12,478,682 B2
(45) Date of Patent: Nov. 25, 2025

(54) NUCLEIC ACID CONJUGATES AND USES THEREOF

(71) Applicant: Translate Bio MA, Inc., Lexington, MA (US)

(72) Inventors: Balkrishen Bhat, Carlsbad, CA (US); Saswata Karmakar, Acton, MA (US); Debatosh Majumdar, Lexington, MA (US); Jia Tay, Acton, MA (US); Nelson Chau, Needham, MA (US)

(73) Assignee: Translate Bio MA, Inc., Lexington, MA (US)

( * ) Notice: Subject to any disclaimer, the term of this patent is extended or adjusted under 35 U.S.C. 154(b) by 311 days.

(21) Appl. No.: 17/552,750

(22) Filed: Dec. 16, 2021

(65) Prior Publication Data

US 2022/0218829 A1 Jul. 14, 2022

Related U.S. Application Data

(63) Continuation of application No. 16/317,229, filed as application No. PCT/US2017/041469 on Jul. 11, 2017, now Pat. No. 11,253,601.

(60) Provisional application No. 62/478,499, filed on Mar. 29, 2017, provisional application No. 62/360,518, filed on Jul. 11, 2016.

(51) Int. Cl.

| | |
|---|---|
| ***A61K 47/54*** | (2017.01) |
| ***A61K 31/7088*** | (2006.01) |
| ***A61K 47/60*** | (2017.01) |
| ***C12N 15/113*** | (2010.01) |
| ***C12N 15/87*** | (2006.01) |

(52) U.S. Cl.

CPC ........ *A61K 47/549* (2017.08); *A61K 31/7088* (2013.01); *A61K 47/60* (2017.08); *C12N 15/113* (2013.01); *C12N 15/87* (2013.01); *C12N 2310/315* (2013.01); *C12N 2310/351* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohtsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |

(Continued)

FOREIGN PATENT DOCUMENTS

| | | | |
|---|---|---|---|
| WO | WO 1999/67378 | A1 | 12/1999 |
| WO | WO 2005/042777 | A2 | 5/2005 |

(Continued)

OTHER PUBLICATIONS

Extended European Search Report for Application No. EP 17828273.7, mailed Feb. 28, 2020.

(Continued)

*Primary Examiner* — Patrick T Lewis

(74) *Attorney, Agent, or Firm* — Wolf, Greenfield & Sacks, P.C.

(57) ABSTRACT

Provided herein are conjugates comprising targeting moieties such as sugars, folates and cell-penetrating peptides, which can be used for the improved delivery of agents (e.g., nucleic acids, such as oligonucleotides or mRNAs, or other agents) to cells. The invention provides conjugates and compounds comprising targeting moieties, methods for preparing the same, and intermediates useful in their preparation. In another aspect, the present invention provides formulations (e.g., pharmaceutical compositions) comprising the targeting moiety-containing conjugates and compounds. The present invention also provides methods for delivering agents (e.g., nucleic acids such as oligonucleotides or mRNAs) to a cell, methods for treating and/or preventing a disease or condition in a subject, and methods for modulating gene expression in a cell or a subject. Further, provided herein are kits comprising the conjugates, or formulations thereof; and kits for the preparation of conjugates described herein.

18 Claims, 8 Drawing Sheets

Specification includes a Sequence Listing.

(56) References Cited

U.S. PATENT DOCUMENTS

| | | | |
|---|---|---|---|
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,256,775 | A | 10/1993 | Froehler |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,321,131 | A | 6/1994 | Agrawal et al. |
| 5,366,878 | A | 11/1994 | Pederson et al. |
| 5,367,066 | A | 11/1994 | Urdea et al. |
| 5,371,241 | A | 12/1994 | Brush |
| 5,391,723 | A | 2/1995 | Priest |
| 5,399,676 | A | 3/1995 | Froehler |
| 5,403,711 | A | 4/1995 | Walder et al. |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,491,133 | A | 2/1996 | Walder et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,552 | A | 10/1996 | Magda et al. |
| 5,567,810 | A | 10/1996 | Weis et al. |
| 5,571,799 | A | 11/1996 | Tkachuk et al. |
| 5,574,142 | A | 11/1996 | Meyer, Jr. et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,652,355 | A | 7/1997 | Metelev et al. |
| 5,652,356 | A | 7/1997 | Agrawal |
| 5,663,312 | A | 9/1997 | Chaturvedula |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,922 | A | 12/1997 | Cook |
| 5,750,692 | A | 5/1998 | Cook et al. |
| 6,287,860 | B1 | 9/2001 | Monia et al. |
| 7,314,923 | B2 | 1/2008 | Kaneko et al. |
| 7,335,765 | B2 | 2/2008 | Kaneko et al. |
| 7,399,845 | B2 | 7/2008 | Seth et al. |
| 7,569,686 | B1 | 8/2009 | Bhat et al. |
| 7,741,457 | B2 | 6/2010 | Seth et al. |
| 7,816,333 | B2 | 10/2010 | Kaneko et al. |
| 7,951,926 | B2 | 5/2011 | Morvan et al. |
| 8,022,193 | B2 | 9/2011 | Seth et al. |
| 8,828,956 | B2 | 9/2014 | Manoharan et al. |
| 8,962,580 | B2 | 2/2015 | Manoharan et al. |
| 9,061,021 | B2 | 6/2015 | Guild et al. |
| 9,181,549 | B2 | 11/2015 | Prakash et al. |
| 9,198,972 | B2 | 12/2015 | Manoharan et al. |
| 11,253,601 | B2 | 2/2022 | Bhat et al. |
| 2007/0068265 | A1 | 3/2007 | Watanabe |
| 2011/0009471 | A1 | 1/2011 | Kaneko et al. |
| 2012/0071540 | A1 | 3/2012 | Lu et al. |
| 2012/0136042 | A1 | 5/2012 | Manoharan et al. |
| 2015/0184195 | A1 | 7/2015 | Thess et al. |
| 2015/0218554 | A1 | 8/2015 | Thess |
| 2015/0299695 | A1 | 10/2015 | Uhlmann et al. |
| 2015/0320847 | A1 | 11/2015 | Thess et al. |
| 2016/0058842 | A1 | 3/2016 | Turecek et al. |
| 2017/0009244 | A1 | 1/2017 | Sahin et al. |
| 2017/0029847 | A1 | 2/2017 | Thess |
| 2017/0056528 | A1 | 3/2017 | De Fougerolles et al. |
| 2017/0252461 | A1 | 9/2017 | Chakraborty et al. |
| 2017/0349896 | A1 | 12/2017 | Albaek et al. |
| 2018/0055869 | A1 | 3/2018 | Ozsolak |
| 2019/0224326 | A1 | 7/2019 | Bhat et al. |
| 2021/0052706 | A1 | 2/2021 | Bhat et al. |

FOREIGN PATENT DOCUMENTS

| | | | |
|---|---|---|---|
| WO | WO 2007/112753 | A2 | 10/2007 |
| WO | WO 2007/112754 | A2 | 10/2007 |
| WO | WO 2009/043353 | A2 | 4/2009 |
| WO | WO 2011/012316 | A2 | 2/2011 |
| WO | WO 2013/166121 | A1 | 11/2013 |
| WO | WO 2014/172698 | A1 | 10/2014 |
| WO | WO 2014/179620 | A1 | 11/2014 |
| WO | WO 2015/006740 | A2 | 1/2015 |
| WO | WO 2016/091391 | A1 | 6/2016 |
| WO | WO 2016/107877 | A1 | 7/2016 |
| WO | WO 2016/130943 | A1 | 8/2016 |
| WO | WO 2016/205410 | A2 | 12/2016 |
| WO | WO 2017/001554 | A1 | 1/2017 |
| WO | WO 2017/059902 | A1 | 4/2017 |
| WO | WO 2017/075038 | A1 | 5/2017 |

(56) References Cited

FOREIGN PATENT DOCUMENTS

WO WO 2017/153936 A1 9/2017
WO WO 2017/167910 A1 10/2017

OTHER PUBLICATIONS

International Search Report and Written Opinion for International Application No. PCT/US2017/041469, mailed Dec. 12, 2017.
International Preliminary Report on Patentability for International Application No. PCT/US2017/041469, mailed Jan. 24, 2019.
International Search Report and Written Opinion for International Application No. PCT/US2019/013070, mailed May 1, 2019.
International Preliminary Report on Patentability for International Application No. PCT/US2019/013070, mailed Jul. 23, 2020.
Extended European Search Report for Application No. EP 19738098.3, mailed Sep. 23, 2021.
Bejjani et al., N-tritylprolinal: an efficient building block for the stereoselective synthesis of proline-derived amino alcohols. J Org Chem. 2003;68(25):9747-9752. doi:10.1021/jo034976g.
Braasch et al., Novel antisense and peptide nucleic acid strategies for controlling gene expression. Biochemistry. 2002;41(14):4503-4510. doi:10.1021/bi0122112.
Brown et al., Conjugation of an oligonucleotide to Tat, a cell-penetrating peptide, via click chemistry. Tetrahedron Letters. Sep. 22, 2010:51(38): 5032-5034.
Crooke et al., Pharmacokinetic properties of several novel oligonucleotide analogs in mice. J Pharmacol Exp Ther. 1996;277(2):923-937.
De Mesmaeker et al., Antisense Oligonucleotides. Acc. Chem. Res. 1995;28:366-74.
Dohmen et al., Defined Folate-PEG-siRNA Conjugates for Receptor-specific Gene Silencing. Mol Ther Nucleic Acids. Jan. 2012; 1(1): e7. EPub Jan. 31, 2012. doi: 10.1038/mtna.2011.10. 6 pages.
Efthymiou et al., Chemical architecture and applications of nucleic acid derivatives containing 1,2,3-triazole functionalities synthesized via click chemistry. Molecules. Oct. 26, 2012;17(11):12665-703. doi: 10.3390/molecules171112665.
Englishsch et al.,Angewandle Chemie, International Edition, 1991, 30, p. 613.
Gabeyehu et al., Novel biotinylated nucleotide—analogs for labeling and colorimetric detection of DNA. Nucleic Acids Res. 1987;15(11):4513-4534. doi:10.1093/nar/15.11.4513.
Gooding et al., Oligonucleotide conjugates—Candidates for gene silencing therapeutics. Eur J Pharm Biopharm. Oct. 2016;107:321-40. doi: 10.1016/j.ejpb.2016.07.024. Epub Aug. 10, 2016.
He et al., Conjugation and Evaluation of Triazole-Linked Single Guide RNA for CRISPR-Cas9 Gene Editing. Chem biochem. Oct. 4, 2016;17(19):1809-1812. doi: 10.1002/cbic.201600320. Epub Aug. 19, 2016.
Heasman, Morpholino oligos: making sense of antisense?. Dev Biol. 2002;243(2):209-214. doi:10.1006/dbio.2001.0565.
Horie et al., Synthesis and properties of ENA oligonucleotides targeted to human telomerase RNA subunit. Nucleic Acids Symp Ser (Oxf). 2005;(49):171-172. doi:10.1093/nass/49.1.171.
Huang, Preclinical and Clinical Advances of GalNAc-Decorated Nucleic Acid Therapeutics. Mol Ther Nucleic Acids. Mar. 17, 2017;6:116-132. doi: 10.1016/j.omtn.2016.12.003. Epub Dec. 10, 2016.
Iversen, Phosphorodiamidate morpholino oligomers: favorable properties for sequence-specific gene inactivation. Curr Opin Mol Ther. 2001;3(3):235-238.
Jayaprakash et al., Non-nucleoside building blocks for copper-assisted and copper-free click chemistry for the efficient synthesis of RNA conjugates. Org Lett. Dec. 3, 2010;12(23):5410-3. doi: 10.1021/ol102205j. Epub Nov. 4, 2010.
Kabanov et al., A new class of antivirals: antisense oligonucleotides combined with a hydrophobic substituent effectively inhibit influenza virus reproduction and synthesis of virus-specific proteins in MDCK cells. FEBS Lett. 1990;259(2):327-330. doi:10.1016/0014-5793(90)80039-1.
Kasuya et al., In vivo delivery of bionanocapsules displaying Phaseolus vulgaris agglutinin-L4 isolectin to malignant tumors overexpressing N-acetylglucosaminyltransferase V. Hum Gene Ther. 2008;19(9):887-895. doi:10.1089/hum.2008.037.
Khorev et al., Trivalent, Gal/GalNAc-containing ligands designed for the asialoglycoprotein receptor. Bioorg Med Chem. 2008;16(9):5216-5231. doi:10.1016/j.bmc.2008.03.017.
Kikkeri et al., Facile synthesis of size dependent Ru(II)-carbohydrate dendrimers via click chemistry. Chem Commun (Camb). 2010;46(13):2197-2199. doi:10.1039/b925113h.
Koizumi et al., ENA oligonucleotides as therapeutics. Curr Opin Mol Ther. 2006;8(2):144-149.
Kornberg., “DNA Replication,” W. H. Freeman & Co., San Francisco, 1980, pp. 75-77.
Kroschwitz, The Concise Encyclopedia of Polymer Science And Engineering, pp. 858-859, Kroschwitz, ed. John Wiley & Sons, 199.
Lacerra et al., Restoration of hemoglobin A synthesis in erythroid cells from peripheral blood of thalassemic patients. Proc Natl Acad Sci U S A. 2000;97(17):9591-9596. doi:10.1073/pnas.97.17.9591.
Letsinger et al., Cholesteryl-conjugated oligonucleotides: synthesis, properties, and activity as inhibitors of replication of human immunodeficiency virus in cell culture. Proc Natl Acad Sci U S A. 1989;86(17):6553-6556. doi:10.1073/pnas.86.17.6553.
Lok et al., Potent gene-specific inhibitory properties of mixed-backbone antisense oligonucleotides comprised of 2'-deoxy-2'-fluoro-D-arabinose and 2'-deoxyribose nucleotides. Biochemistry. 2002;41(10):3457-3467. doi:10.1021/bi0115075.
Manoharan et al. Cholic acid-oligonucleotide conjugates for antisense applications. Bioorg. Med. Chem. Let. Apr. 21, 1994;4(8):1053-1060.
Manoharan et al. Introduction of a lipophilic thioether tether in the minor groove of nucleic acids for antisense applications. Bioorg. Med. Chem. Lett. 1993;3(12):2765-2770.
Manoharan et al. Oligonucleotide Conjugates: Alteration of the Pharmacokinetic Properties of Antisense Agents. Nucleosides & Nucleotides, 1995;14(3-5):969-973.
Manoharan et al., Chemical modifications to improve uptake and bioavailability of antisense oligonucleotides. Ann N Y Acad Sci. 1992;660:306-309. doi:10.1111/j.1749-6632.1992.tb21095.x.
Manoharan et al., Lipidic nucleic acids. Tetrahedron Lett. May 22, 1995:36(21):3651-3654.
Matsuda et al., siRNA conjugates carrying sequentially assembled trivalent N-acetylgalactosamine linked through nucleosides elicit robust gene silencing in vivo in hepatocytes. ACS Chem Biol. May 15, 2015;10(5):1181-7. doi: 10.1021/cb501028c.
Min et al., Oligonucleotides comprised of alternating 2'-deoxy-2'-fluoro-beta-D-arabinonucleosides and D-2'-deoxyribonucleosides (2'F-ANA/DNA ‘altimers’) induce efficient RNA cleavage mediated by RNase H. Bioorg Med Chem Lett. 2002;12(18):2651-2654. doi:10.1016/s0960-894x(02)00439-0.
Mishra et al., Improved leishmanicidal effect of phosphorotioate antisense oligonucleotides by LDL-mediated delivery. Biochim Biophys Acta. 1995;1264(2):229-237. doi:10.1016/0167-4781(95)00145-7.
Morcos, Achieving efficient delivery of morpholino oligos in cultured cells. Genesis. 2001;30(3):94-102. doi:10.1002/gene.1039.
Morita et al., 2'-O,4'-C-ethylene-bridged nucleic acids (ENA) with nuclease-resistance and high affinity for RNA. Nucleic Acids Res Suppl. 2001;(1):241-242. doi:10.1093/nass/1.1.241.
Nair et al., Multivalent N-acetylgalactosamine-conjugated siRNA localizes in hepatocytes and elicits robust RNAi-mediated gene silencing. J Am Chem Soc. Dec. 10, 2014;136(49):16958-61. doi:10.1021/ja505986a. Epub Dec. 1, 2014.
Nasevisicius et al., Effective targeted gene ‘knockdown’ in zebrafish. Nat Genet. 2000;26(2):216-220. doi:10.1038/79951.
Nielsen et al., Sequence-selective recognition of DNA by strand displacement with a thymine-substituted polyamide. Science. 1991;254(5037):1497-1500. doi:10.1126/science.1962210.
Oberhauser et al., Effective incorporation of 2'-O-methyl-oligoribonucleotides into liposomes and enhanced cell association

(56) References Cited

OTHER PUBLICATIONS through modification with thiocholesterol. Nucleic Acids Res. 1992;20(3):533-538. doi:10.1093/nar/20.3.533.
Pourceau et al., Synthesis of mannose and galactose oligonucleotide conjugates by bi-click chemistry. J Org Chem. 2009;74(3):1218-1222. doi:10.1021/jo802536q.
Sanghvi, Chapter 15, Antisense Research and Applications, pp. 289-302, Crooke, and Lebleu, eds., CRC Press, 1993. Certain.
Shea et al., Synthesis, hybridization properties and antiviral activity of lipid-oligodeoxynucleotide conjugates. Nucleic Acids Res. 1990;18(13):3777-3783. doi:10.1093/nar/18.13.3777.
Sliedregt et al., Design and synthesis of novel amphiphilic dendritic galactosides for selective targeting of liposomes to the hepatic asialoglycoprotein receptor. J Med Chem. 1999;42(4):609-618. doi:10.1021/jm981078h.
Surono et al., Chimeric RNA/ethylene-bridged nucleic acids promote dystrophin expression in myocytes of duchenne muscular dystrophy by inducing skipping of the nonsense mutation-encoding exon. Hum Gene Ther. 2004;15(8):749-757. doi:10.1089/1043034041648444.
Svinarchuk et al., Inhibition of HIV proliferation in MT-4 cells by antisense oligonucleotide conjugated to lipophilic groups. Biochimie. 1993;75(1-2):49-54. doi:10.1016/0300-9084(93)90024-m.
Wang et al., Cyclohexene Nucleic Acids (CeNA): Serum Stable Oligonucleotides that Activate RNase H and Increase Duplex Stability with Complementary RNA. J Am. Chem. Soc. 2000, 122, 8595-8602.
Wang et al., In vitro evaluation of novel antisense oligonucleotides is predictive of in vivo exon skipping activity for Duchenne muscular dystrophy. J Gene Med. 2010;12(4):354-364. doi:10.1002/jgm.1446.
Winkler et al., Oligonucleotide conjugates for therapeutic applications. Ther Deliv. 2013;4(7):791-809. doi:10.4155/tde.13.47.
Wu et al., Improving the antigenicity of sTn antigen by modification of its sialic acid residue for development of glycoconjugate cancer vaccines. Bioconjug Chem. 2006;17(6):1537-1544. doi:10.1021/bc060103s.
Yamada et al., Versatile Site-Specific Conjugation of Small Molecules to siRNA Using Click Chemistry. J. Org. Chem. 2011:76(5); 1198-1211.

Excellent enhancement in target X mRNA upregulation
in primary hepatocytes with GalNAc conjugated oligo

• RN-02999: 5′-C* C A* T T G* T* C A C* A C* T C* C*

*expected cleavage*

• RN-10485: 5′-(GalNAc3)(PS)-$A_OA_O$-C* C A* T T G* T* C A C* A C* T C* C*

*expected cleavage (selective and faster)*

• RN-11028: 5′-(GalNAc3)(PS)-$A_{Rp}A_{Rp}$-C* C A* T T G* T* C A C* A C* T C* C*

*relatively slower cleavage (expected)*

• RN-11029: 5′-(GalNAc3)(PS)-$A_{Sp}A_{Sp}$-C* C A* T T G* T* C A C* A C* T C* C*

Figure 8

SEQUENCE LISTING

```
<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Lys Phe Phe Lys Phe Phe Lys Phe Phe Lys
1               5                   10


<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Arg Gln Ile Lys Ile Trp Phe Gln Asn Arg Arg Met Lys Trp Lys Lys
1               5                   10                  15


<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Gly Arg Lys Lys Lys Arg Arg Gln Arg Arg Arg Tyr Lys
1               5                   10


<210> SEQ ID NO 4
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
```

-continued

<221> NAME/KEY: misc_feature
<222> LOCATION: (13)..(13)
<223> OTHER INFORMATION: Xaa can be any naturally occurring amino acid

<400> SEQUENCE: 4

Arg Xaa Arg Arg Xaa Arg Arg Xaa Arg Arg Xaa Arg Xaa Asx
1 5 10

<210> SEQ ID NO 5
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 5

Arg Phe Arg Arg Phe Arg Arg Phe Arg Arg Phe Arg Xaa Asx
1 5 10

<210> SEQ ID NO 6
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 6
cgatcattca aa 12

<210> SEQ ID NO 7
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: locked nucleic acid; 5-methyl; phosphorothioate
<220> FEATURE:
<221> NAME/KEY: misc_feature
<222> LOCATION: (2)..(2)
<223> OTHER INFORMATION: phosphorothioate
<220> FEATURE:
<221> NAME/KEY: misc_feature
<222> LOCATION: (3)..(3)
<223> OTHER INFORMATION: locked nucleic acid; phosphorothioate
<220> FEATURE:
<221> NAME/KEY: misc_feature
<222> LOCATION: (4)..(5)
<223> OTHER INFORMATION: phosphorothioate
<220> FEATURE:
<221> NAME/KEY: misc_feature
<222> LOCATION: (6)..(7)
<223> OTHER INFORMATION: locked nucleic acid; phosphorothioate
<220> FEATURE:
<221> NAME/KEY: misc_feature
<222> LOCATION: (8)..(9)
<223> OTHER INFORMATION: phosphorothioate
<220> FEATURE:
<221> NAME/KEY: misc_feature
<222> LOCATION: (10)..(10)
<223> OTHER INFORMATION: locked nucleic acid; 5-methyl; phosphorothioate
<220> FEATURE:
<221> NAME/KEY: misc_feature
<222> LOCATION: (11)..(11)
<223> OTHER INFORMATION: phosphorothioate
<220> FEATURE:
<221> NAME/KEY: misc_feature
<222> LOCATION: (12)..(12)
<223> OTHER INFORMATION: locked nucleic acid; 5-methyl; phosphorothioate
<220> FEATURE:
<221> NAME/KEY: misc_feature
<222> LOCATION: (13)..(13)
<223> OTHER INFORMATION: phosphorothioate
<220> FEATURE:
<221> NAME/KEY: misc_feature
<222> LOCATION: (14)..(15)
<223> OTHER INFORMATION: locked nucleic acid; 5-methyl; phosphorothioate

<400> SEQUENCE: 7
ccattgtcac actcc 15

<210> SEQ ID NO 8
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by GalNAc(PS); phosphodiester
<220> FEATURE:
<221> NAME/KEY: misc_feature
<222> LOCATION: (2)..(2)
<223> OTHER INFORMATION: phosphodiester
<220> FEATURE:
<221> NAME/KEY: misc_feature
<222> LOCATION: (3)..(3)
<223> OTHER INFORMATION: locked nucleic acid; 5-methyl; phosphorothioate
<220> FEATURE:
<221> NAME/KEY: misc_feature
<222> LOCATION: (4)..(4)
<223> OTHER INFORMATION: phosphorothioate
<220> FEATURE:
<221> NAME/KEY: misc_feature
<222> LOCATION: (5)..(5)
<223> OTHER INFORMATION: locked nucleic acid; phosphorothioate
<220> FEATURE:
<221> NAME/KEY: misc_feature
<222> LOCATION: (6)..(7)
<223> OTHER INFORMATION: phosphorothioate
<220> FEATURE:
<221> NAME/KEY: misc_feature
<222> LOCATION: (8)..(9)
<223> OTHER INFORMATION: locked nucleic acid; phosphorothioate
<220> FEATURE:
<221> NAME/KEY: misc_feature
<222> LOCATION: (10)..(11)
<223> OTHER INFORMATION: phosphorothioate
<220> FEATURE:
<221> NAME/KEY: misc_feature
<222> LOCATION: (12)..(12)
<223> OTHER INFORMATION: locked nucleic acid; 5-methyl; phosphorothioate
<220> FEATURE:
<221> NAME/KEY: misc_feature
<222> LOCATION: (13)..(13)
<223> OTHER INFORMATION: phosphorothioate
<220> FEATURE:
<221> NAME/KEY: misc_feature
<222> LOCATION: (14)..(14)
<223> OTHER INFORMATION: locked nucleic acid; 5-methyl; phosphorothioate
<220> FEATURE:
<221> NAME/KEY: misc_feature
<222> LOCATION: (15)..(15)
<223> OTHER INFORMATION: phosphorothioate
<220> FEATURE:
<221> NAME/KEY: misc_feature
<222> LOCATION: (16)..(17)
<223> OTHER INFORMATION: locked nucleic acid; 5-methyl; phosphorothioate

<400> SEQUENCE: 8
aaccattgtc acactcc 17

<210> SEQ ID NO 9
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by GalNAc(PO); phosphodiester
<220> FEATURE:
<221> NAME/KEY: misc_feature
<222> LOCATION: (2)..(2)
<223> OTHER INFORMATION: phosphodiester
<220> FEATURE:
<221> NAME/KEY: misc_feature
<222> LOCATION: (3)..(3)
<223> OTHER INFORMATION: locked nucleic acid; 5-methyl; phosphorothioate
<220> FEATURE:
<221> NAME/KEY: misc_feature
<222> LOCATION: (4)..(4)
<223> OTHER INFORMATION: phosphorothioate
<220> FEATURE:
<221> NAME/KEY: misc_feature
<222> LOCATION: (5)..(5)
<223> OTHER INFORMATION: locked nucleic acid; phosphorothioate
<220> FEATURE:
<221> NAME/KEY: misc_feature
<222> LOCATION: (6)..(7)
<223> OTHER INFORMATION: phosphorothioate
<220> FEATURE:
<221> NAME/KEY: misc_feature
<222> LOCATION: (8)..(9)
<223> OTHER INFORMATION: locked nucleic acid; phosphorothioate
<220> FEATURE:
<221> NAME/KEY: misc_feature
<222> LOCATION: (10)..(11)
<223> OTHER INFORMATION: phosphorothioate
<220> FEATURE:
<221> NAME/KEY: misc_feature
<222> LOCATION: (12)..(12)
<223> OTHER INFORMATION: locked nucleic acid; 5-methyl; phosphorothioate
<220> FEATURE:
<221> NAME/KEY: misc_feature
<222> LOCATION: (13)..(13)
<223> OTHER INFORMATION: phosphorothioate
<220> FEATURE:
<221> NAME/KEY: misc_feature
<222> LOCATION: (14)..(14)
<223> OTHER INFORMATION: locked nucleic acid; 5-methyl; phosphorothioate
<220> FEATURE:
<221> NAME/KEY: misc_feature
<222> LOCATION: (15)..(15)
<223> OTHER INFORMATION: phosphorothioate
<220> FEATURE:
<221> NAME/KEY: misc_feature
<222> LOCATION: (16)..(17)
<223> OTHER INFORMATION: locked nucleic acid; 5-methyl; phosphorothioate

<400> SEQUENCE: 9
aaccattgtc acactcc 17

<210> SEQ ID NO 10
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by GalNAc(PS); phosphorothioate
linkage with R stereochemistry at that linkage
<220> FEATURE:
<221> NAME/KEY: misc_feature
<222> LOCATION: (2)..(2)

```
<223> OTHER INFORMATION: phosphorothioate linkage with R stereochemistry
      at that linkage
<220> FEATURE:
<221> NAME/KEY: misc_feature
<222> LOCATION: (3)..(3)
<223> OTHER INFORMATION: locked nucleic acid; 5-methyl; phosphorothioate
<220> FEATURE:
<221> NAME/KEY: misc_feature
<222> LOCATION: (4)..(4)
<223> OTHER INFORMATION: phosphorothioate
<220> FEATURE:
<221> NAME/KEY: misc_feature
<222> LOCATION: (5)..(5)
<223> OTHER INFORMATION: locked nucleic acid; phosphorothioate
<220> FEATURE:
<221> NAME/KEY: misc_feature
<222> LOCATION: (6)..(7)
<223> OTHER INFORMATION: phosphorothioate
<220> FEATURE:
<221> NAME/KEY: misc_feature
<222> LOCATION: (8)..(9)
<223> OTHER INFORMATION: locked nucleic acid; phosphorothioate
<220> FEATURE:
<221> NAME/KEY: misc_feature
<222> LOCATION: (10)..(11)
<223> OTHER INFORMATION: phosphorothioate
<220> FEATURE:
<221> NAME/KEY: misc_feature
<222> LOCATION: (12)..(12)
<223> OTHER INFORMATION: locked nucleic acid; 5-methyl; phosphorothioate
<220> FEATURE:
<221> NAME/KEY: misc_feature
<222> LOCATION: (13)..(13)
<223> OTHER INFORMATION: phosphorothioate
<220> FEATURE:
<221> NAME/KEY: misc_feature
<222> LOCATION: (14)..(14)
<223> OTHER INFORMATION: locked nucleic acid; 5-methyl; phosphorothioate
<220> FEATURE:
<221> NAME/KEY: misc_feature
<222> LOCATION: (15)..(15)
<223> OTHER INFORMATION: phosphorothioate
<220> FEATURE:
<221> NAME/KEY: misc_feature
<222> LOCATION: (16)..(17)
<223> OTHER INFORMATION: locked nucleic acid; 5-methyl; phosphorothioate

<400> SEQUENCE: 10

aaccattgtc acactcc                                                17


<210> SEQ ID NO 11
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by GalNAc(PS); phosphorothioate
      linkage with S stereochemistry at that linkage
<220> FEATURE:
<221> NAME/KEY: misc_feature
<222> LOCATION: (2)..(2)
<223> OTHER INFORMATION: phosphorothioate linkage with S stereochemistry
      at that linkage
<220> FEATURE:
<221> NAME/KEY: misc_feature
<222> LOCATION: (3)..(3)
<223> OTHER INFORMATION: locked nucleic acid; 5-methyl; phosphorothioate
<220> FEATURE:
<221> NAME/KEY: misc_feature
<222> LOCATION: (4)..(4)
<223> OTHER INFORMATION: phosphorothioate
<220> FEATURE:
<221> NAME/KEY: misc_feature
<222> LOCATION: (5)..(5)
```

<223> OTHER INFORMATION: locked nucleic acid; phosphorothioate
<220> FEATURE:
<221> NAME/KEY: misc_feature
<222> LOCATION: (6)..(7)
<223> OTHER INFORMATION: phosphorothioate
<220> FEATURE:
<221> NAME/KEY: misc_feature
<222> LOCATION: (8)..(9)
<223> OTHER INFORMATION: locked nucleic acid; phosphorothioate
<220> FEATURE:
<221> NAME/KEY: misc_feature
<222> LOCATION: (10)..(11)
<223> OTHER INFORMATION: phosphorothioate
<220> FEATURE:
<221> NAME/KEY: misc_feature
<222> LOCATION: (12)..(12)
<223> OTHER INFORMATION: locked nucleic acid; 5-methyl; phosphorothioate
<220> FEATURE:
<221> NAME/KEY: misc_feature
<222> LOCATION: (13)..(13)
<223> OTHER INFORMATION: phosphorothioate
<220> FEATURE:
<221> NAME/KEY: misc_feature
<222> LOCATION: (14)..(14)
<223> OTHER INFORMATION: locked nucleic acid; 5-methyl; phosphorothioate
<220> FEATURE:
<221> NAME/KEY: misc_feature
<222> LOCATION: (15)..(15)
<223> OTHER INFORMATION: phosphorothioate
<220> FEATURE:
<221> NAME/KEY: misc_feature
<222> LOCATION: (16)..(17)
<223> OTHER INFORMATION: locked nucleic acid; 5-methyl; phosphorothioate

<400> SEQUENCE: 11
aaccattgtc acactcc 17

<210> SEQ ID NO 12
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by GalNAc(PS); phosphodiester
<220> FEATURE:
<221> NAME/KEY: misc_feature
<222> LOCATION: (2)..(2)
<223> OTHER INFORMATION: phosphodiester
<220> FEATURE:
<221> NAME/KEY: misc_feature
<222> LOCATION: (3)..(3)
<223> OTHER INFORMATION: locked nucleic acid; 5-methyl; phosphorothioate
<220> FEATURE:
<221> NAME/KEY: misc_feature
<222> LOCATION: (4)..(5)
<223> OTHER INFORMATION: locked nucleic acid; phosphorothioate
<220> FEATURE:
<221> NAME/KEY: misc_feature
<222> LOCATION: (6)..(14)
<223> OTHER INFORMATION: phosphorothioate
<220> FEATURE:
<221> NAME/KEY: misc_feature
<222> LOCATION: (15)..(16)
<223> OTHER INFORMATION: locked nucleic acid; 5-methyl; phosphorothioate
<220> FEATURE:
<221> NAME/KEY: misc_feature
<222> LOCATION: (17)..(17)
<223> OTHER INFORMATION: locked nucleic acid; phosphorothioate

<400> SEQUENCE: 12
aacaagatcc aaagcct 17

-continued

```
<210> SEQ ID NO 13
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 13

ccattgtcac actcc                                                         15
```

NUCLEIC ACID CONJUGATES AND USES THEREOF

RELATED APPLICATIONS

This application is a continuation of U.S. application Ser. No. 16/317,229, filed Jan. 11, 2019, which is a national stage filing under 35 U.S.C. § 371 of international application number PCT/US2017/041469, filed Jul. 7, 2017, which claims priority to U.S. Provisional Application No. 62/478,499, filed on Mar. 29, 2017, and to U.S. Provisional Application No. 62/360,518, filed on Jul. 11, 2016, the contents of which are incorporated herein by reference in their entireties.

BACKGROUND

Nucleic acids are an important class of therapeutics that can be used to treat a wide range of diseases and conditions. For example, oligonucleotides can target RNA transcripts to modulate (e.g., reduce or silence; increase or amplify) gene expression, thereby mitigating or promoting the expression of proteins implicated in certain diseases. Despite advances in oligonucleotide therapy, a common challenge is the targeted delivery of oligonucleotides with desirable pharmacokinetic properties. A similar challenge is faced for delivery of other therapeutic nucleic acids, such as synthetic siRNA, microRNA mimics and mRNAs. Chemical modifications of nucleic acids such as oligonucleotides (e.g., with targeting moieties) can aid in the delivery of the agents to specific organs and/or cells, aid in transmembrane delivery, and even confer improved pharmacokinetic properties such as in vivo stability. Enhanced targeting and/or slower degradation of nucleic acids such as oligonucleotides can result in increased potency and efficacy, which can allow for lower or less frequent dosing in addition to improved toxicity profiles.

SUMMARY

Provided herein are conjugates useful for delivering nucleic acids to cells or tissues. In some embodiments, conjugates provided herein comprise targeting ligands, such as sugars, folates, or cell-penetrating peptides, linked to a nucleic acid. Such conjugates are useful for delivering the nucleic acids (e.g., oligonucleotides, DNAs, DNA/RNA hybrid molecules, and RNAs such as mRNAs, non-coding RNAs, and guide RNAs) to a target cell or tissue (e.g., in a subject). In some embodiments, targeting ligands are linked to a nucleic acid via one or more linkers. However, in some embodiments, targeting ligands are linked to a nanoparticle, e.g., a lipid nanoparticle, with which is complexed a nucleic acid. In some embodiments, conjugates provided herein are useful for delivering therapeutic nucleic acids for the treatment and/or prevention of diseases and conditions.

In one aspect, provided herein is a conjugate of Formula (I-a):

(I-a)

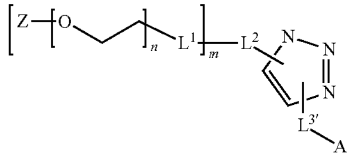

or a pharmaceutically acceptable salt thereof, wherein: A is a group comprising a nucleic acid or a nanoparticle component (e.g., a lipid nanoparticle component); each Z independently is a sugar, a folate, or a cell-penetrating peptide; each of $L^1$, $L^2$, and $L^{3'}$ is independently a bond, optionally substituted alkylene, or optionally substituted heteroalkylene; wherein each $L^1$ optionally comprises a triazole; m is an integer from 3 to 10, inclusive; and n is an integer from 1 to 10, inclusive.

In an embodiment, m is 3, each Z independently is a sugar, and the conjugate is of Formula (IV):

(IV)

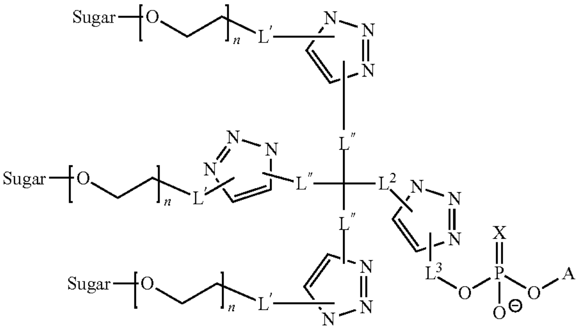

or a pharmaceutically acceptable salt thereof.

In an embodiment, the conjugate is of Formula (IV-a):

(IV-a)

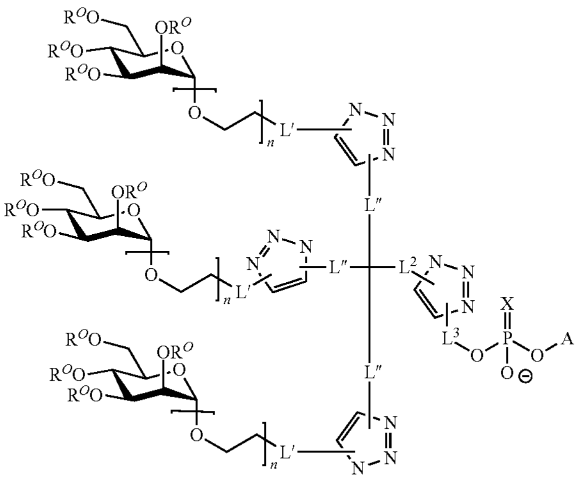

wherein each instance of $R^O$ is independently hydrogen, optionally substituted alkyl, optionally substituted acyl, or an oxygen protecting group.

In an embodiment, the conjugate is of Formula (V):

(V)

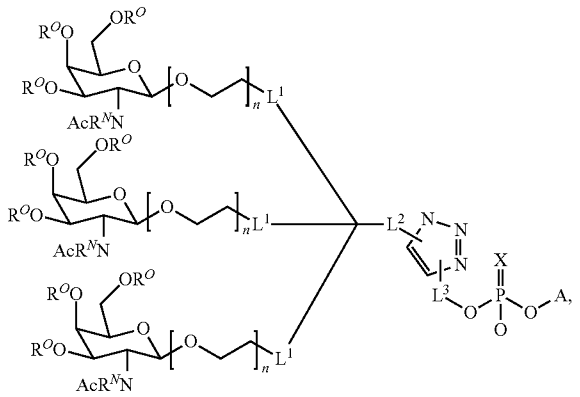

or a pharmaceutically acceptable salt, hydrate, solvate, polymorph, co-crystal, tautomer, stereoisomer, isotopically labeled derivative, or prodrug thereof, wherein A is a group comprising a nucleic acid (e.g., an oligonucleotide or mRNA), and wherein $L^1$, $L^2$, $L^3$, X, n, $R^N$, and $R^O$ are as defined above.

For example, in certain embodiments, the conjugate is of one of the following formulae:

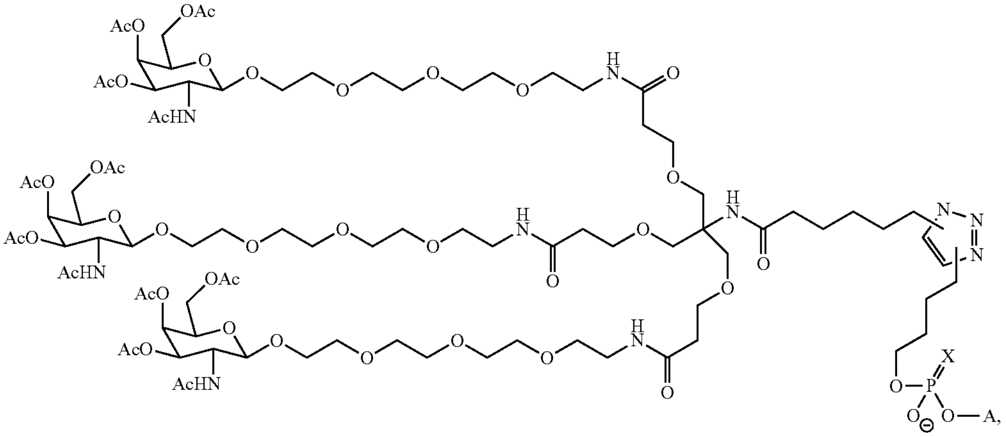

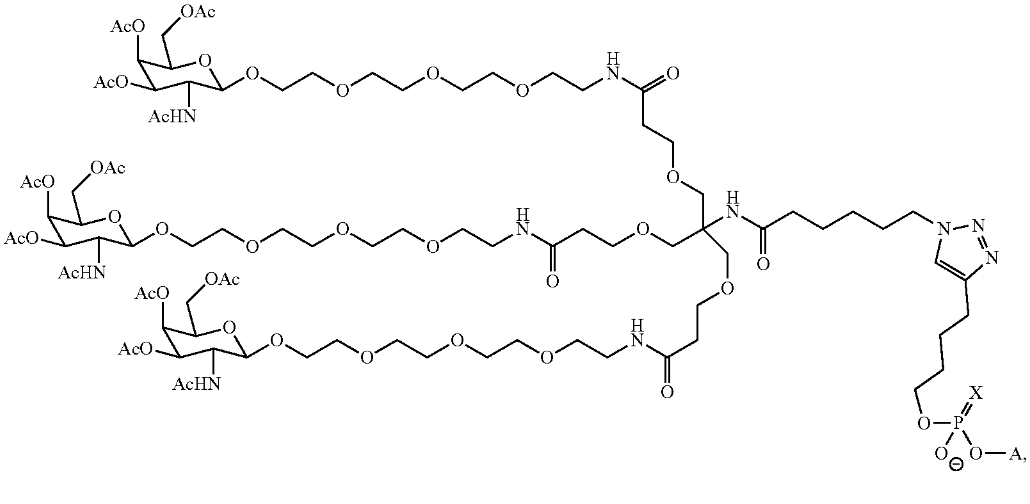

-continued

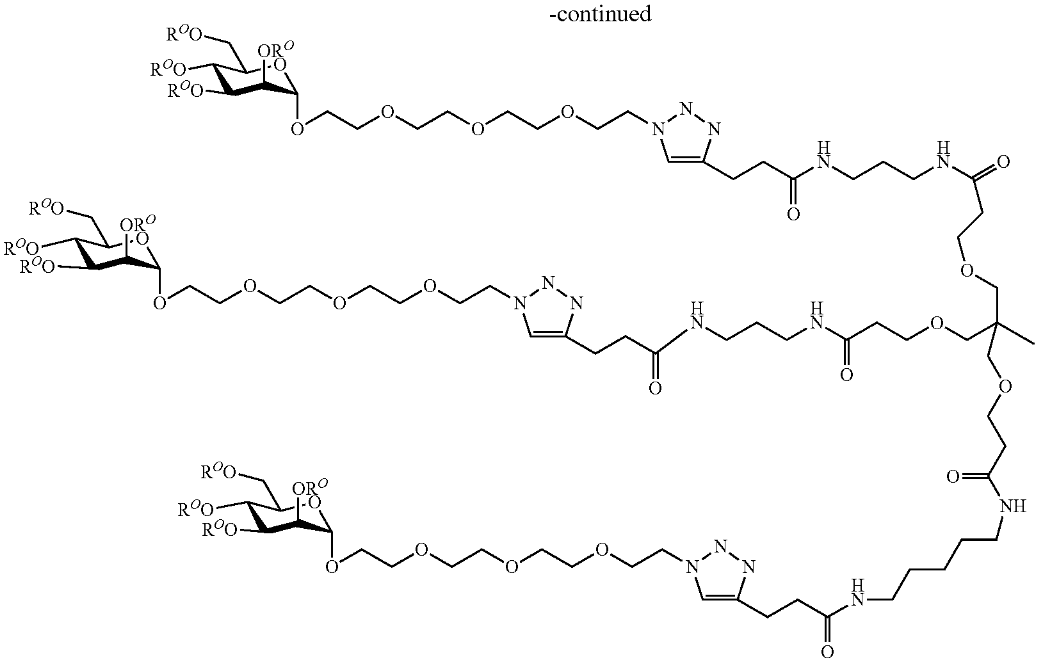

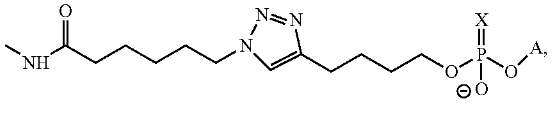

or a pharmaceutically acceptable salt thereof.

As described herein, the sugar, folate and cell-penetrating peptide targeting moieties provided herein can be used in the delivery of a nucleic acids (e.g., oligonucleotides or mRNAs), as well as agents other than nucleic acids. Examples of agents other than nucleic acids which can be conjugated to the targeting moieties include, but are not limited to, small molecules (e.g., drug compounds), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, lipids (e.g., cationic, anionic or neutral lipids), hormones, and vitamins.

The present invention also provides compounds (e.g., nucleic acids, such as oligonucleotides or mRNAs, or other agents) comprising a GalNAc targeting moiety of the following formula:

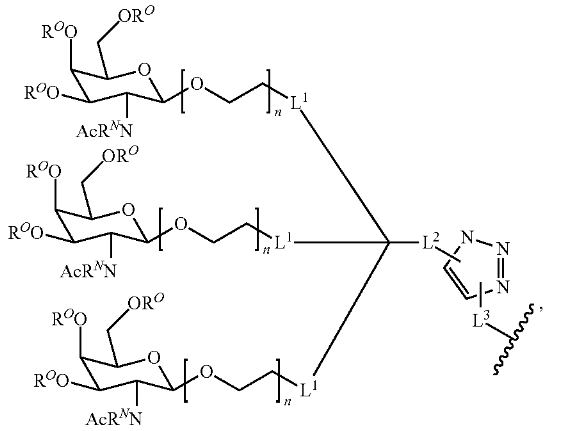

and pharmaceutically acceptable salts, hydrates, solvates, polymorphs, co-crystals, tautomers, stereoisomers, isotopically labeled derivatives, and prodrugs thereof, wherein $L^1$, $L^2$, $L^3$, n, $R^N$, and $R^O$ are as defined herein. For example, in certain embodiments, a compound (e.g., nucleic acid such as an oligonucleotide or mRNA or other RNAs) of the present invention comprises a GalNAc targeting moiety of one of the following formulae:

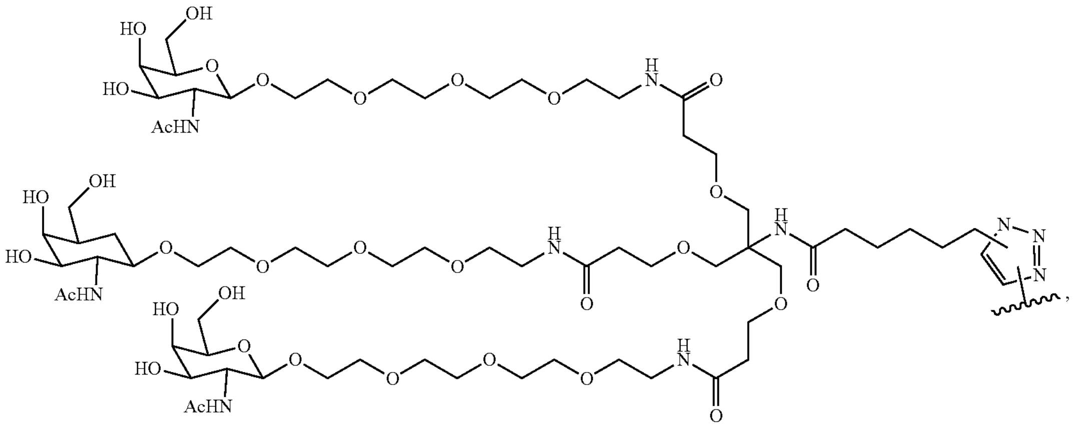

, or

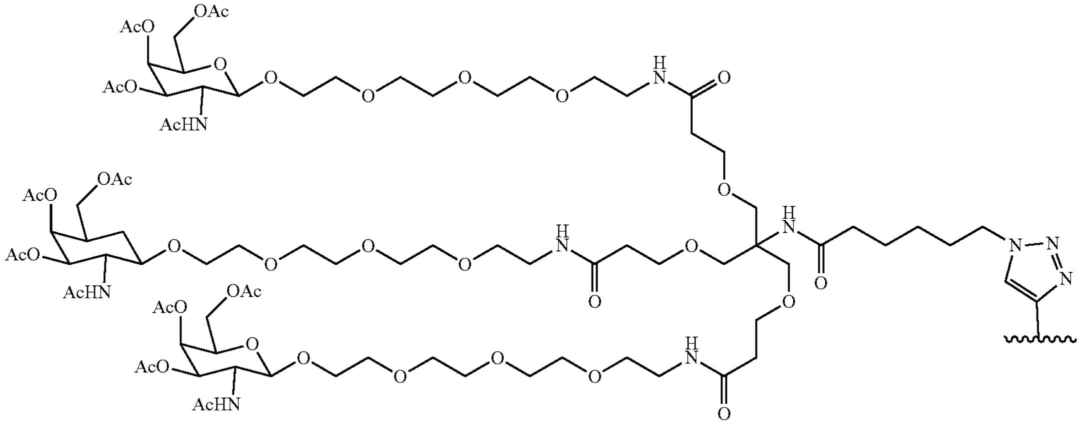

.

In other embodiments, for example, a compound (e.g., nucleic acid such as an oligonucleotide or mRNA) of the present invention comprises GalNAc targeting moiety of one of the following formulae:

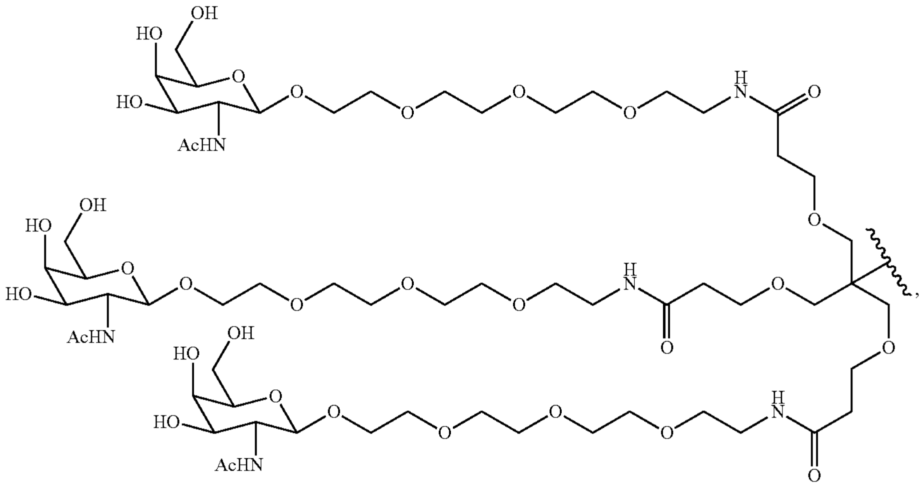

, or

-continued

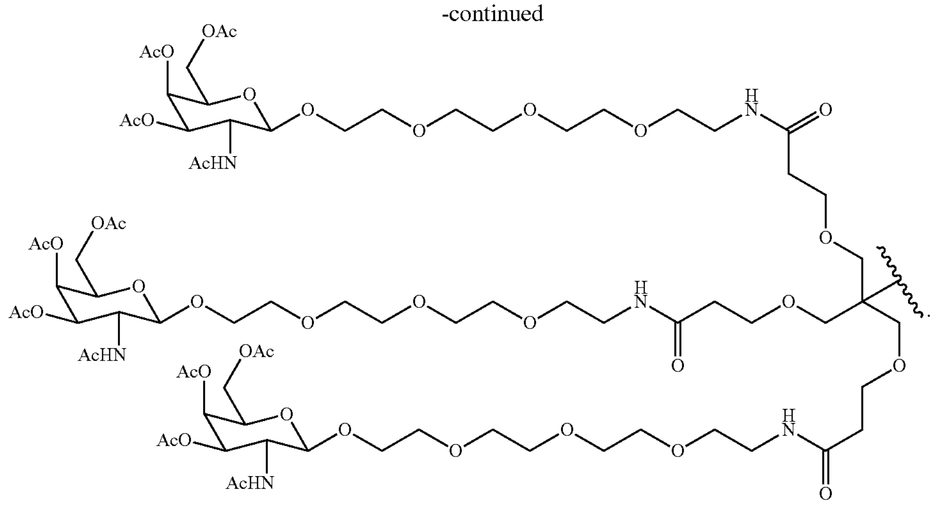

In another aspect, the present invention provides methods for preparing the conjugates and compounds described herein, and intermediates which are useful in the preparation of conjugates and compounds described herein. As discussed below, in certain embodiments, conjugates or compounds described herein can be prepared via click chemistry (e.g., alkyne-azide cycloaddition reactions).

In another aspect, the present invention provides pharmaceutical compositions (i.e., formulations) comprising the inventive conjugates and compounds described herein.

The conjugates, compounds, and pharmaceutical compositions described herein can be used to deliver nucleic acids (e.g., oligonucleotides or mRNAs) to cells, and therefore can be used in the treatment and/or prevention of diseases or conditions (e.g., genetic diseases, proliferative diseases (e.g., cancer), inflammatory diseases, autoimmune diseases, liver diseases, hematological diseases, neurological diseases, ocular conditions, cardiovascular diseases, or metabolic disorders (e.g., diabetic conditions)). Provided herein are methods of delivering an nucleic acid (e.g., oligonucleotide or mRNA) to a cell (e.g., in vitro, in vivo, or ex vivo delivery). Also provided herein are methods of treating and/or preventing a disease or condition in a subject in need thereof. In another aspect, the invention provides methods for modulating gene expression (e.g., increasing or reducing gene expression) in a subject or a cell. The methods provided herein, in certain embodiments, comprise contacting a cell and/or administering to a subject a conjugate or compound described herein.

In yet another aspect, the present invention provides kits comprising the conjugates, compounds, and pharmaceutical compositions described herein. The present invention also provides kits comprising intermediates, and optionally reagents, for the preparation of the conjugates and compounds described herein.

The details of certain embodiments of the invention are set forth herein. Other features, objects, and advantages of the invention will be apparent from the Detailed Description, Figures, Examples, and Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions*, p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "Heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl (C) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

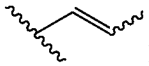
)

may be an (E)- or (Z)-double bond.

The term “heteroalkenyl” refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain (“hetero$C_{2-10}$ alkenyl”). In some embodiments, a heteroalkenyl group has 2 to 9 carbon atoms at least one double bond, and 1 or more heteroatoms within the parent chain (“hetero$C_{2-9}$ alkenyl”). In some embodiments, a heteroalkenyl group has 2 to 8 carbon atoms, at least one double bond, and 1 or more heteroatoms within the parent chain (“hetero$C_{2-8}$ alkenyl”). In some embodiments, a heteroalkenyl group has 2 to 7 carbon atoms, at least one double bond, and 1 or more heteroatoms within the parent chain (“hetero$C_{2-7}$ alkenyl”). In some embodiments, a heteroalkenyl group has 2 to 6 carbon atoms, at least one double bond, and 1 or more heteroatoms within the parent chain (“hetero$C_{2-6}$ alkenyl”). In some embodiments, a heteroalkenyl group has 2 to 5 carbon atoms, at least one double bond, and 1 or 2 heteroatoms within the parent chain (“hetero$C_{2-5}$ alkenyl”). In some embodiments, a heteroalkenyl group has 2 to 4 carbon atoms, at least one double bond, and lor 2 heteroatoms within the parent chain (“hetero$C_{2-4}$ alkenyl”). In some embodiments, a heteroalkenyl group has 2 to 3 carbon atoms, at least one double bond, and 1 heteroatom within the parent chain (“hetero$C_{2-3}$ alkenyl”). In some embodiments, a heteroalkenyl group has 2 to 6 carbon atoms, at least one double bond, and 1 or 2 heteroatoms within the parent chain (“hetero$C_{2-6}$ alkenyl”). Unless otherwise specified, each instance of a heteroalkenyl group is independently unsubstituted (an “unsubstituted heteroalkenyl”) or substituted (a “substituted heteroalkenyl”) with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term “alkynyl” refers to a radical of a straight-chain or branched hydrocarbon group having from 2 to 10 carbon atoms and one or more carbon-carbon triple bonds (e.g., 1, 2, 3, or 4 triple bonds) (“$C_{2-10}$ alkynyl”). In some embodiments, an alkynyl group has 2 to 9 carbon atoms (“$C_{2-9}$ alkynyl”). In some embodiments, an alkynyl group has 2 to 8 carbon atoms (“$C_{2-8}$ alkynyl”). In some embodiments, an alkynyl group has 2 to 7 carbon atoms (“$C_2$-7 alkynyl”). In some embodiments, an alkynyl group has 2 to 6 carbon atoms (“$C_{2-6}$ alkynyl”). In some embodiments, an alkynyl group has 2 to 5 carbon atoms (“$C_{2-5}$ alkynyl”). In some embodiments, an alkynyl group has 2 to 4 carbon atoms (“$C_{2-4}$ alkynyl”). In some embodiments, an alkynyl group has 2 to 3 carbon atoms (“$C_{2-3}$ alkynyl”). In some embodiments, an alkynyl group has 2 carbon atoms (“$C_2$ alkynyl”). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an “unsubstituted alkynyl”) or substituted (a “substituted alkynyl”) with one or more substituents. In certain embodiments, the alkynyl group is an unsubstituted $C_{2-10}$ alkynyl. In certain embodiments, the alkynyl group is a substituted $C_{2-10}$ alkynyl.

The term “heteroalkynyl” refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain (“hetero$C_{2-10}$ alkynyl”). In some embodiments, a heteroalkynyl group has 2 to 9 carbon atoms, at least one triple bond, and 1 or more heteroatoms within the parent chain (“hetero$C_{2-9}$ alkynyl”). In some embodiments, a heteroalkynyl group has 2 to 8 carbon atoms, at least one triple bond, and 1 or more heteroatoms within the parent chain (“hetero$C_{2-8}$ alkynyl”). In some embodiments, a heteroalkynyl group has 2 to 7 carbon atoms, at least one triple bond, and 1 or more heteroatoms within the parent chain (“hetero$C_{2-7}$ alkynyl”). In some embodiments, a heteroalkynyl group has 2 to 6 carbon atoms, at least one triple bond, and 1 or more heteroatoms within the parent chain (“hetero$C_{2-6}$ alkynyl”). In some embodiments, a heteroalkynyl group has 2 to 5 carbon atoms, at least one triple bond, and 1 or 2 heteroatoms within the parent chain (“hetero$C_{2-5}$ alkynyl”). In some embodiments, a heteroalkynyl group has 2 to 4 carbon atoms, at least one triple bond, and lor 2 heteroatoms within the parent chain (“hetero$C_{2-4}$ alkynyl”). In some embodiments, a heteroalkynyl group has 2 to 3 carbon atoms, at least one triple bond, and 1 heteroatom within the parent chain (“hetero$C_{2-3}$ alkynyl”). In some embodiments, a heteroalkynyl group has 2 to 6 carbon atoms, at least one triple bond, and 1 or 2 heteroatoms within the parent chain (“hetero$C_{2-6}$ alkynyl”). Unless otherwise specified, each instance of a heteroalkynyl group is independently unsubstituted (an “unsubstituted heteroalkynyl”) or substituted (a “substituted heteroalkynyl”) with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term “carbocyclyl” or “carbocyclic” refers to a radical of a non-aromatic cyclic hydrocarbon group having from 3 to 14 ring carbon atoms (“$C_{3-14}$ carbocyclyl”) and zero heteroatoms in the non-aromatic ring system. In some embodiments, a carbocyclyl group has 3 to 10 ring carbon atoms (“$C_{3-10}$ carbocyclyl”). In some embodiments, a carbocyclyl group has 3 to 8 ring carbon atoms (“$C_{3-8}$ carbocyclyl”). In some embodiments, a carbocyclyl group has 3 to 7 ring carbon atoms (“$C_{3-7}$ carbocyclyl”). In some embodiments, a carbocyclyl group has 3 to 6 ring carbon atoms (“$C_{3-6}$ carbocyclyl”). In some embodiments, a carbocyclyl group has 4 to 6 ring carbon atoms (“$C_{4-6}$ carbocyclyl”). In some embodiments, a carbocyclyl group has 5 to 6 ring carbon atoms (“$C_{5-6}$ carbocyclyl”). In some embodiments, a carbocyclyl group has 5 to 10 ring carbon atoms (“$C_{5-10}$ carbocyclyl”). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl. Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R—$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3$ $—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}P(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, $—OR^{cc}$, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)(OR^{ee})_2$, $—P(=O)(R^{ee})_2$, $—OP(=O)(R^{ee})_2$, $—OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3$+$X^-$, —NH($C_{1-6}$ alkyl)$_2$$^+X^-$, —$NH_2$($C_{1-6}$ alkyl)$^+X^-$, —$NH_3$$^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3$$^+X^-$, —OP($OR^{cc}$)$_2$, —OP($OR^{cc}$)$_3$$^+X^-$, —OP(=O)($R^{aa}$)$_2$, —OP(=O)($OR^{cc}$)$_2$, and —OP(=O)(N($R^{bb}$))$_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3$+$X^-$, wherein $R^{bb}$ and $X^-$ are as defined herein.

The term "sulfonyl" refers to a group selected from —$SO_2$N($R^{bb}$)$_2$, —$SO_2R^{aa}$, and —$SO_2ORa^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)$OR^{X1}$, —C(=O)—O—C(=O)$R^{X1}$, —C(=O)$SR^{X1}$, —C(=O)N($R^{X1}$)$_2$, —C(=S)$R^{X1}$, —C(=S)N($R^{X1}$)$_2$, and —C(=S)S($R^{X1}$), —C(=$NR^{X1}$)$R^{X1}$, —C(=$NR^{X1}$)$OR^{X1}$, —C(=$NR^{X1}$)$SR^{X1}$, and —C(=$NR^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones ($—C(═O)R^{aa}$), carboxylic acids ($—CO_2H$), aldehydes ($—CHO$), esters ($—CO_2R^{aa}$, $—C(═O)SR^{aa}$, $—C(═S)SR^{aa}$), amides ($—C(═O)N(R^{bb})_2$, $—C(═O)NR^{bb}SO_2R^{aa}$, $—C(═S)N(R^{bb})_2$), and imines ($—C(═NR^{bb})R^{aa}$, $—C(═NR^{bb})OR^{aa}$), $—C(═NR^{bb})N(R^{bb})_2$), wherein $R^{aa}$ and $R^{bb}$ are as defined herein.

Nitrogen atoms can be substituted or unsubstituted as valency permits, and include primary, secondary, carbocyclic, tertiary, and quaternary nitrogen atoms. Exemplary nitrogen atom substituents include, but are not limited to, hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{bb})R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)(OR^{cc})_2$, $—P(═O)(R^{aa})_2$, $—P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, $—OR^{aa}$, $—N(R^{cc})_2$, $—C(═O)R^{aa}$, $—C(═O)N(R^{cc})_2$, $—CO_2R^{aa}$, $—SO_2R^{aa}$, $—C(═NR^{cc})R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., $—C(═O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., $—C(═O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(═O)_2R^{aa}$) include, but are not limited to, p-toluenesulfonamide (Ts), benzenesulfonamide, 2,3,6-trimethyl- 4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3{}^+X^-$, $—P(OR^{cc})_2$, $—P(OR^{cc})_3{}^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)$SR^{aa}$, —C(═O)$R^{aa}$, —$CO_2R^{aa}$, —C(═O)$N(R^{bb})_2$, —C(═$N^{Rb}$)$R^{aa}$, —C(═$NR^{bb}$)$OR^{aa}$, —C(═$NR^{bb}$)$N(R^{bb})_2$, —S(═O)$R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

Whereas a compound or conjugate described herein has a formula depicting a formal negative charge, it is understood that the compound or conjugate further comprises a suitable cationic counterion such that the net charge of compound or conjugate is zero. Suitable cationic counterions are known in the art and include, for example, hydronium ($H_3O^+$), sodium, potassium, calcium, magnesium, ammonium and the like.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_5$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue.

Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "ocular condition" refers to any disease or condition involving the eye of a subject. Examples of ocular conditions include, accommodative dysfunction, amblyopia, astigmatism, blepharitis, cataract, chalazion, color vision deficiency, computer vision syndrome, conjunctivitis, convergence insufficiency, corneal abrasion, crossed eyes, diabetic retinopathy, dry eye, farsightedness, floaters and spots, glaucoma, hordeolum, hyperopia, keratitis, keratoconus, lazy eye, macular degeneration (e.g., age-related macular degeneration (AMD)), migraine with aura, myopia, nearsightedness, nystagmus, ocular allergies, ocular hypertension, ocular migraine visual disturbance, pinquecula, presbyopia, pterygium, ptosis, retinal detachment, retinitis pigmentosa, ocular cancers (e.g., retinoblastoma), strabismus, sty, subconjunctival hemorrhage, and uveitis.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic *porphyria*, hepatic *porphyria* (e.g., acute intermittent *porphyria, porphyria cutanea tarda*), and Zellweger syndrome.

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

A "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

BRIEF DESCRIPTION OF THE DRAWINGS

The accompanying drawings, which constitute a part of this specification, illustrate several embodiments of the invention and together with the description, serve to explain the principles of the invention.

FIG. 8 shows exemplary chiral phosphorothioates and the expected cleavage patterns. Sequences correspond to SEQ ID NO: 13.

DETAILED DESCRIPTION

Conjugates and Compounds

Figure 1:
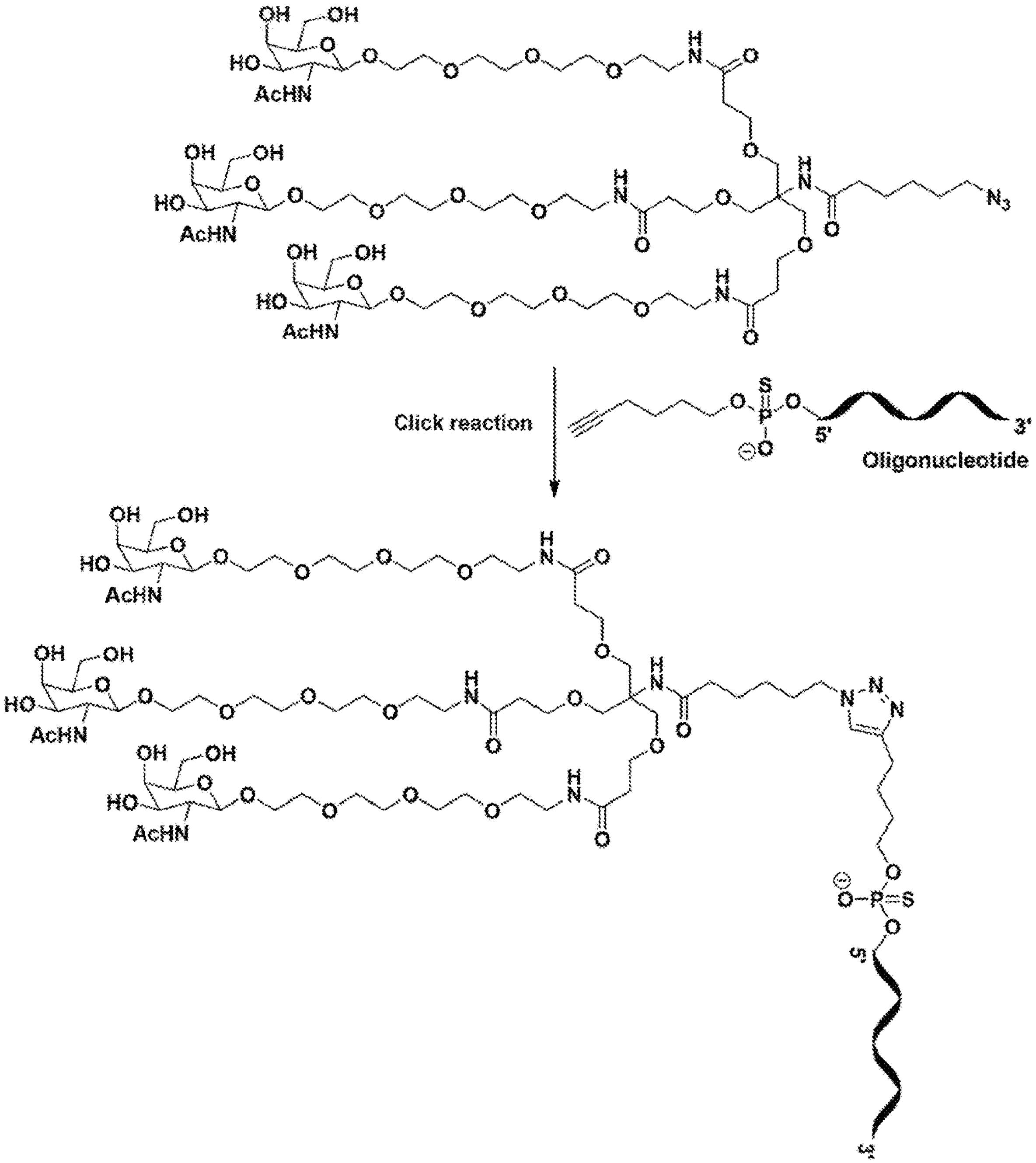
FIG. 1 shows a general scheme for the alkyne-azide click chemistry reaction which can be used to form GalNAc-oligonucleotide conjugates.

One aspect of the present invention relates to conjugates comprising an nucleic acid (e.g., an oligonucleotide, DNA, DNA/RNA hybrid molecule, or RNA such as an mRNA, non-coding RNA, or guide RNA) and a targeting moiety (e.g., GalNAc targeting moiety). Conjugates of the present invention are useful in delivering nucleic acids (e.g., oligonucleotides, DNAs, DNA/RNA hybrid molecules, or RNAs such as mRNAs, non-coding RNAs, or guide RNAs) to cells and are therefore useful in the treatment and/or prevention of diseases.

In one aspect, provided herein is a conjugate of Formula (I-a):

(I-a)

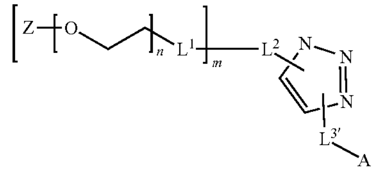

or a pharmaceutically acceptable salt thereof, wherein:

A is a group comprising a nucleic acid or a lipid nanoparticle component;

each Z independently is a sugar, a folate, or a cell-penetrating peptide;

each of $L^1$, $L^2$, and $L^{3'}$ is independently a bond, optionally substituted alkylene, or optionally substituted heteroalkylene;

wherein each $L^1$ optionally comprises a triazole; m is an integer from 3 to 10, inclusive; and n is an integer from 1 to 10, inclusive.

In an embodiment, $L^{3'}$ comprises a divalent linker selected from the group of phoshodiesters, phosphorothioates, amides, esters, carbamates and ureas.

In an embodiment, the conjugate is of Formula (I-b):

(I-b)

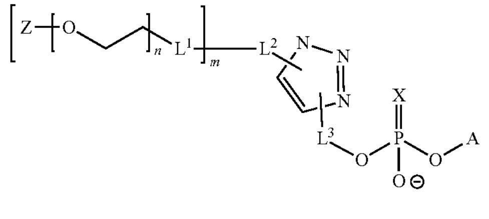

or a pharmaceutically acceptable salt thereof, wherein:

A is a group comprising a nucleic acid;

X is O or S; Z is a sugar, a folate, or a cell-penetrating peptide;

each of $L^1$, $L^2$, and $L^3$ is independently a bond, optionally substituted alkylene, or optionally substituted heteroalkylene;

wherein each $L^1$ optionally comprises a triazole; m is an integer from 3 to 10, inclusive; and n is an integer from 1 to 10, inclusive.

In an embodiment, the conjugate is of Formula (II):

(II)

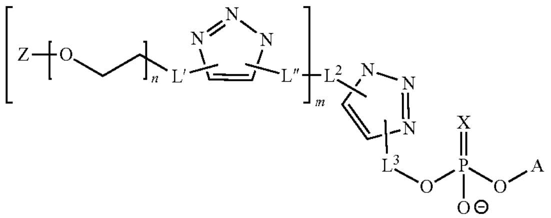

or a pharmaceutically acceptable salt thereof, wherein: each of L' and L" is independently a bond, optionally substituted alkylene, or optionally substituted heteroalkylene.

In an embodiment, m is 3, each Z independently is a sugar, and the conjugate is of Formula (III):

(III)

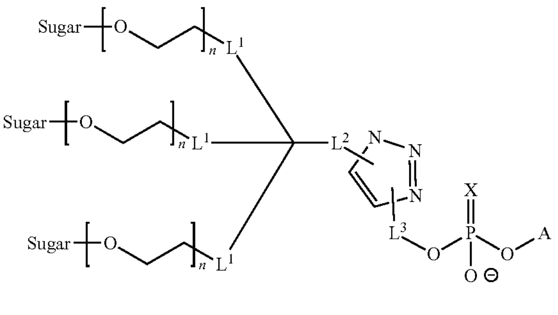

or a pharmaceutically acceptable salt thereof.

In an embodiment, m is 3, each Z independently is a sugar, and the conjugate is of Formula (IV):

(IV)

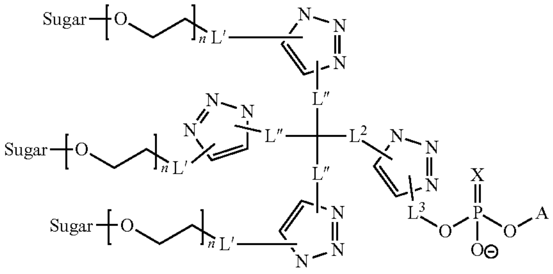

or a pharmaceutically acceptable salt thereof.

In an embodiment, each Z is GalNAc or a derivative thereof.

In an embodiment, each Z is mannose or a derivative thereof.

In an embodiment, the conjugate is of Formula (IV-a):

(IV-a)

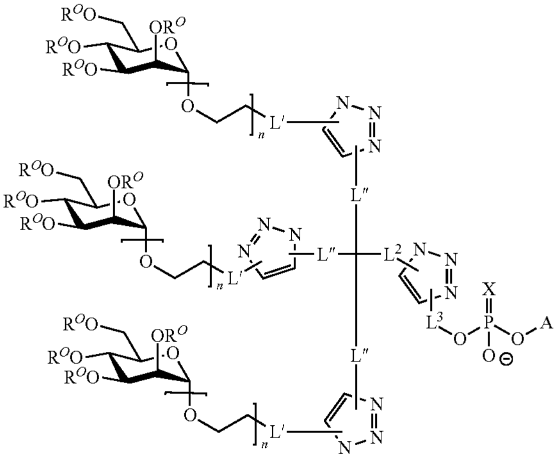

wherein each instance of $R^O$ is independently hydrogen, optionally substituted alkyl, optionally substituted acyl, or an oxygen protecting group.

In an embodiment, the conjugate of Formula (IV-a) is of Formula (IV-b):
(IV-b)
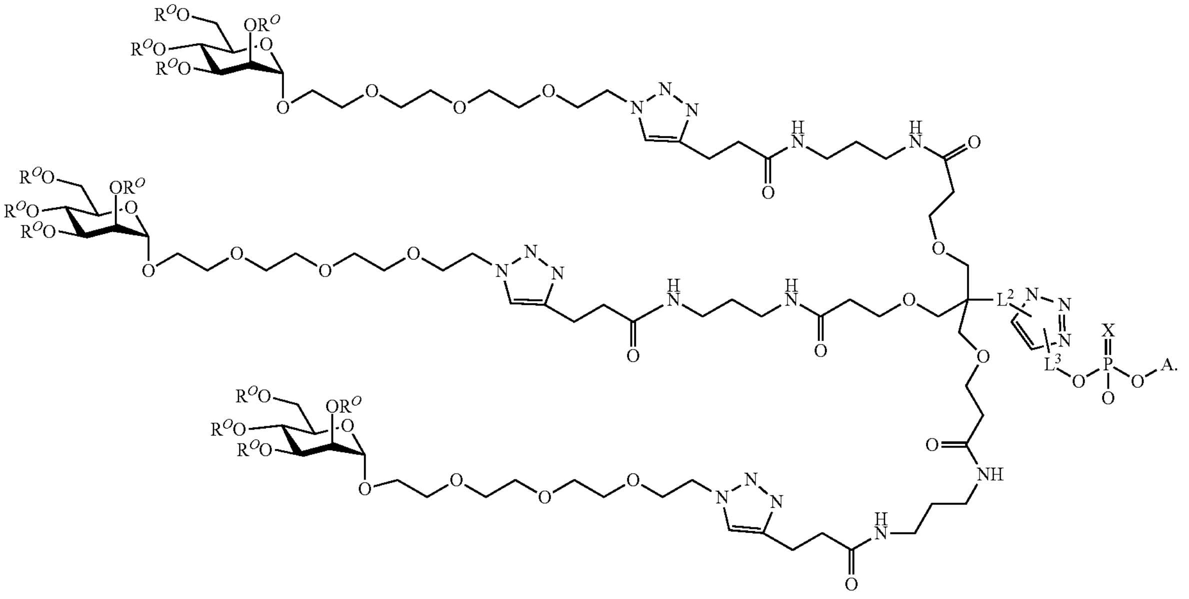
In an embodiment, the conjugate of Formula (IV-a) is of Formula (IV-c):
(IV-c)
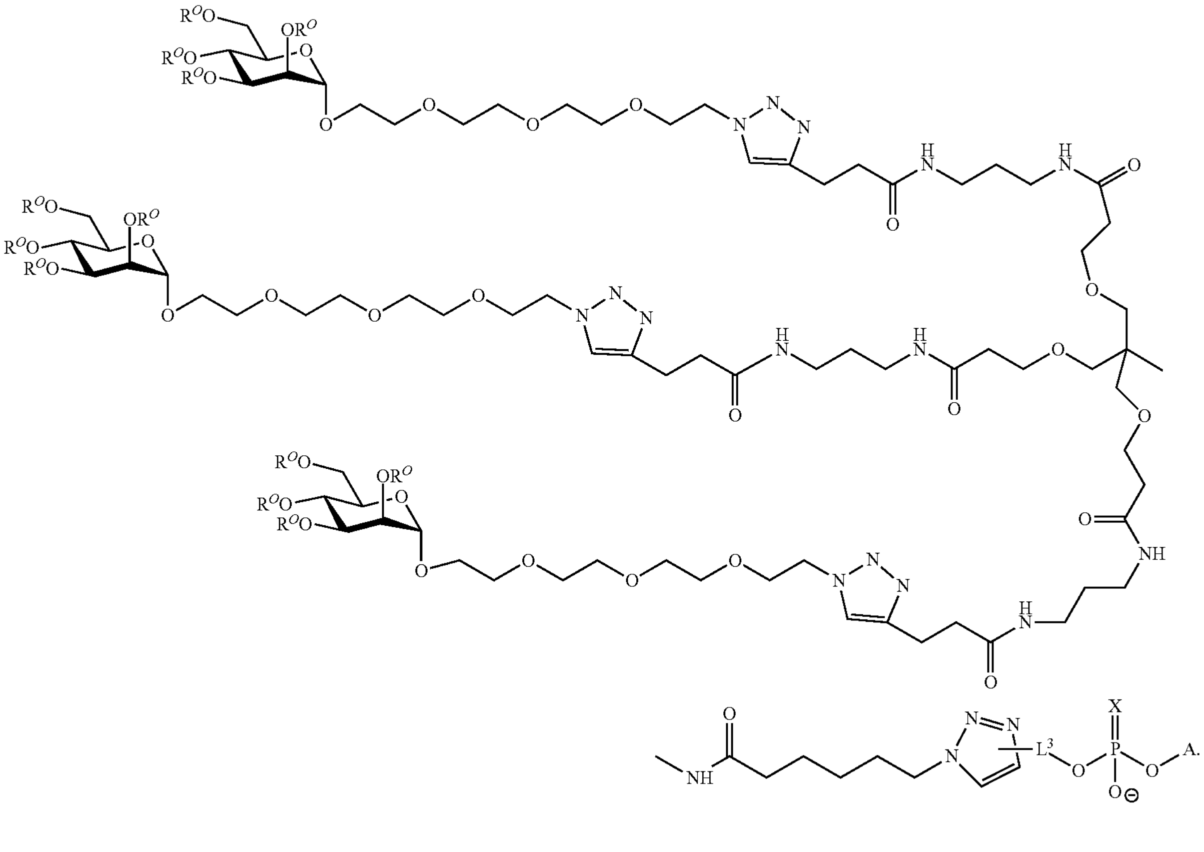

In an embodiment, the conjugate of Formula (IV-a) is of Formula (IV-d):
(IV-d)
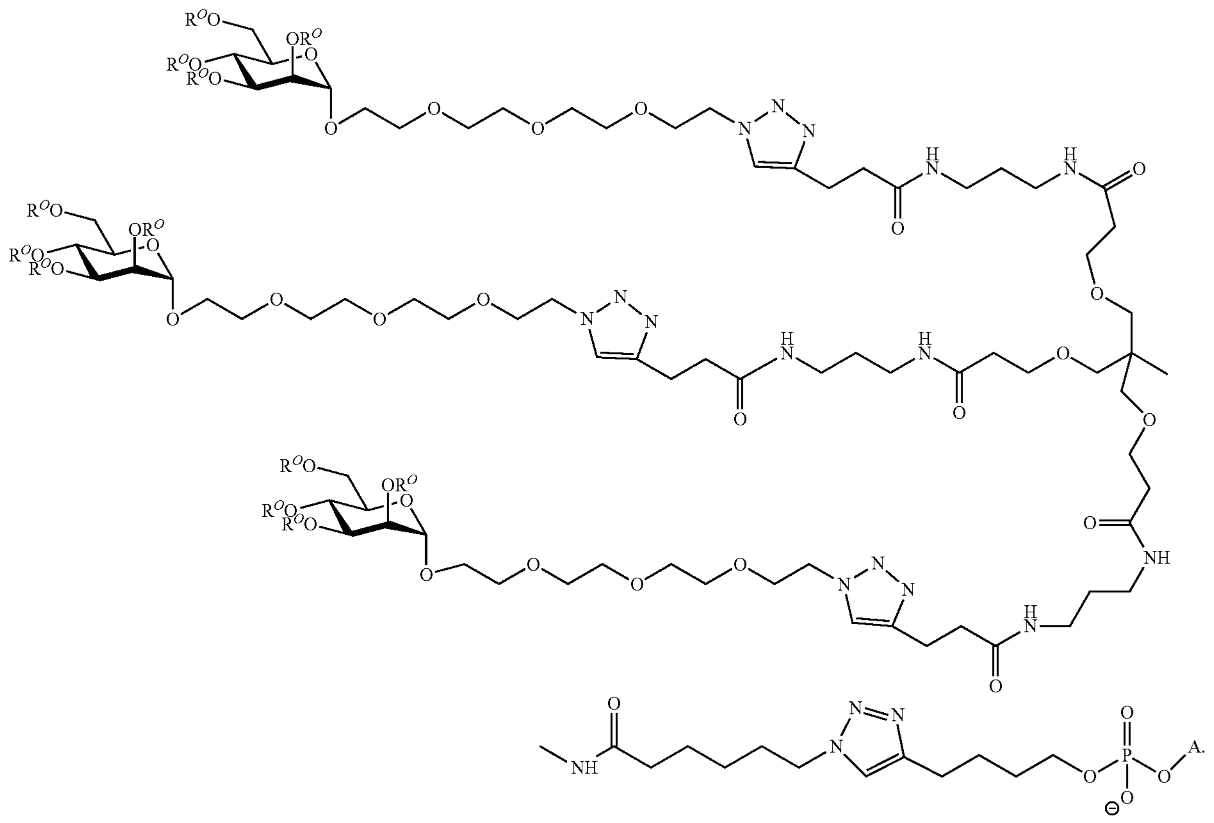
In an embodiment, the conjugate of Formula (IV-a) is of Formula (IV-e):

(IV-e)
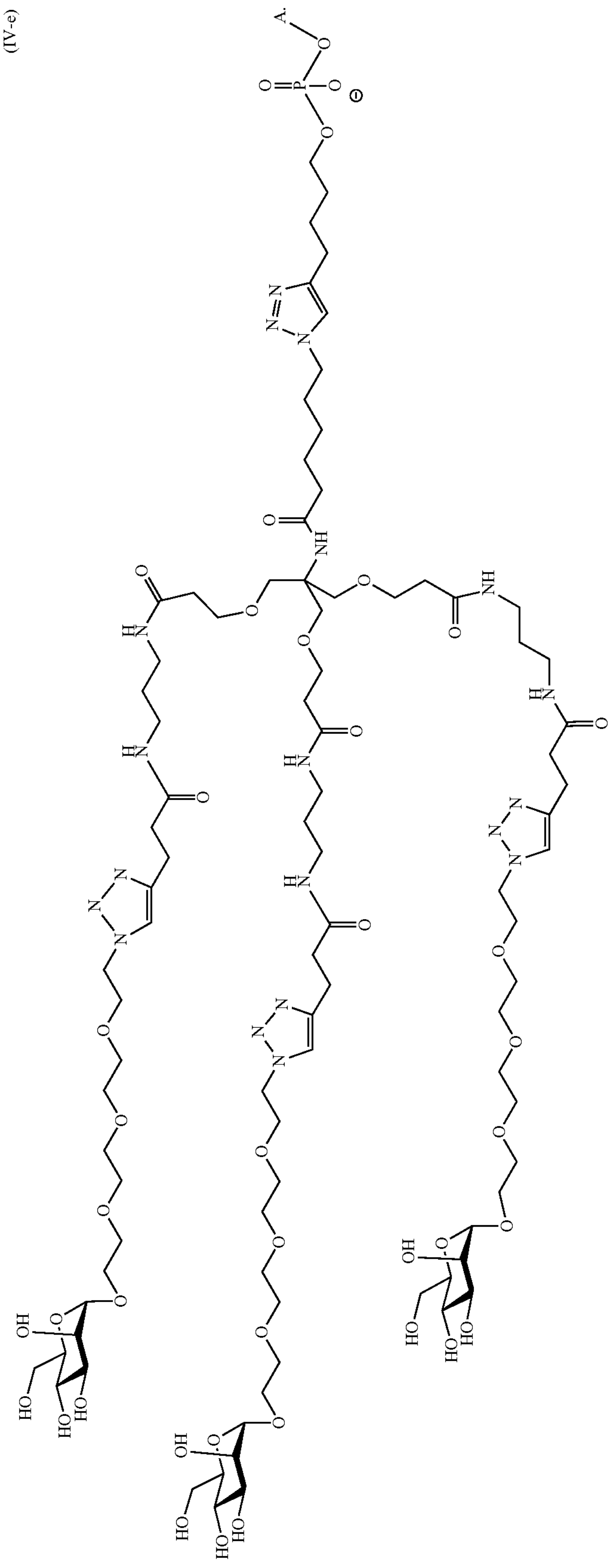

In another aspect, provided herein is a conjugate of Formula (V):

(V)

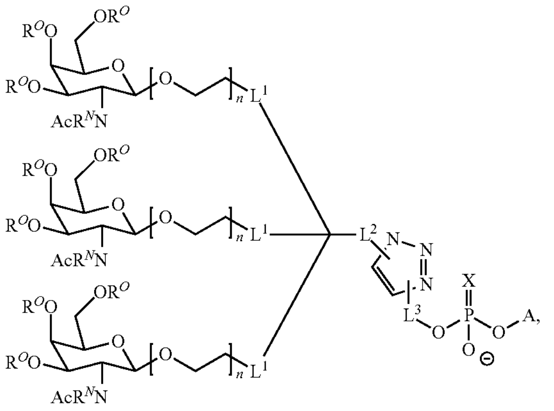

or a pharmaceutically acceptable salt, hydrate, solvate, polymorph, co-crystal, tautomer, stereoisomer, isotopically labeled derivative, or prodrug thereof, wherein:

A is a group comprising a nucleic acid as described herein (e.g., an oligonucleotide or mRNA);

X is O or S;

each of $L^1$, $L^2$, and $L^3$ is independently a bond, optionally substituted alkylene, or optionally substituted heteroalkylene;

n is an integer from 1 to 10, inclusive;

each instance of $R^N$ is independently hydrogen, optionally substituted alkyl; optionally substituted acyl; or a nitrogen protecting group;

each instance of $R^O$ is independently hydrogen, optionally substituted alkyl, optionally substituted acyl; or an oxygen protecting group.

In certain embodiments, n is an integer from 2-10, inclusive. In certain embodiments, n is an integer from 2-5, inclusive. In certain embodiments, n is 4.

A compound of Formula (I) can be of any one of the following formulae, or a mixture of two or more thereof:

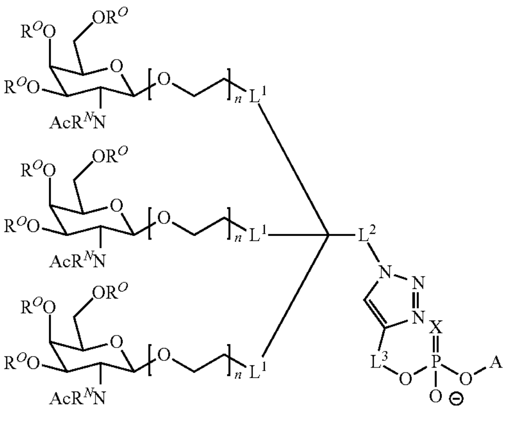

-continued

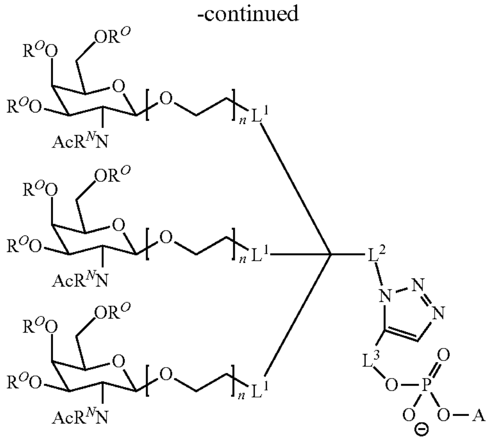

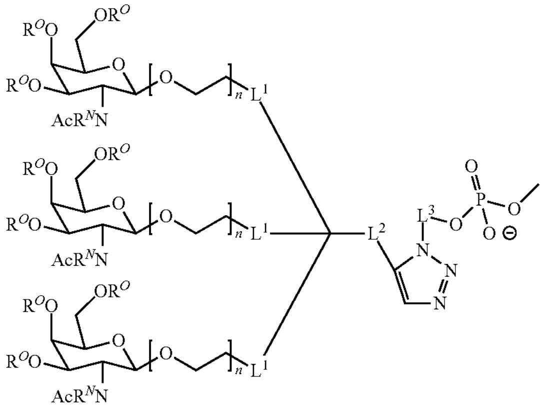

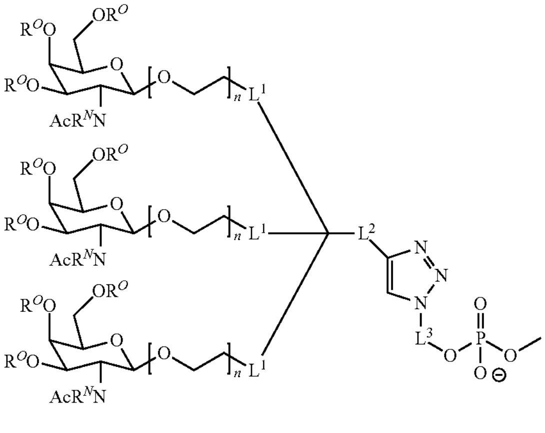

In an embodiment, the conjugate of Formula (V) is of Formula (V-a):

(V-a)

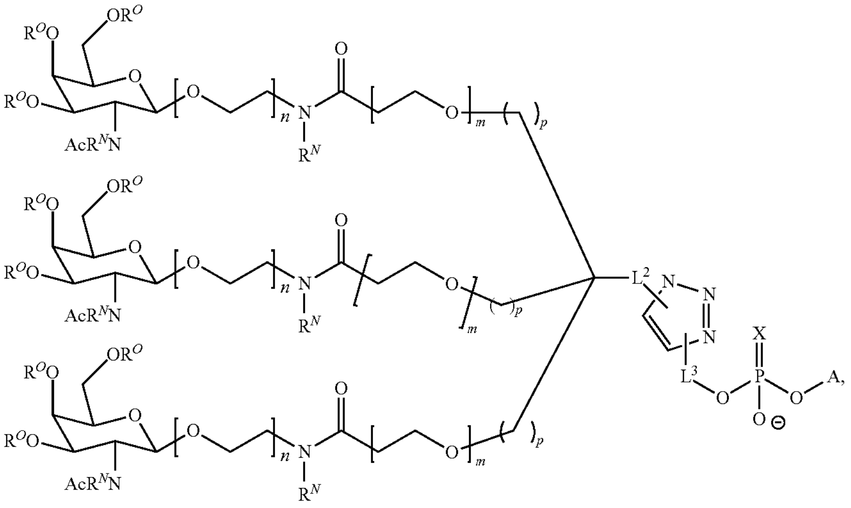

or a pharmaceutically acceptable salt, hydrate, solvate, polymorph, co-crystal, tautomer, stereoisomer, isotopically labeled derivative, or prodrug thereof, wherein:

m is an integer from 0 to 10, inclusive; and p is an integer from 0 to 10, inclusive.

In an embodiment, the conjugate of Formula (V-a) is of Formula (V-b):

(V-b)

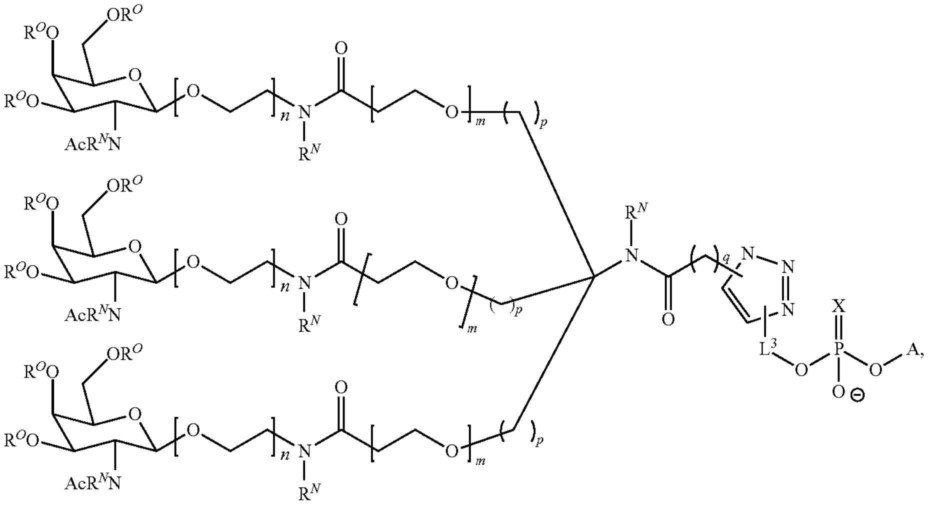

or a pharmaceutically acceptable salt, hydrate, solvate, polymorph, co-crystal, tautomer, stereoisomer, isotopically labeled derivative, or prodrug thereof, wherein:

q is an integer from 0 to 20, inclusive.

In an embodiment, the conjugate of Formula (V-b) is of Formula (V-c):

(V-c)

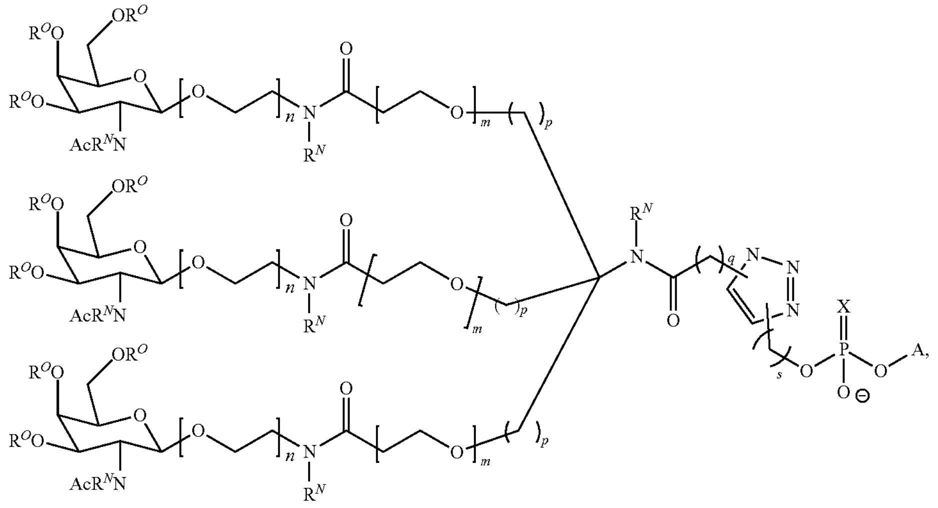

or a pharmaceutically acceptable salt, hydrate, solvate, polymorph, co-crystal, tautomer, stereoisomer, isotopically labeled derivative, or prodrug thereof, wherein: s is an integer from 0 to 20, inclusive.

In an embodiment, the conjugate of Formula (V-c) is of Formula (V-d):

(V-d)

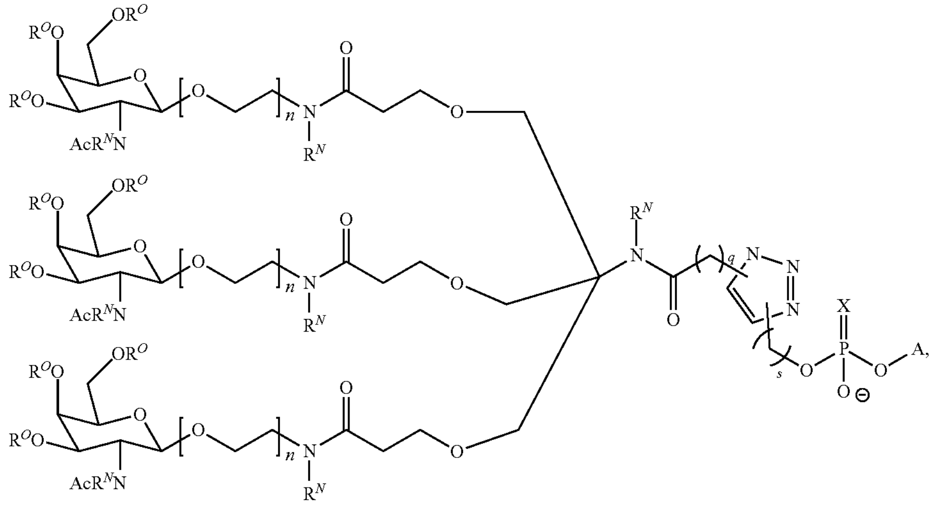

or a pharmaceutically acceptable salt, hydrate, solvate, polymorph, co-crystal, tautomer, stereoisomer, isotopically labeled derivative, or prodrug thereof.

In an embodiment, the conjugate of Formula (V-d) is of Formula (V-e):

(V-e)

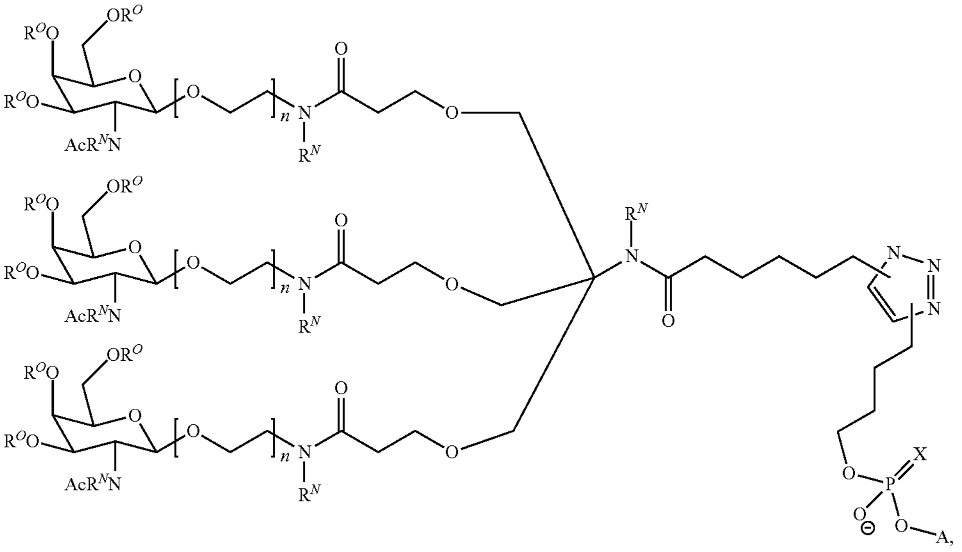

or a pharmaceutically acceptable salt, hydrate, solvate, polymorph, co-crystal, tautomer, stereoisomer, isotopically labeled derivative, or prodrug thereof.

In an embodiment, the conjugate of Formula (V-e) is of Formula (V-f):

(V-f)

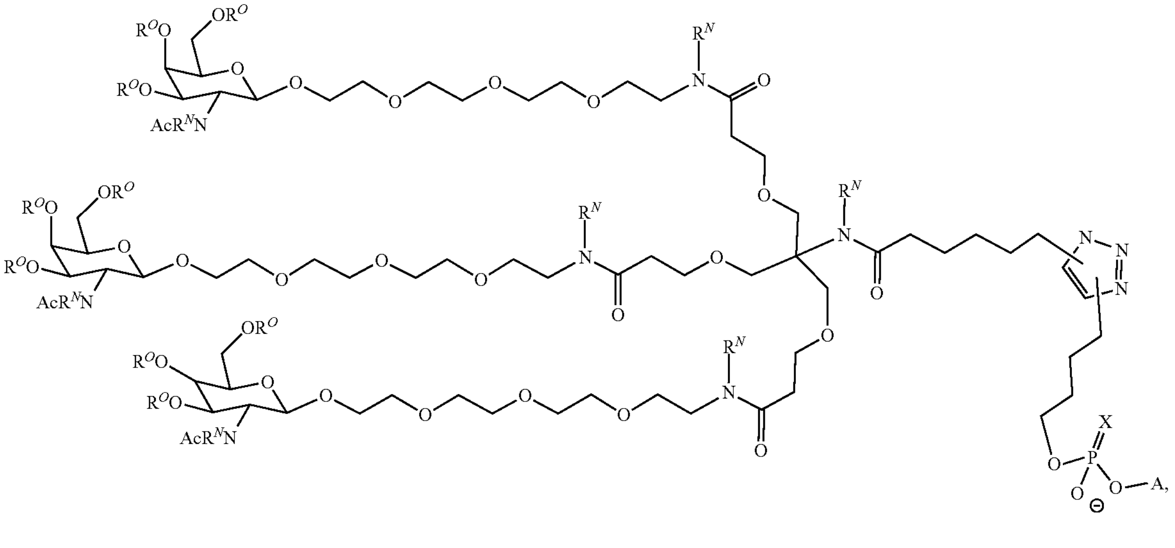

or a pharmaceutically acceptable salt, hydrate, solvate, polymorph, co-crystal, tautomer, stereoisomer, isotopically labeled derivative, or prodrug thereof.

In an embodiment, the conjugate of Formula (V-f) is of Formula (V-g):

(V-g)

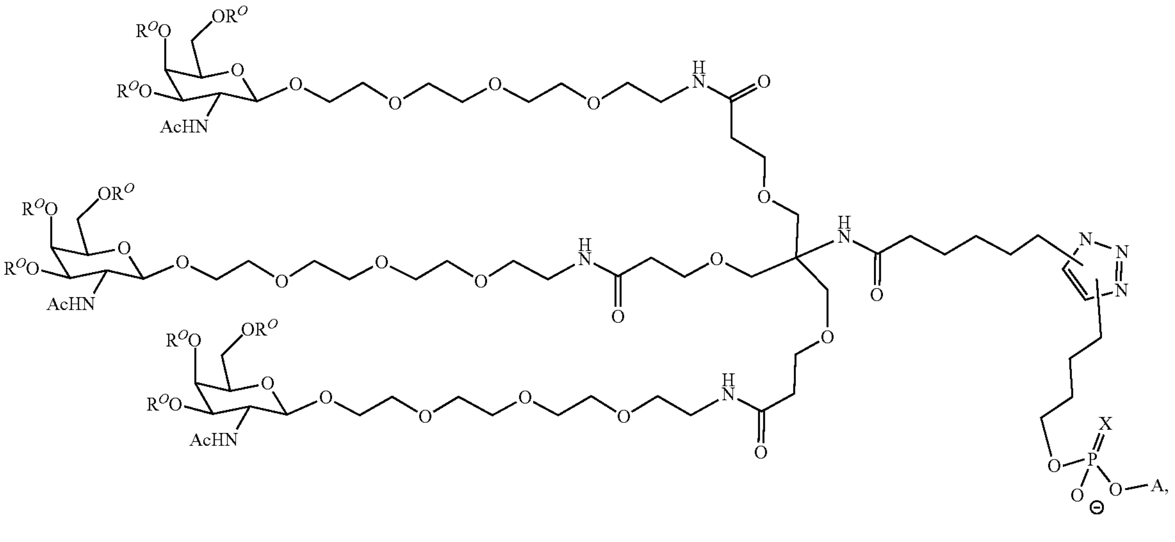

or a pharmaceutically acceptable salt, hydrate, solvate, polymorph, co-crystal, tautomer, stereoisomer, isotopically labeled derivative, or prodrug thereof.

In an embodiment, the conjugate of Formula (V-g) is of Formula (V-h):

(V-h)

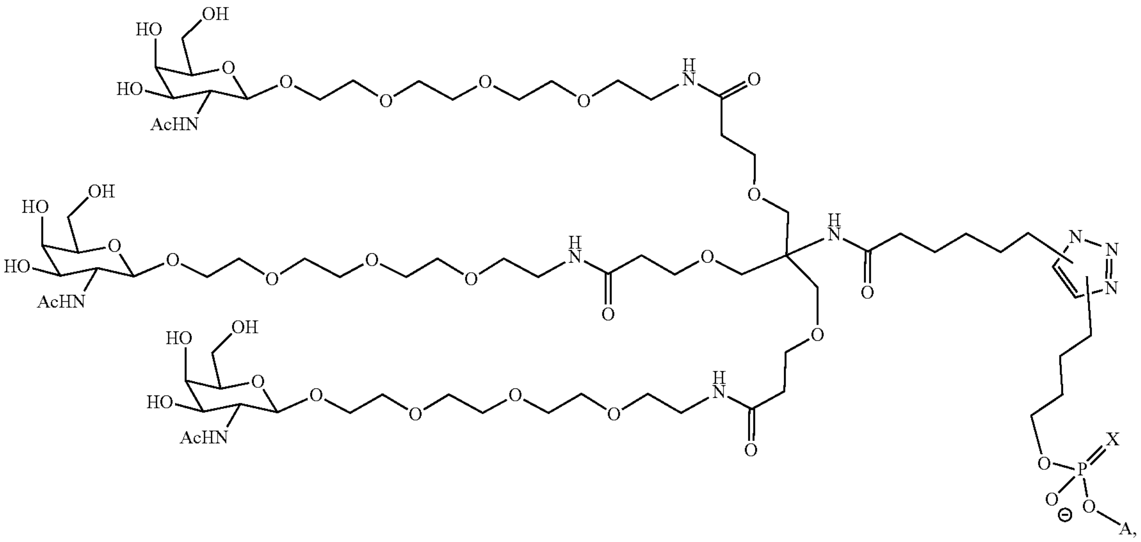

or a pharmaceutically acceptable salt, hydrate, solvate, polymorph, co-crystal, tautomer, stereoisomer, isotopically labeled derivative, or prodrug thereof.

In an embodiment, the conjugate of Formula (I) is of one of the following formulae, or a mixture of two or more thereof:

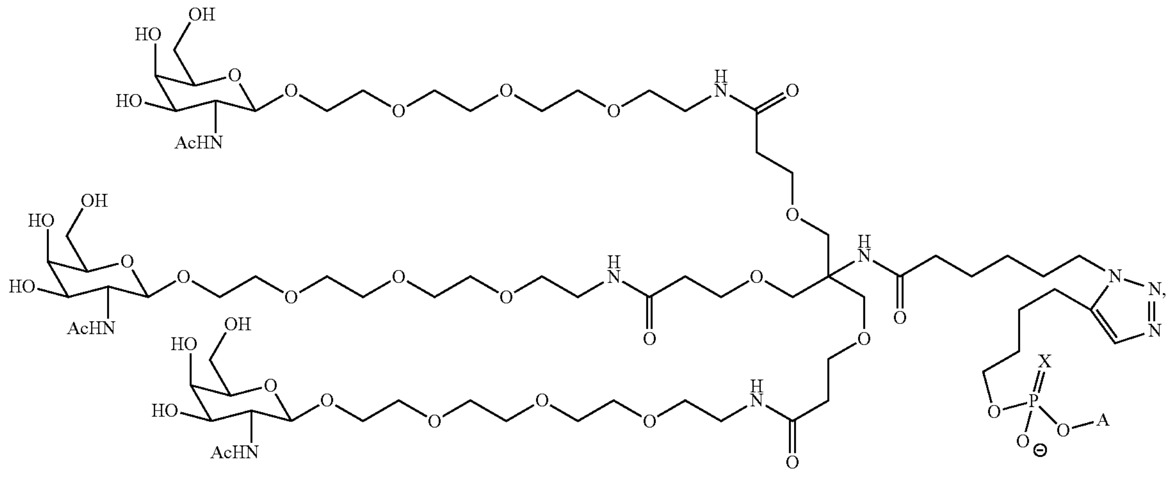
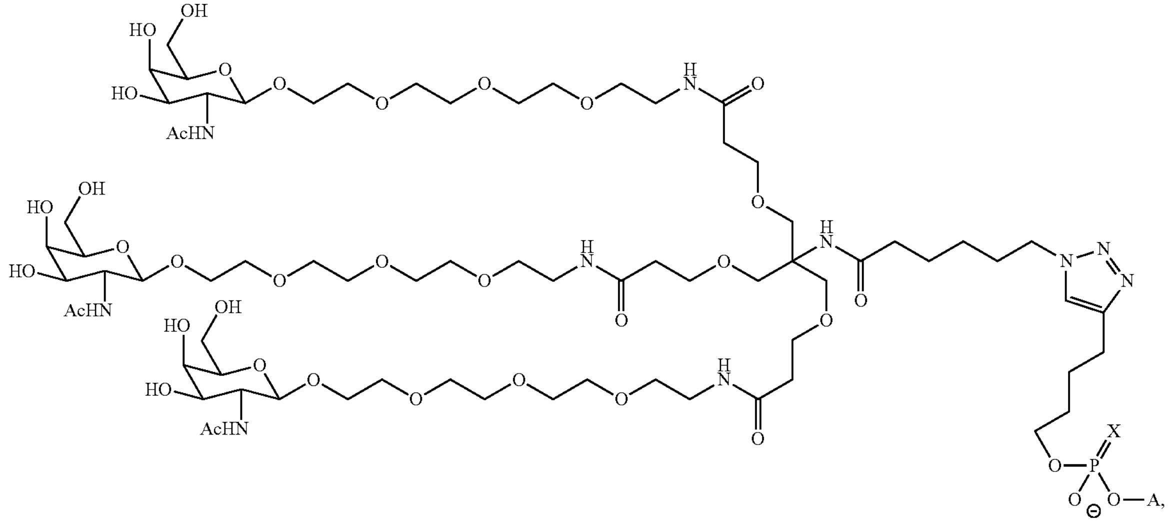
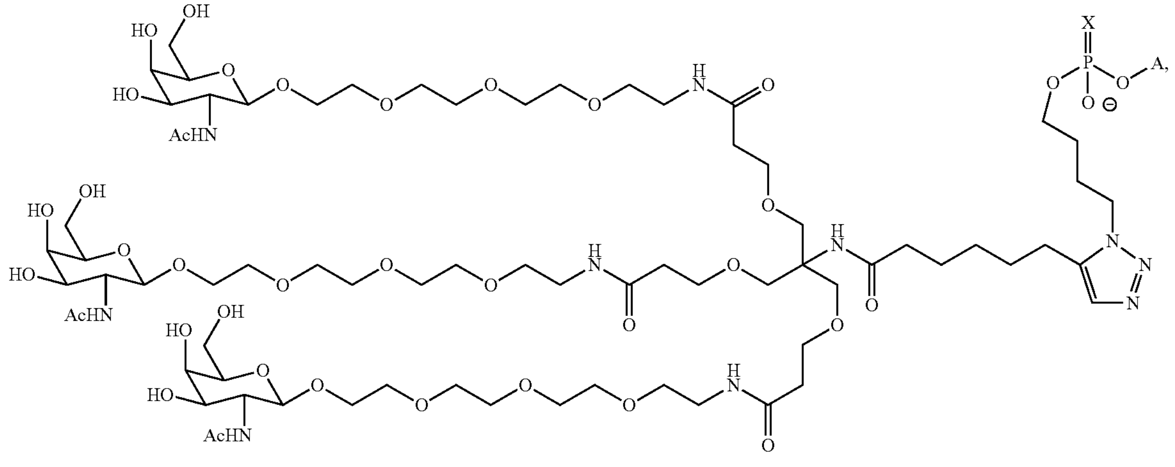

-continued
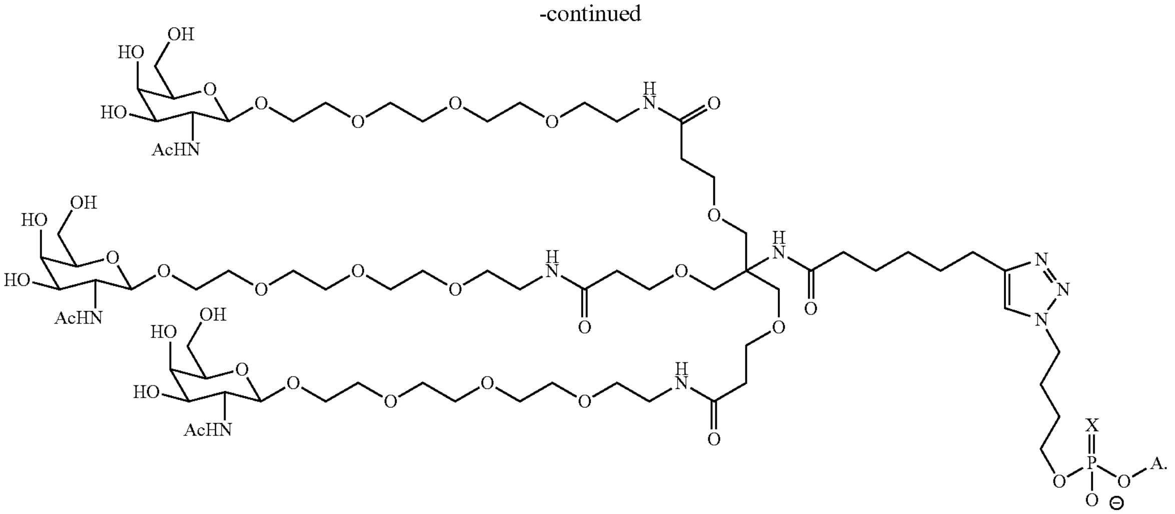
In an embodiment, the conjugate of Formula (V-h) is of Formula (V-i):
(V-i)
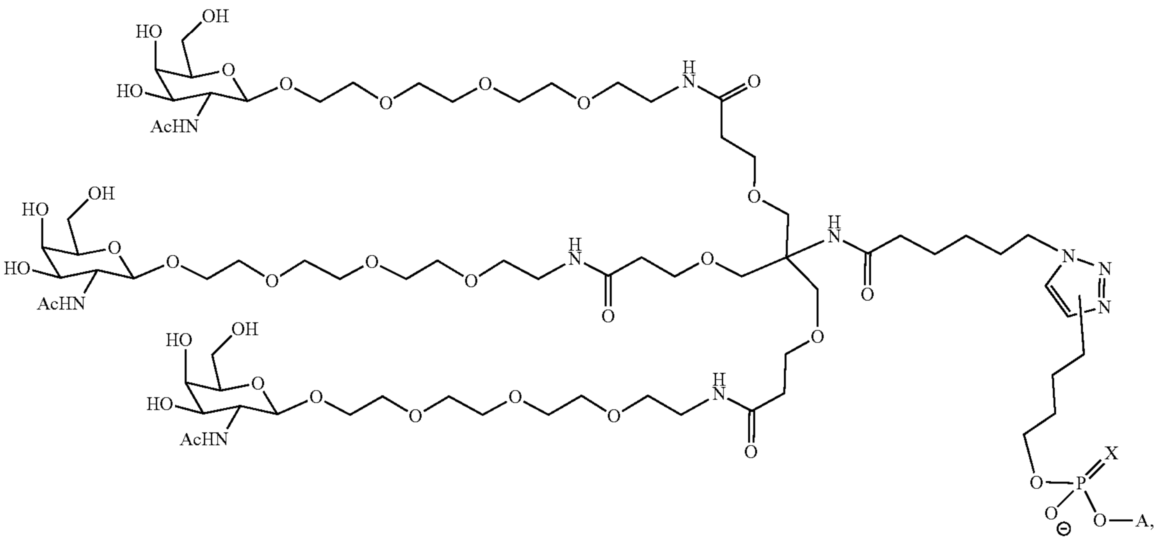
or a pharmaceutically acceptable salt, hydrate, solvate, polymorph, co-crystal, tautomer, stereoisomer, isotopically labeled derivative, or prodrug thereof.
In an embodiment, the conjugate of Formula (V-i) is of the following formula:

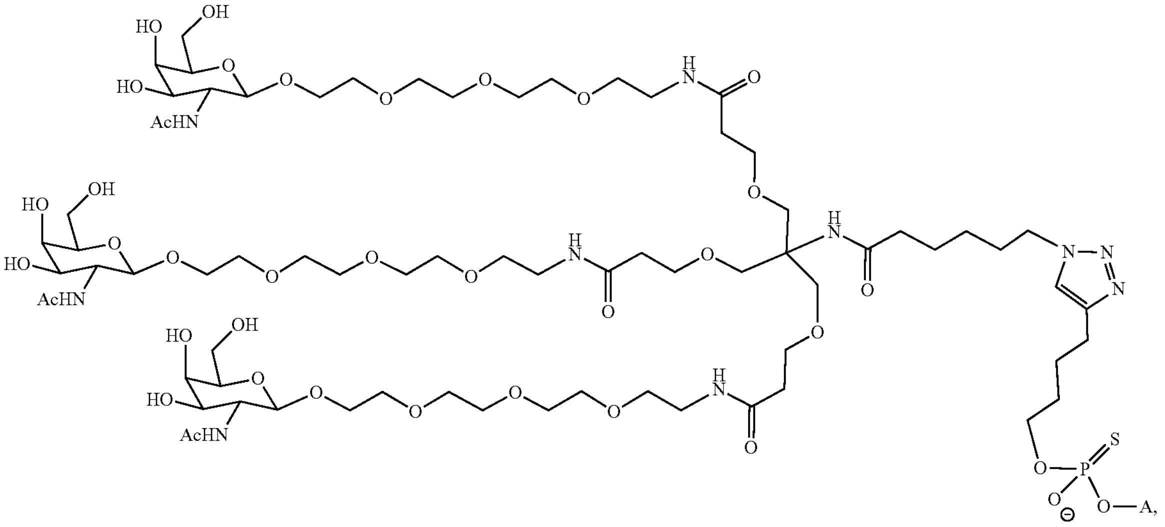

or a pharmaceutically acceptable salt, hydrate, solvate, polymorph, co-crystal, tautomer, stereoisomer, isotopically labeled derivative, or prodrug thereof.

In an embodiment, the conjugate of Formula (V-a) is of Formula (V-j):

(V-j)

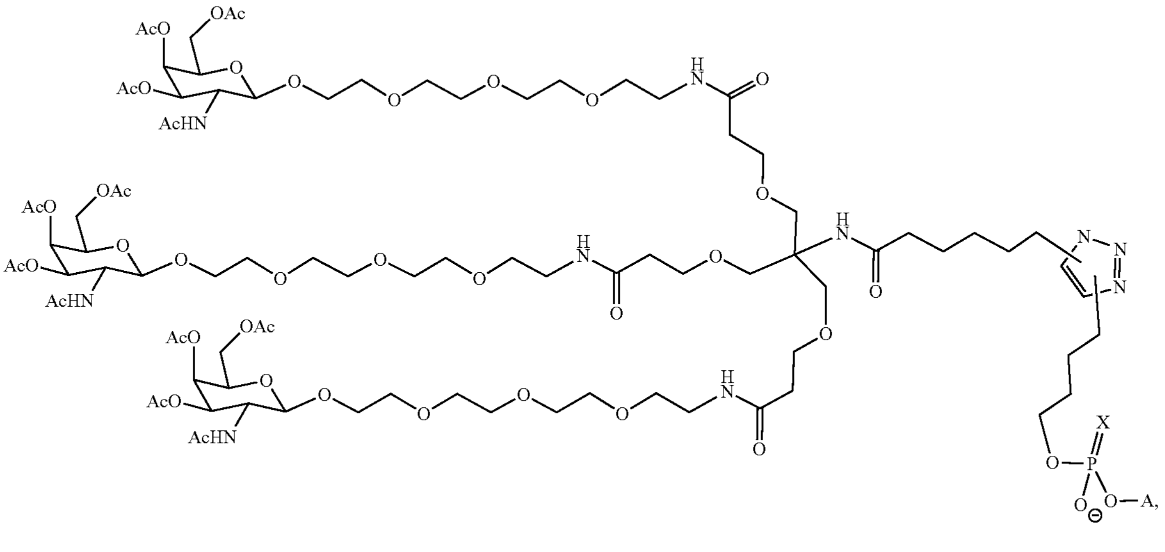

or a pharmaceutically acceptable salt, hydrate, solvate, polymorph, co-crystal, tautomer, stereoisomer, isotopically labeled derivative, or prodrug thereof.

In certain embodiments, the conjugate of Formula (V-a) is of Formula (V-k):

(V-k)

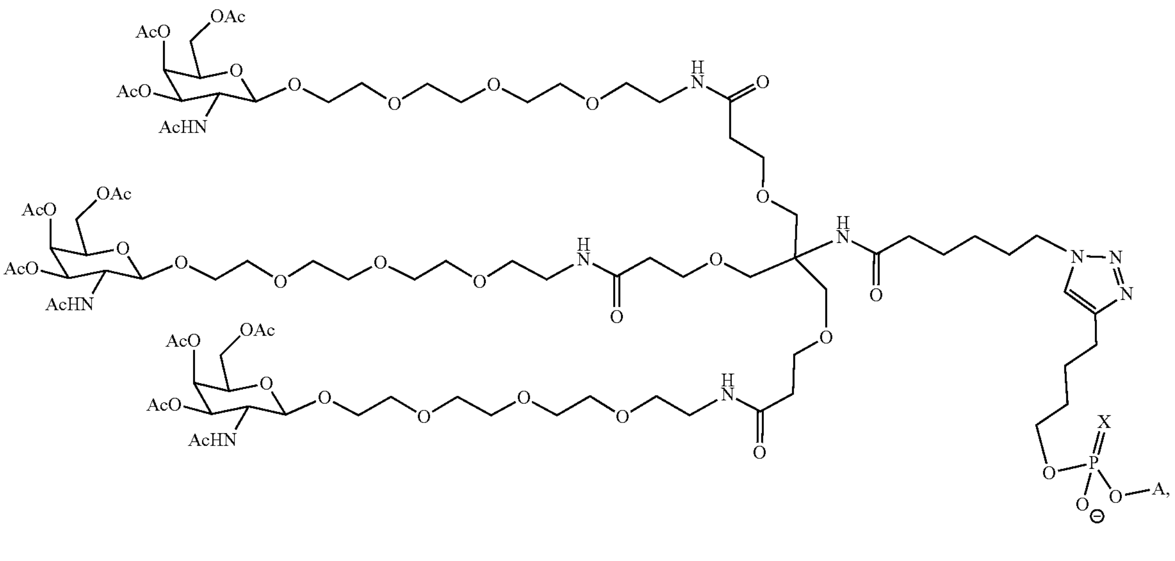

or a pharmaceutically acceptable salt, hydrate, solvate, polymorph, co-crystal, tautomer, stereoisomer, isotopically labeled derivative, or prodrug thereof.

In an embodiment, the conjugate of Formula (V-k) is of the following formula:

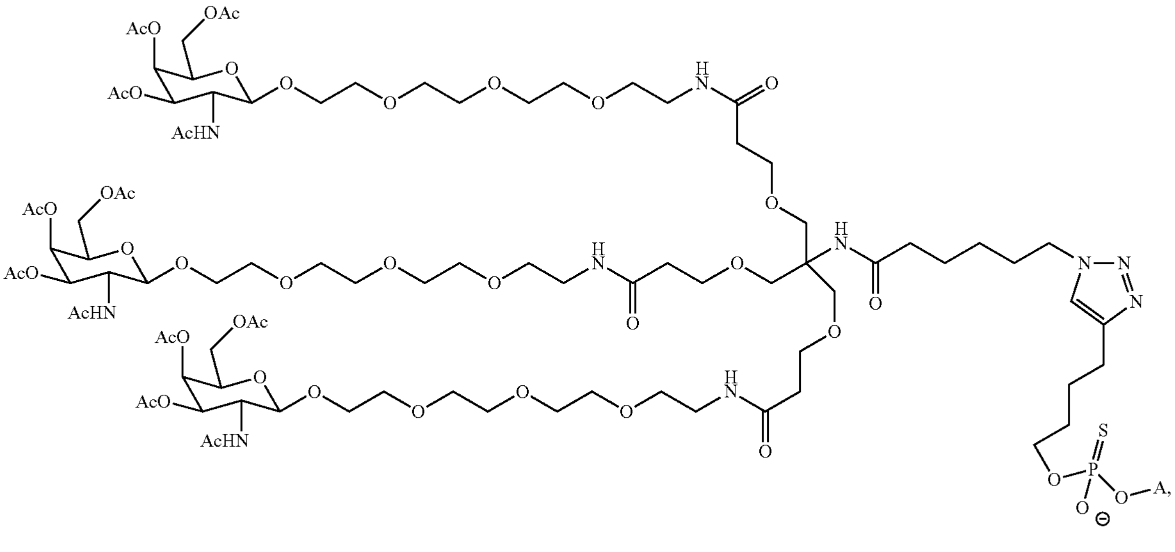

or a pharmaceutically acceptable salt, hydrate, solvate, polymorph, co-crystal, tautomer, stereoisomer, isotopically labeled derivative, or prodrug thereof.

The present invention provides compounds comprising targeting moieties (e.g., a sugar, a folate, or a cell-penetrating peptide) for the delivery of therapeutic agents. In certain embodiments, the compound is a nucleic acid as described herein (e.g., an oligonucleotide or mRNA). However, in other embodiments, the compound may be a therapeutic agent other than a nucleic acid as described herein. Examples of other therapeutic agents include, but are not limited to, small molecules such as drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, lipids, hormones, and vitamins.

Accordingly, the present invention provides compounds (e.g., nucleic acids as described herein, such oligonucleotides or mRNAs, or other agents) comprising groups of Formula (VI):

(VI)

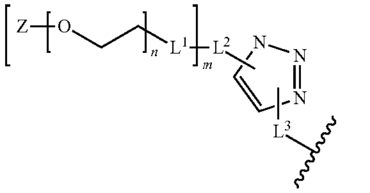

wherein Z is a sugar, a folate, or a cell-penetrating peptide; each of $L^1$, $L^2$, and $L^3$ is independently a bond, optionally substituted alkylene, or optionally substituted heteroalkylene; wherein each $L^1$ optionally comprises a triazole; m is an integer from 3 to 10, inclusive; and n is an integer from 1 to 10, inclusive.

In an embodiment, the compound is of Formula (VI-a):

(VI-a)

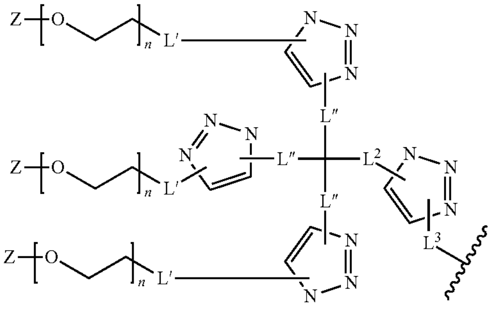

wherein each of L' and L" is independently a bond, optionally substituted alkylene, or optionally substituted heteroalkylene.

In an embodiment, the compound is of Formula (VII):

(VII)

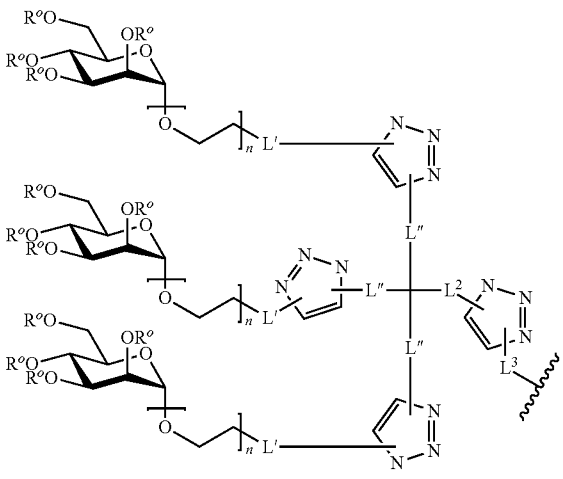

wherein each instance of $R^O$ is independently hydrogen, optionally substituted alkyl, optionally substituted acyl, or an oxygen protecting group.

In an embodiment, the compound is of Formula (VII-a):

(VII-a)

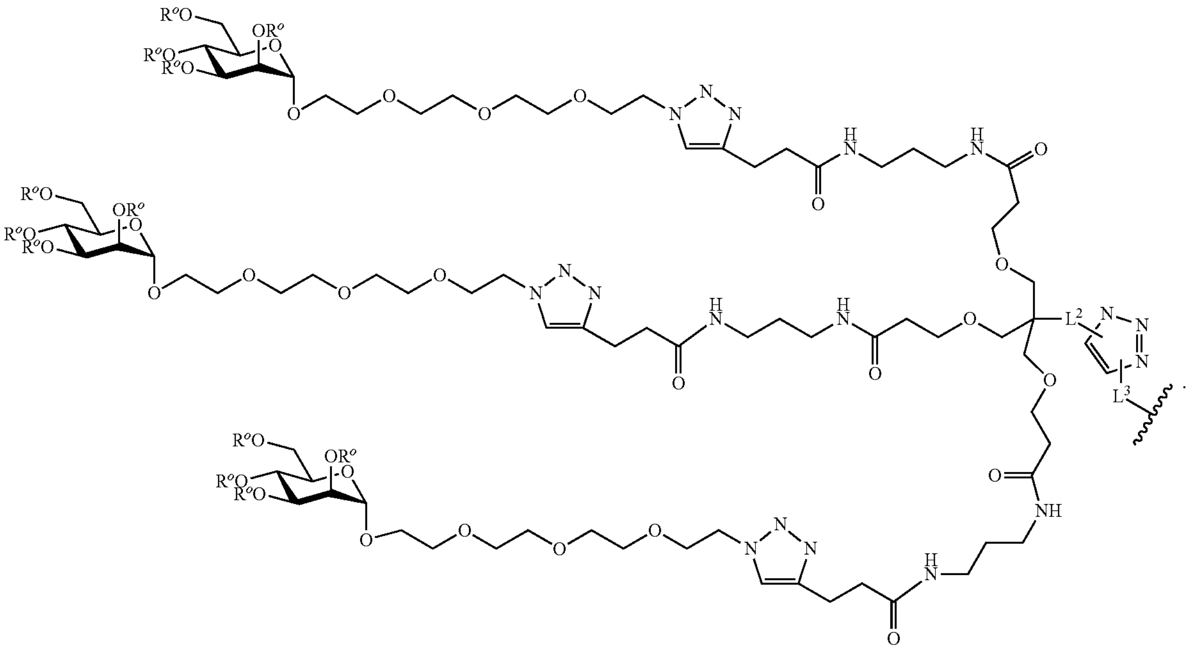

In an embodiment, the compound is of Formula (VII-b):
(VII-b)
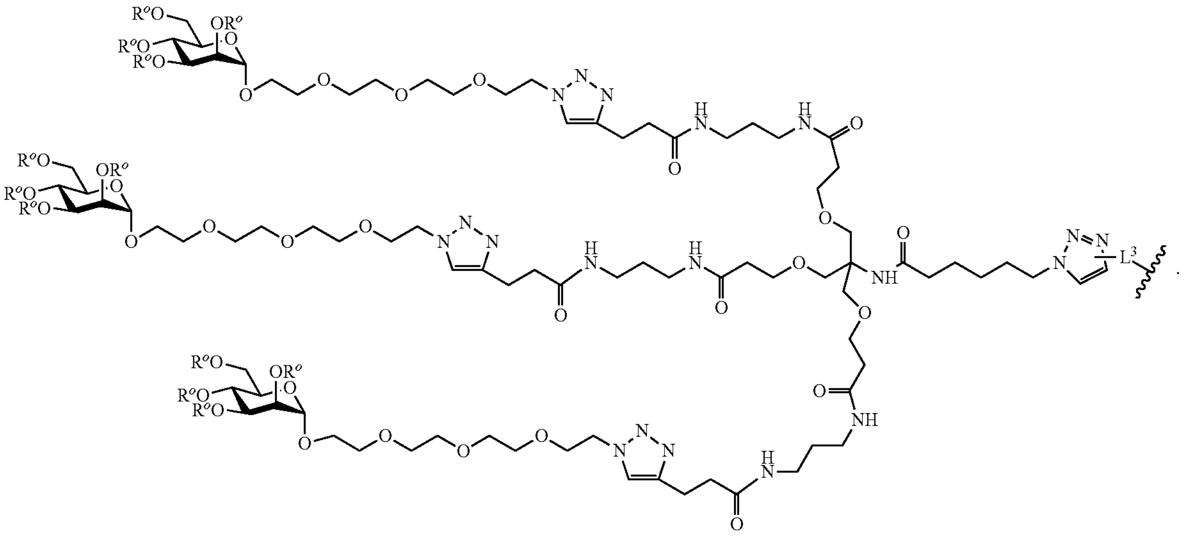
In an embodiment, the compound is of Formula (VII-c):
(VII-c)
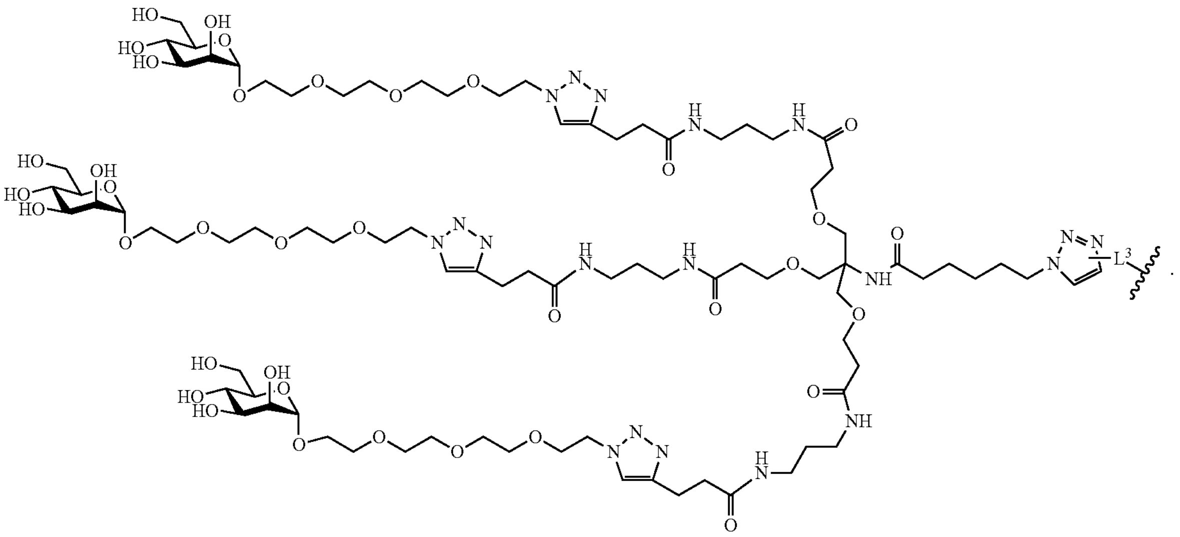

In an embodiment, the compound is of the following formula

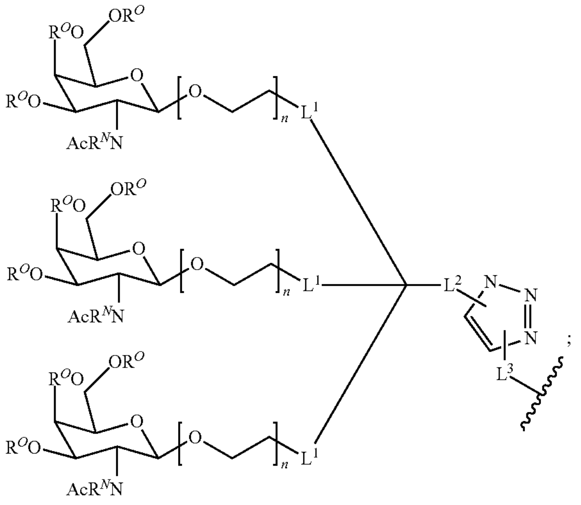

and pharmaceutically acceptable salts, hydrates, solvates, polymorphs, co-crystals, tautomers, stereoisomers, isotopically labeled derivatives, and prodrugs thereof, wherein:

each of $L^1$, $L^2$, and $L^3$ is independently a bond, optionally substituted alkylene, or optionally substituted heteroalkylene;

n is an integer from 1 to 10, inclusive;

each instance of $R^N$ is independently hydrogen, optionally substituted alkyl; optionally substituted acyl; or a nitrogen protecting group;

each instance of $R^O$ is independently hydrogen, optionally substituted alkyl, optionally substituted acyl; or an oxygen protecting group.

A compound of the present invention can comprise any one of the following groups, or be a mixture of two or more compounds comprising any of the following groups:

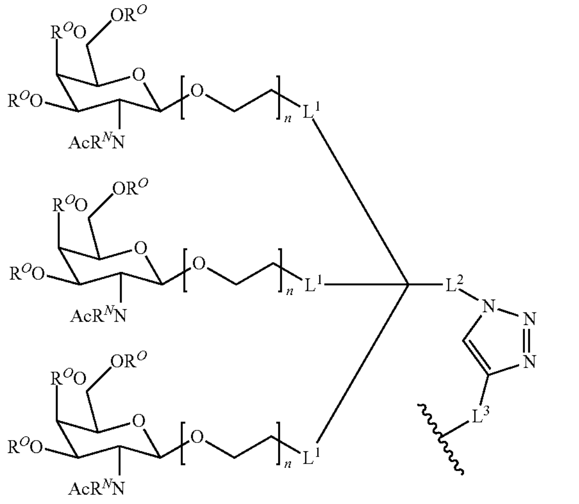

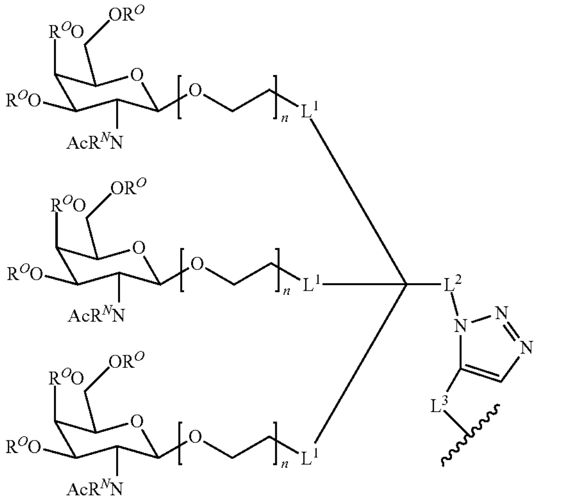

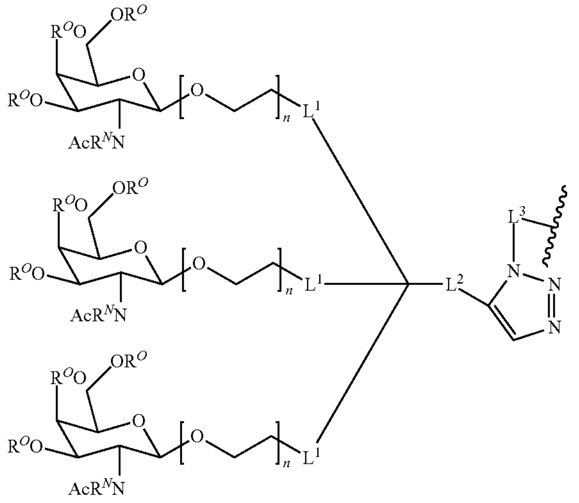

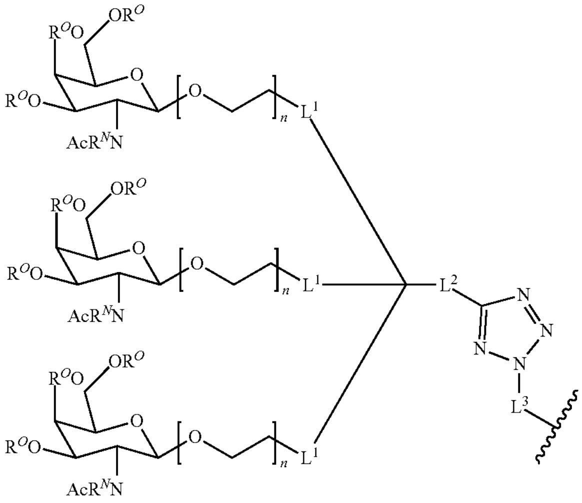

In certain embodiments, n is 4; and a compound (e.g., a nucleic acid as described herein such as an oligonucleotide or mRNA) of the present invention comprises a group of the following formula:

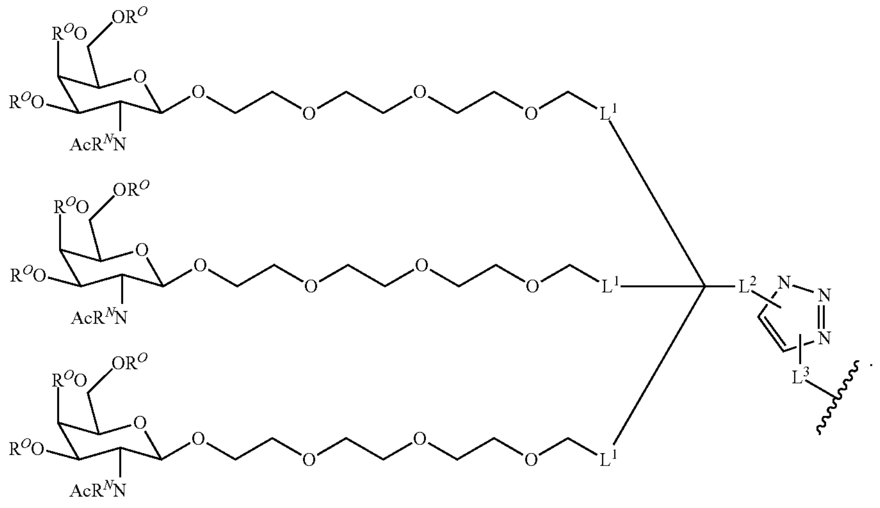

In certain embodiments, n is 4; and a compound (e.g., a nucleic acid as described herein such as an oligonucleotide or mRNA) of the present invention comprises a group of the following formula:

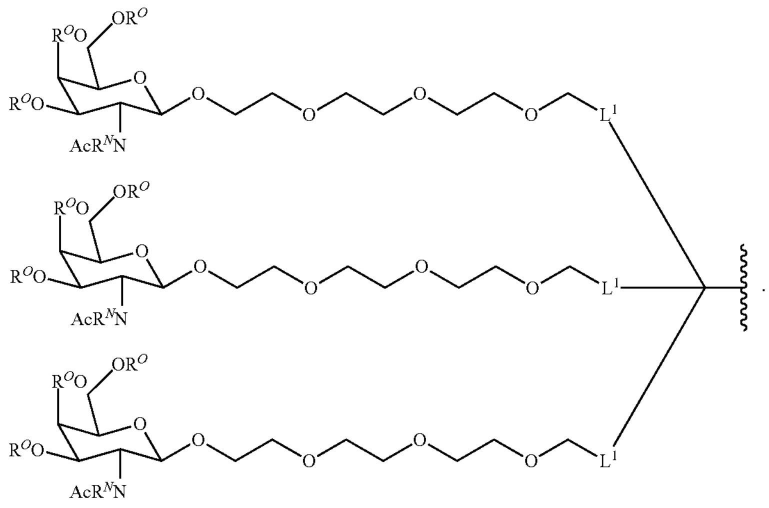

In certain embodiments, a compound (e.g., a nucleic acid as described herein such as an oligonucleotide or mRNA) provided herein comprises a group of the following formula:

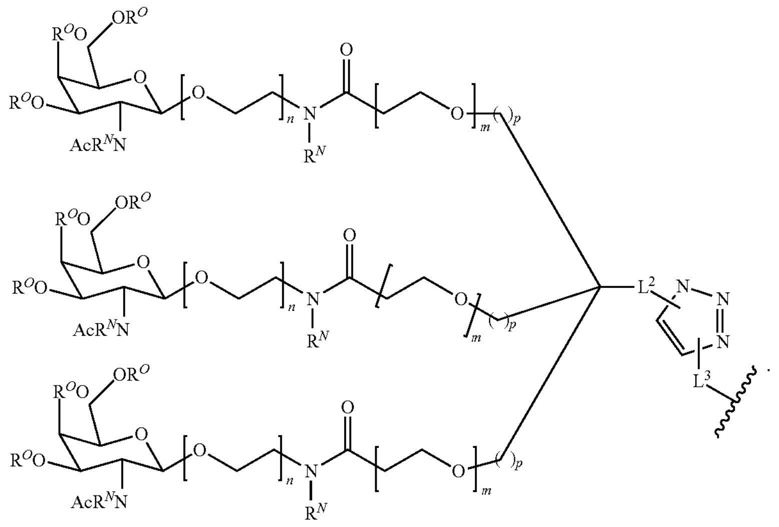

In certain embodiments, n is 4; and a compound (e.g., a nucleic acid as described herein such as an oligonucleotide or mRNA) of the present invention comprises a group of the following formula:

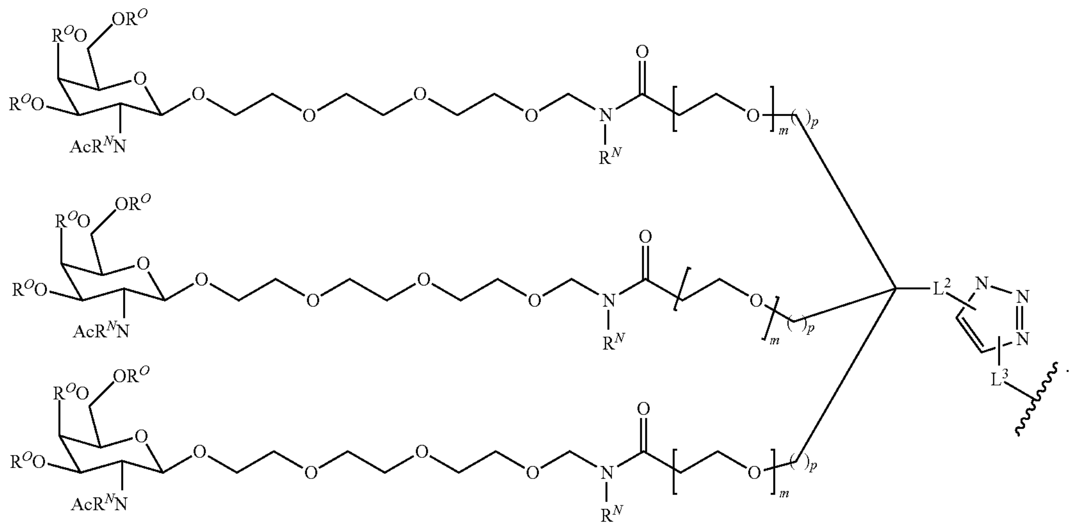

In certain embodiments, n is 4; and a compound (e.g., a nucleic acid as described herein such as an oligonucleotide or mRNA) of the present invention comprises a group of the following formula:

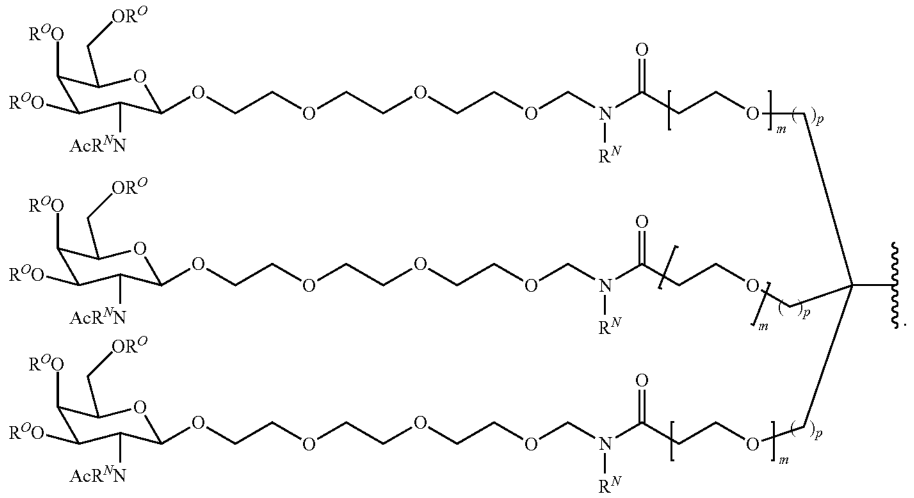
In certain embodiments, a compound (e.g., a nucleic acid as described herein such as an oligonucleotide or mRNA) provided herein comprises a group of the following formula:
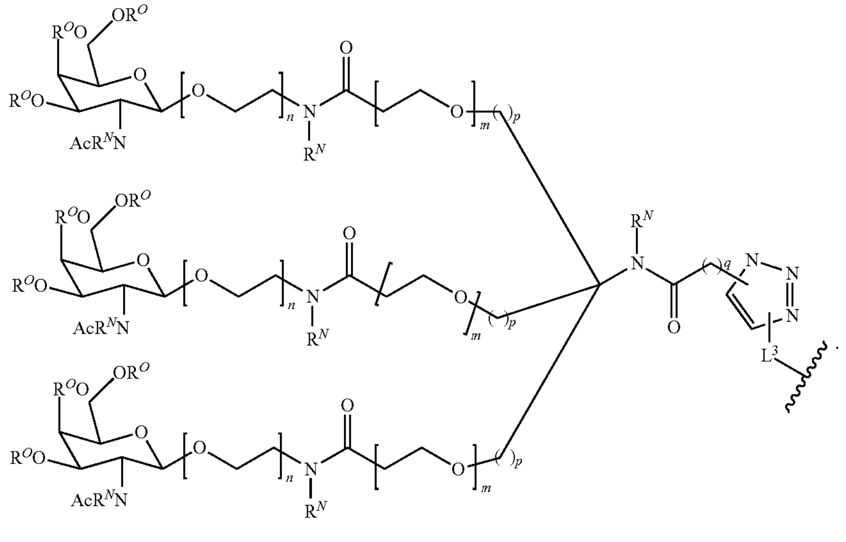
In certain embodiments, a compound (e.g., a nucleic acid as described herein such as an oligonucleotide or mRNA) provided herein comprises a group of the following formula:

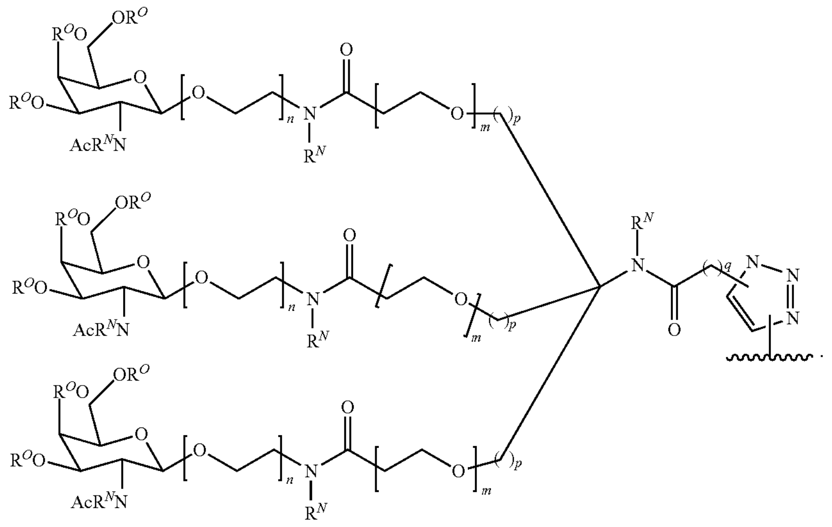
In certain embodiments, a compound (e.g., a nucleic acid as described herein such as an oligonucleotide or mRNA) provided herein comprises a group of the following formula:
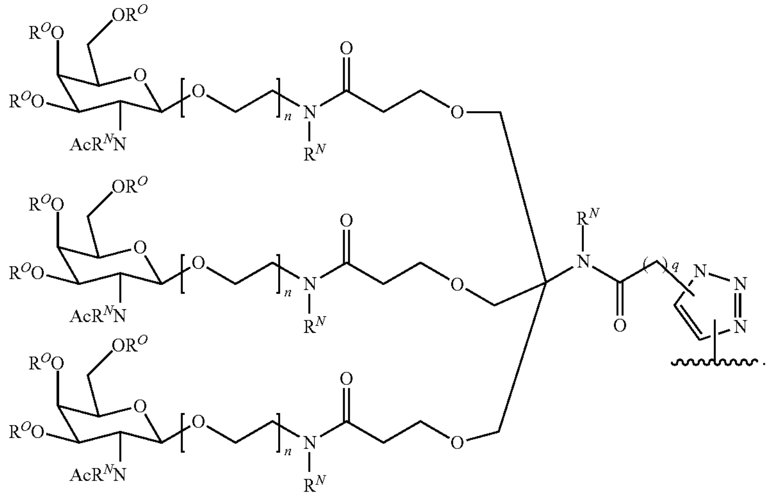
In certain embodiments, a compound (e.g., a nucleic acid as described herein such as an oligonucleotide or mRNA) provided herein comprises a group of the following formula:

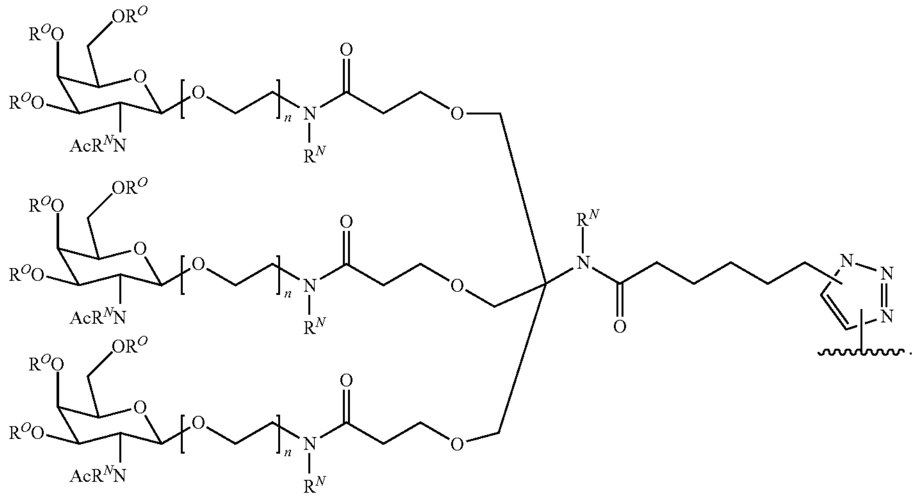
In certain embodiments, a compound (e.g., a nucleic acid as described herein such as an oligonucleotide or mRNA) provided herein comprises a group of the following formula:
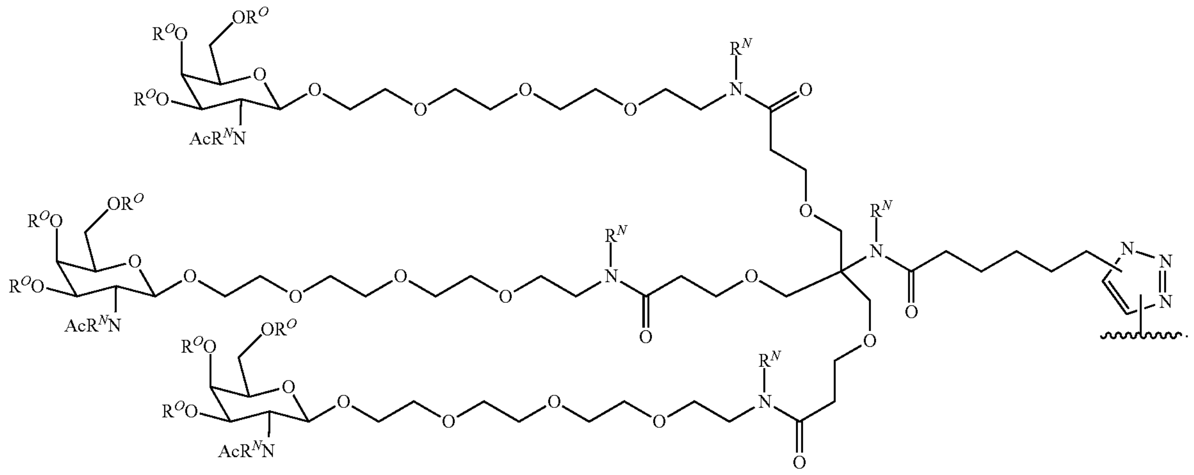
In certain embodiments, a compound (e.g., a nucleic acid as described herein such as an oligonucleotide or mRNA) provided herein comprises a group of the following formula:

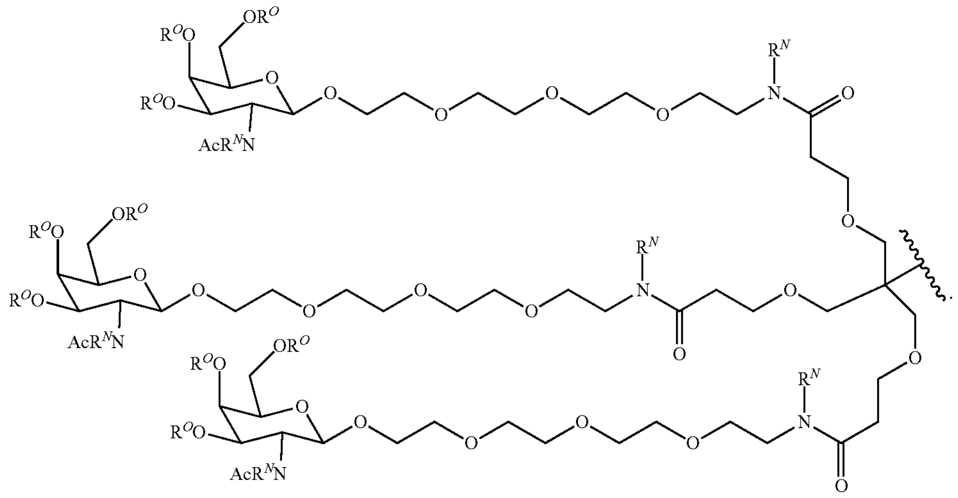
In certain embodiments, a compound (e.g., a nucleic acid as described herein such as an oligonucleotide or mRNA) provided herein comprises a group of the following formula:
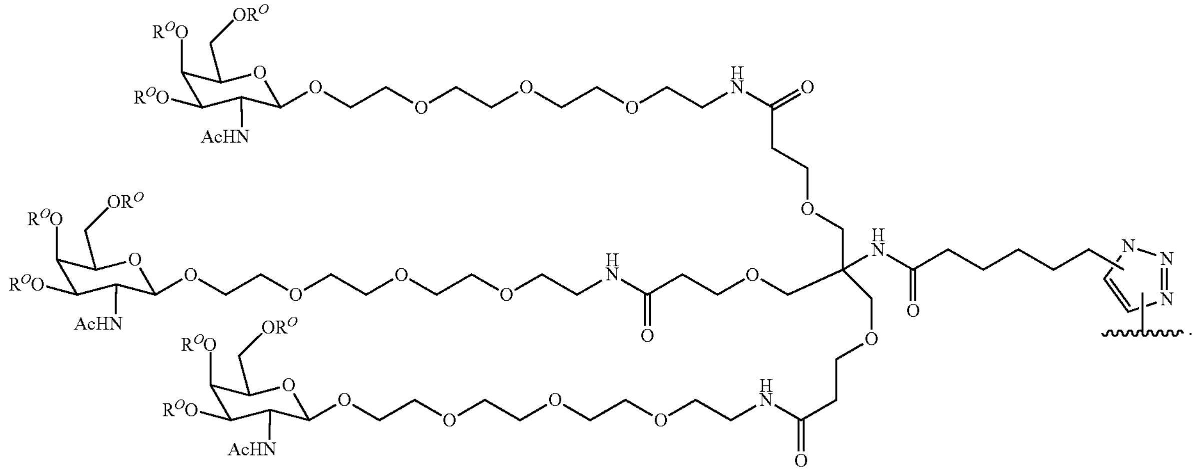
In certain embodiments, a compound (e.g., a nucleic acid as described herein such as an oligonucleotide or mRNA) provided herein comprises a group of the following formula:

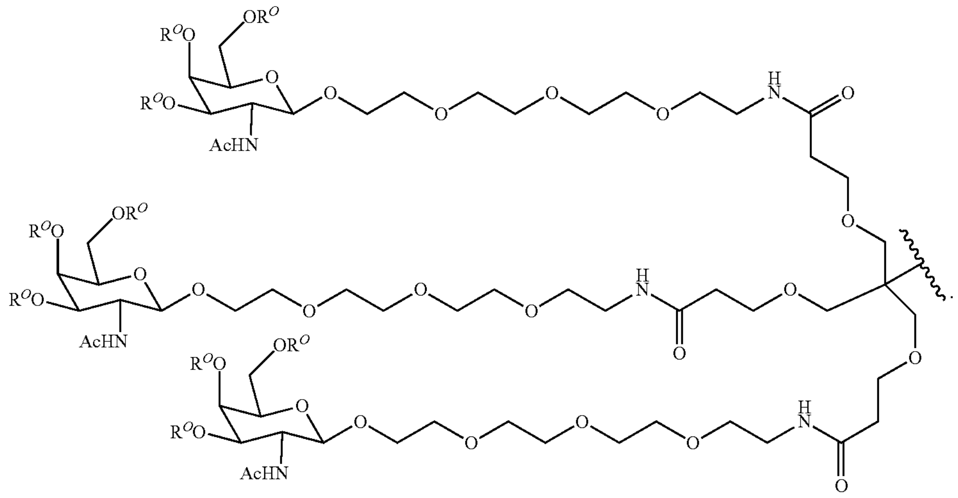
In certain embodiments, a compound (e.g., a nucleic acid as described herein such as an oligonucleotide or mRNA) provided herein comprises a group of the following formula:
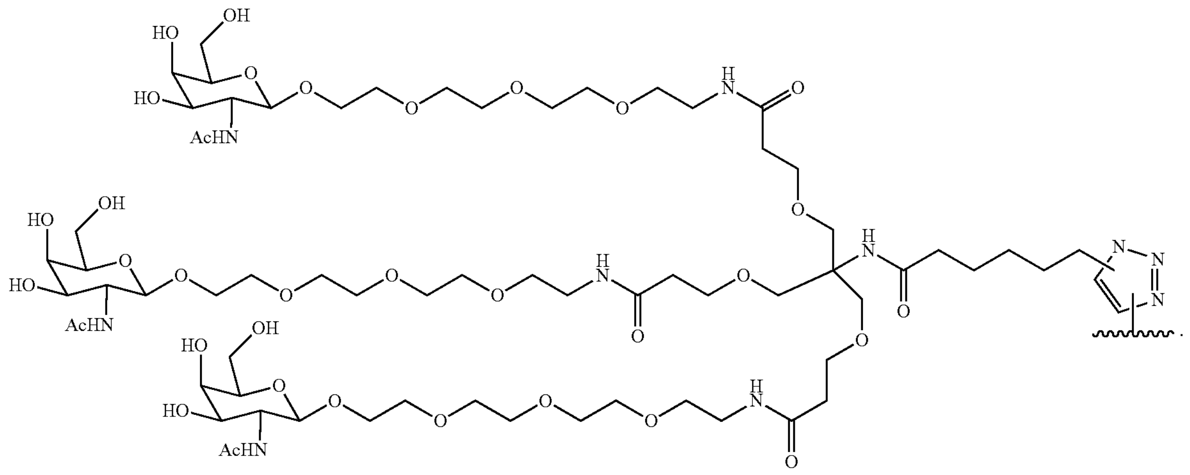
In certain embodiments, a compound (e.g., a nucleic acid as described herein such as an oligonucleotide or mRNA) provided herein comprises a group of the following formula:

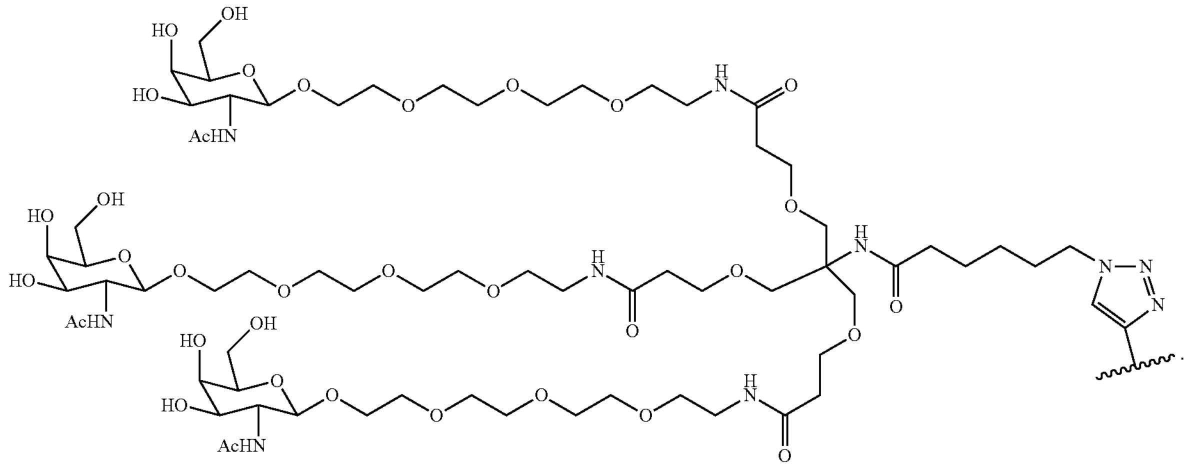 [SMILES: *c1cn(CCCCCC(=O)NC(COCCC(=O)NCCOCCOCCOCCOC2OC(CO)C(O)C(O)C2NC(C)=O)(COCCC(=O)NCCOCCOCCOCCOC2OC(CO)C(O)C(O)C2NC(C)=O)COCCC(=O)NCCOCCOCCOCCOC2OC(CO)C(O)C(O)C2NC(C)=O)nn1]
In certain embodiments, a compound (e.g., a nucleic acid as described herein such as an oligonucleotide or mRNA) provided herein comprises a group of the following formula:
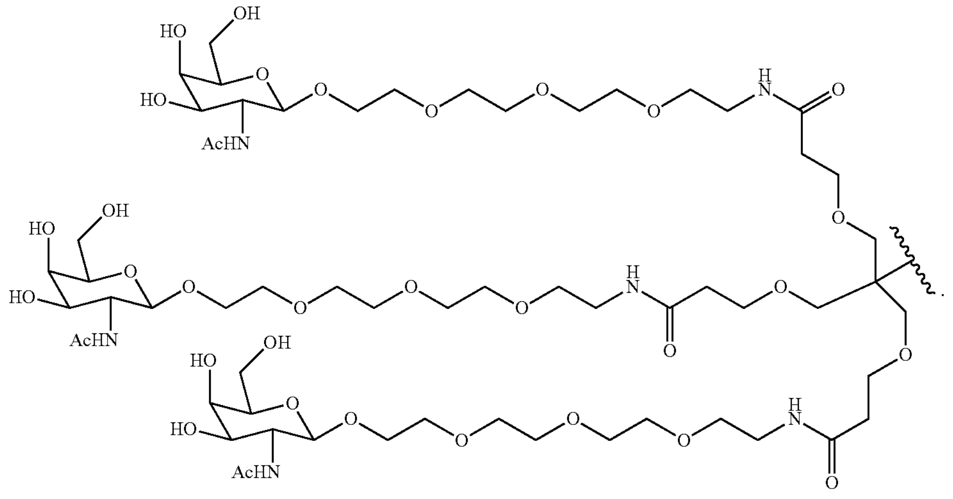 [SMILES: *C(COCCC(=O)NCCOCCOCCOCCOC1OC(CO)C(O)C(O)C1NC(C)=O)(COCCC(=O)NCCOCCOCCOCCOC1OC(CO)C(O)C(O)C1NC(C)=O)COCCC(=O)NCCOCCOCCOCCOC1OC(CO)C(O)C(O)C1NC(C)=O]
In certain embodiments, a compound (e.g., a nucleic acid as described herein such as an oligonucleotide or mRNA) provided herein comprises a group of the following formula:

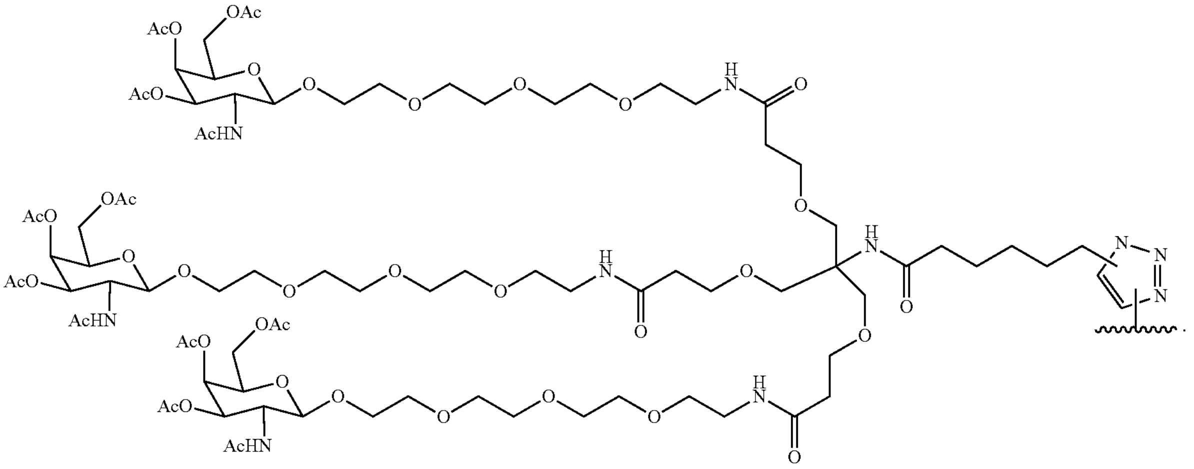
In certain embodiments, a compound (e.g., a nucleic acid as described herein such as an oligonucleotide or mRNA) provided herein comprises a group of the following formula:
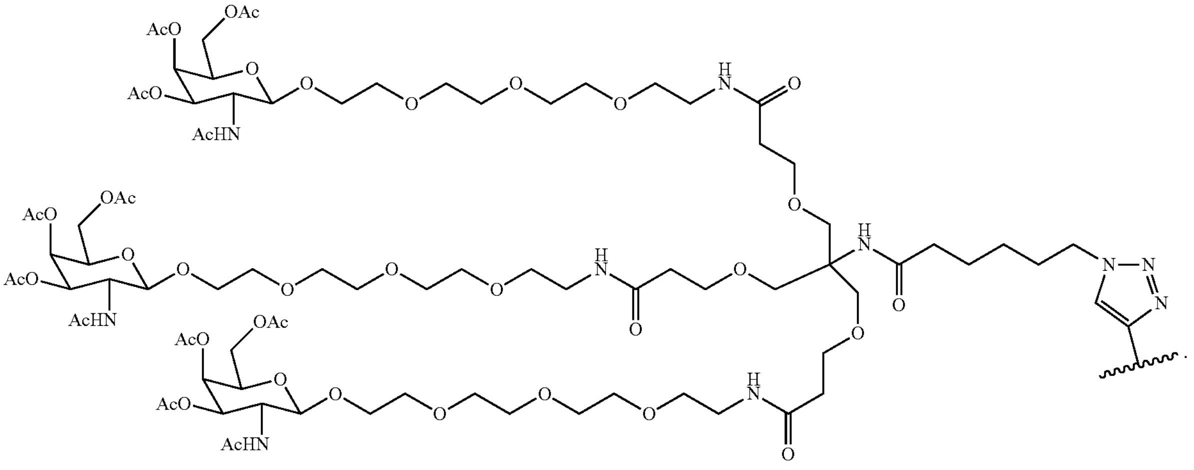 [SMILES: *c1cn(CCCCCC(=O)NC(COCCC(=O)NCCOCCOCCOCCOC2OC(COC(C)=O)C(OC(C)=O)C(OC(C)=O)C2NC(C)=O)(COCCC(=O)NCCOCCOCCOCCOC2OC(COC(C)=O)C(OC(C)=O)C(OC(C)=O)C2NC(C)=O)COCCC(=O)NCCOCCOCCOCCOC2OC(COC(C)=O)C(OC(C)=O)C(OC(C)=O)C2NC(C)=O)nn1]
In certain embodiments, a compound (e.g., a nucleic acid as described herein such as an oligonucleotide or mRNA) provided herein comprises a group of the following formula:

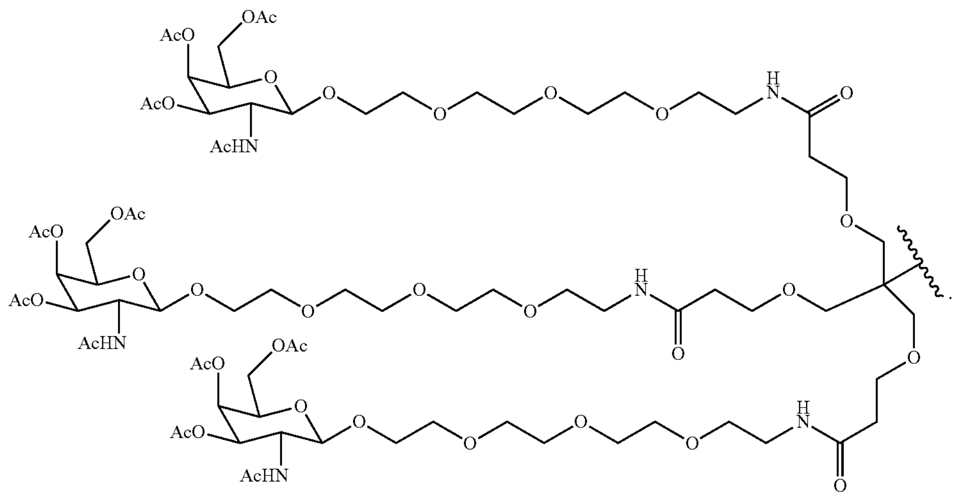 [SMILES: *C(COCCC(=O)NCCOCCOCCOCCOC1OC(COC(C)=O)C(OC(C)=O)C(OC(C)=O)C1NC(C)=O)(COCCC(=O)NCCOCCOCCOCCOC1OC(COC(C)=O)C(OC(C)=O)C(OC(C)=O)C1NC(C)=O)COCCC(=O)NCCOCCOCCOCCOC1OC(COC(C)=O)C(OC(C)=O)C(OC(C)=O)C1NC(C)=O]

Methods of Preparing Conjugates and Compounds

In another aspect, the present invention provides methods for preparing the conjugates and compounds described herein. It should be understood that any covalent bond-forming reaction can be used to conjugate a GalNAc-containing moiety to a compound (e.g., a nucleic acid as described herein, such as an oligonucleotide or mRNA, or other agent) in order provide a conjugate or compound of the present invention. Exemplary reactions include, but are not limited to, alkylation reactions, metathesis reactions, addition reactions, substitution reactions, cycloaddition reactions, etc. In certain embodiments, the reaction used in the conjugation is a cycloaddition reaction. In certain embodiments, the cycloaddition is a [4+2] cycloaddition. In certain embodiments, the cycloaddition is a 1,3-dipolar cycloaddition. In certain embodiments, the reaction is an azide-alkyne cycloaddition (i.e., Huisgen cycloaddition). In certain embodiments, the cycloaddition is performed in the presence of a catalyst. In certain embodiments, the catalyst is a copper catalyst.

In certain embodiments, the reaction used to conjugate the agent (e.g., a nucleic acid as described herein such as an oligonucleotide or mRNA) to the GalNAc targeting moiety is a "click chemistry" reaction (e.g., the Huisgen alkyne-azide cycloaddition). It is to be understood that any "click chemistry" reaction known in the art can be used to this end. Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine [4+2] cycloaddition). Examples of click chemistry reactions can be found in, e.g., Kolb, H. C.; Finn, M. G. and Sharpless, K. B. *Angew. Chem. Int. Ed.* 2001, 40, 2004-2021. Kolb, H. C. and Shrapless, K. B. *Drug Disc. Today,* 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120.

In certain embodiments, the method of preparing a conjugate or compound described herein comprises contacting a targeting ligand (i.e., a sugar, a folate or cell-penetrating peptide) comprising a first click chemistry handle with an agent (e.g., a nucleic acid as described herein such as an oligonucleotide or mRNA) comprising a second tt chemistry handle. In certain embodiments, the method comprises contacting a targeting ligand comprising an azide moiety with an an agent (e.g., a nucleic acid as described herein such as an oligonucleotide or mRNA) comprising an alkyne moiety. In other embodiments, the method comprises contacting a targeting ligand comprising an alkyne moiety with an agent (e.g., a nucleic acid as described herein such as an oligonucleotide or mRNA) comprising an azide moiety.

In another aspect, provided herein is a method for preparing a conjugate of Formula (I-c):

(I-c)

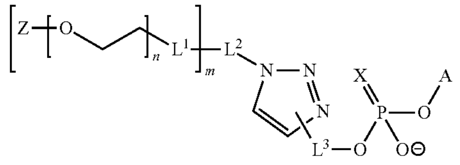

or a pharmaceutically acceptable salt thereof, wherein: A is a group comprising a nucleic acid; X is O or S; Z is a sugar, a folate, or a cell-penetrating peptide; each of $L^1$, $L^2$, and $L^3$ is independently a bond, optionally substituted alkylene, or optionally substituted heteroalkylene; wherein each $L^1$ optionally comprises a triazole; m is an integer from 3 to 10, inclusive; and n is an integer from 1 to 10, inclusive;

comprising contacting a compound of Formula (I-c-Az):

(I-c-Az)

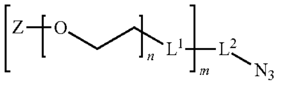

or a salt thereof, with a compound of Formula (I-c-Alk):

(I-c-Alk)

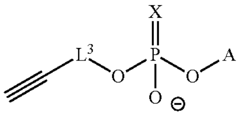

under conditions suitable to yield the conjugate of Formula (I-c) or a pharmaceutically acceptable salt thereof.

In an embodiment, the step of contacting is carried out in the presence of copper. In a particular embodiment, the copper is present in a catalytic amount.

In an embodiment, the compound of Formula (I-c) is of Formula (I-d):

(I-d)

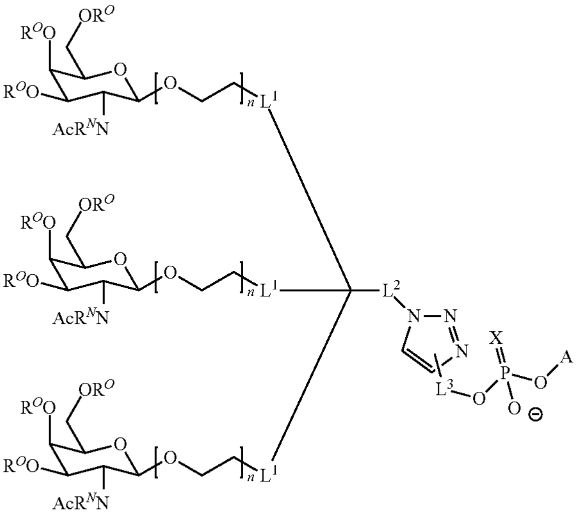

or a pharmaceutically acceptable salt thereof, wherein: each instance of RN is independently hydrogen, optionally substituted alkyl; optionally substituted acyl; or a nitrogen protecting group; each instance of RO is independently hydrogen, optionally substituted alkyl, optionally substituted acyl; or an oxygen protecting group; and the compound of Formula (I-c-Az) is of Formula (I-d-Az):

(I-d-Az)

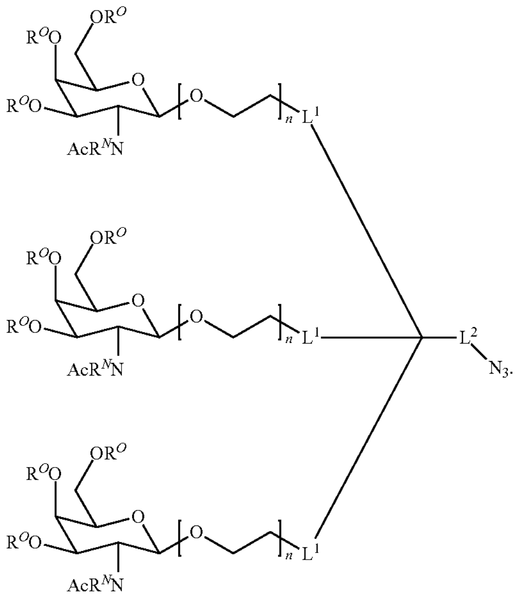

In an embodiment, the compound of Formula (I-d) is of Formula (I-e):

(I-e)
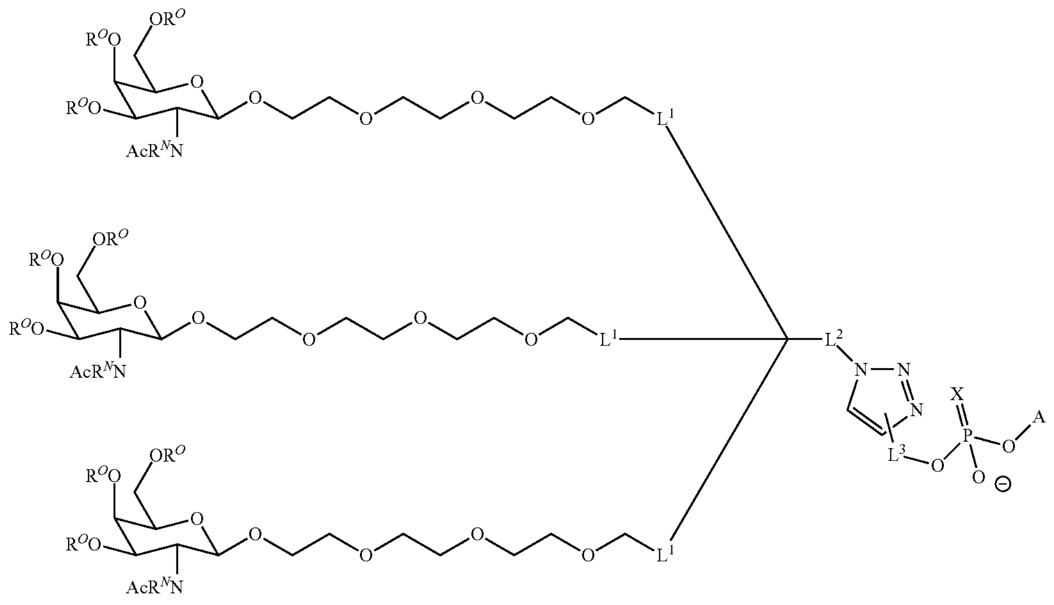
or a pharmaceutically acceptable salt thereof; and the compound of Formula (I-d-Az) is of the Formula (I-e-Az):
(I-e-Az)
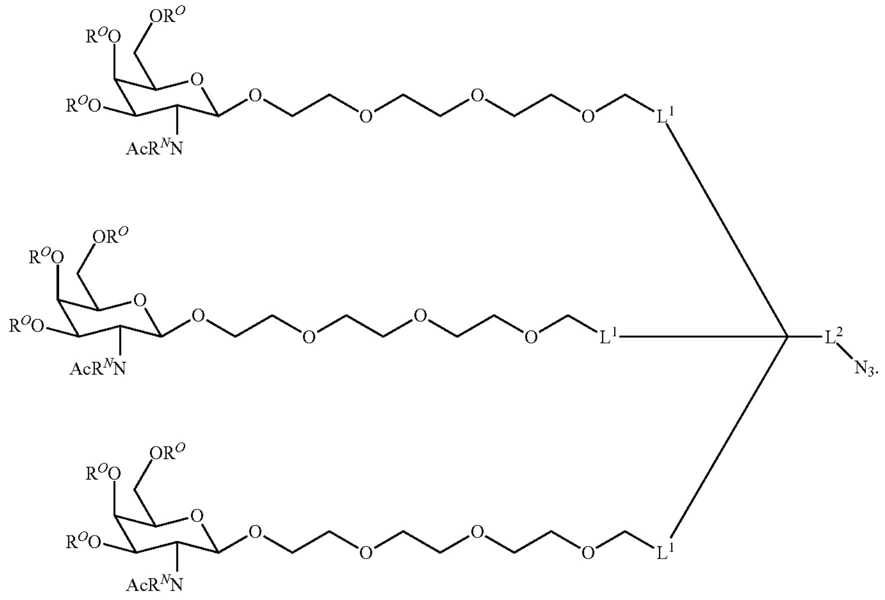
In an embodiment, the compound of Formula (I-e) is of Formula (I-f):

(I-f)
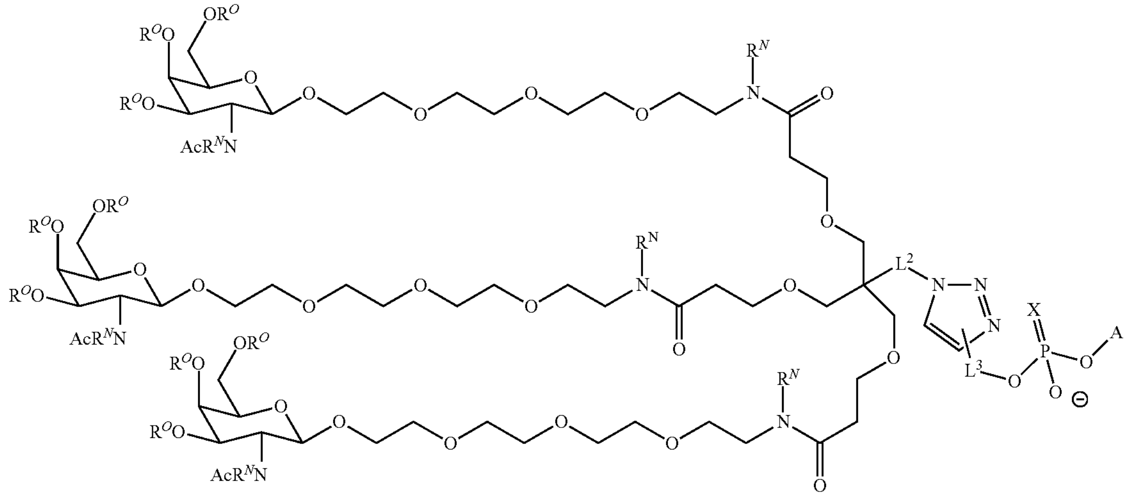
or a pharmaceutically acceptable salt thereof; and the compound of Formula (I-e-Az) is of the Formula (I-f-Az):
(I-f-Az)
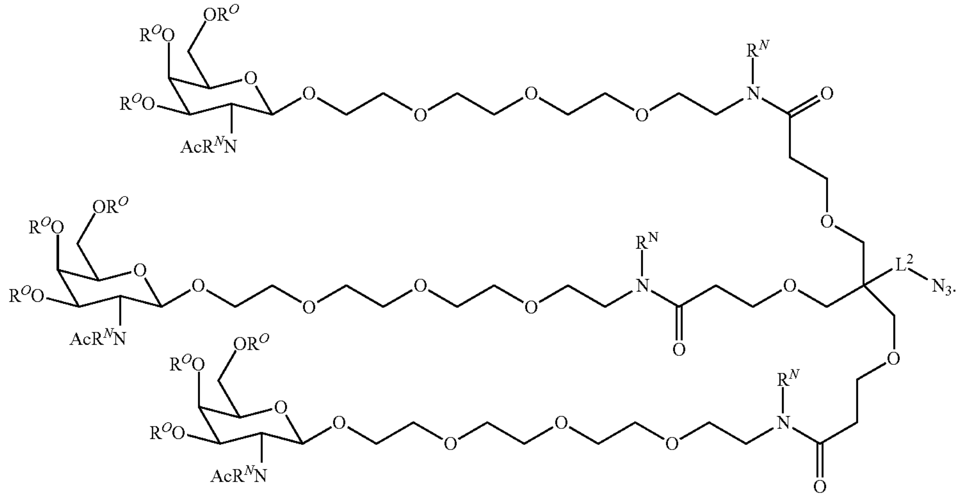
In an embodiment, the compound of Formula (I-f) is of Formula (I-g):

(I-g)
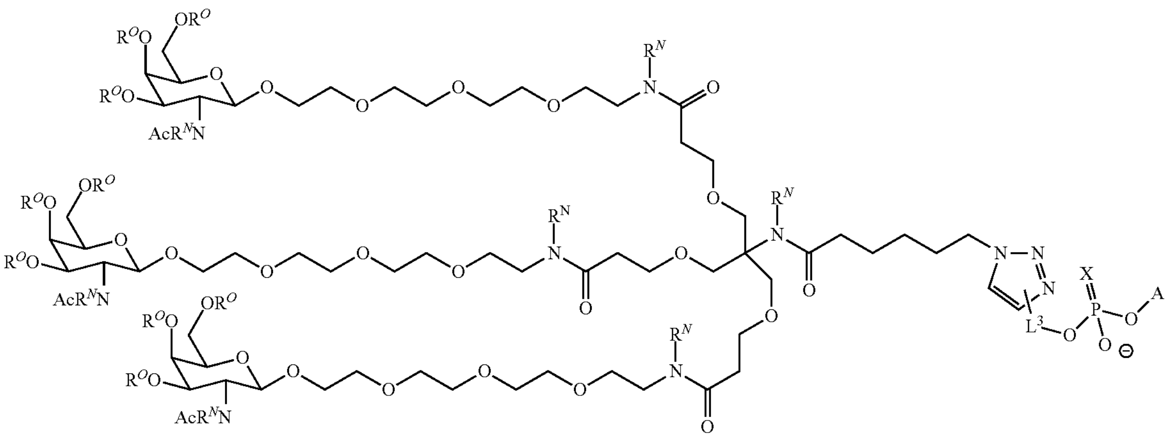
or a pharmaceutically acceptable salt thereof; and the compound of Formula (I-f-Az) is of the Formula (I-g-Az):
(I-g-Az)
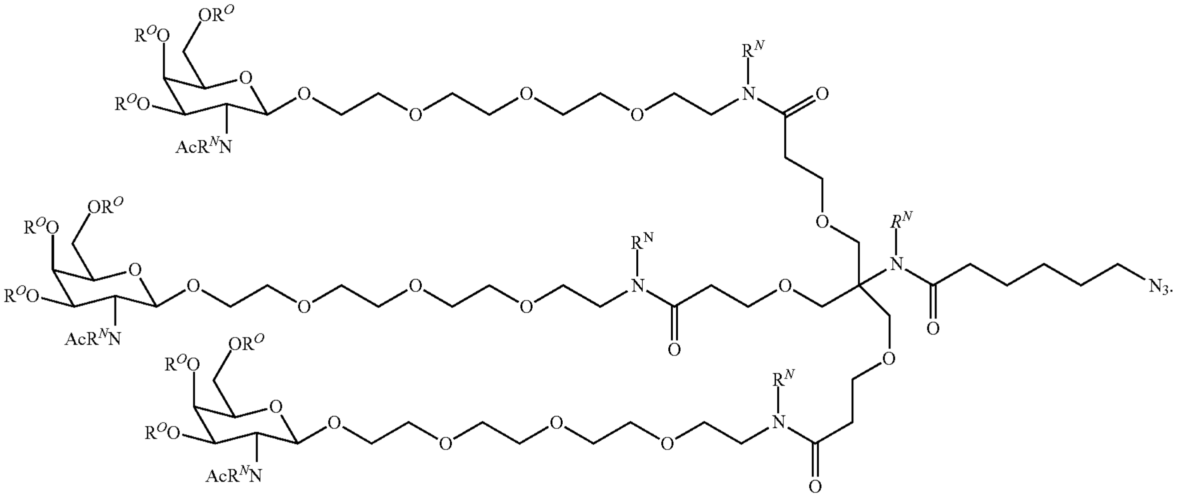
In an embodiment, the compound of Formula (I-g) is of Formula (I-h):

(I-h)
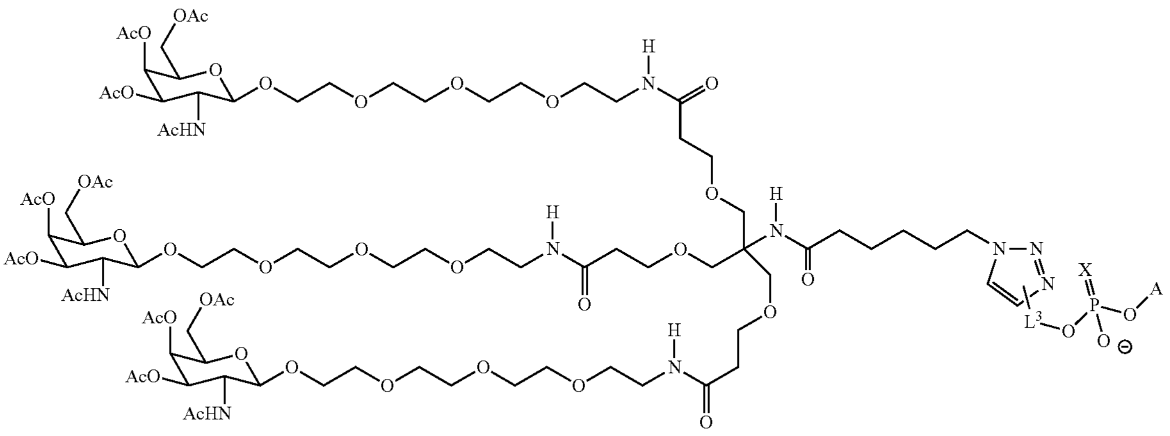
or a pharmaceutically acceptable salt thereof; and the compound of Formula (I-g-Az) is of the Formula (I-h-Az):
(I-h-Az)
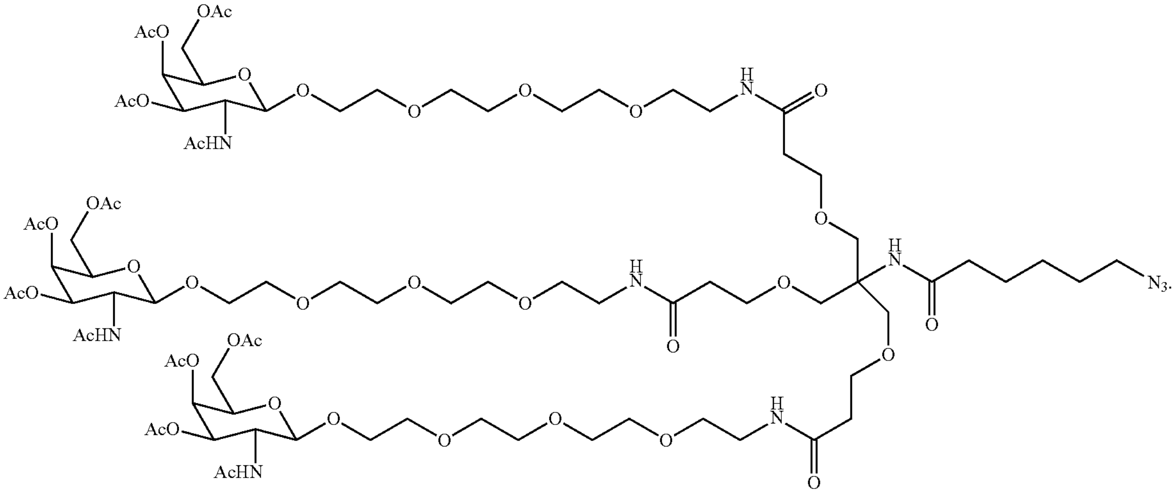
In an embodiment, the compound of Formula (I-h) is of Formula (I-i):

(I-i)

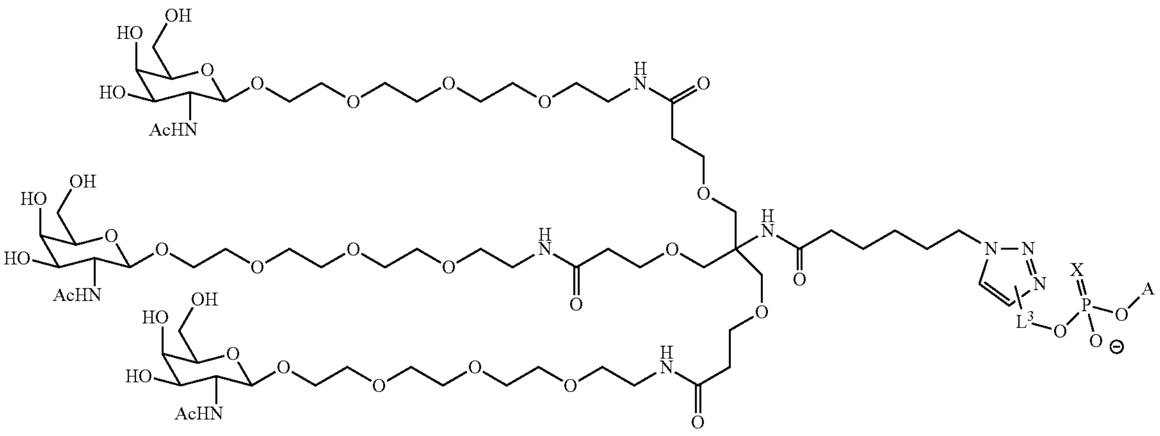

or a pharmaceutically acceptable salt thereof; and the compound of Formula (I-h-Az) is of the Formula (I-i-Az):

(I-i-Az)

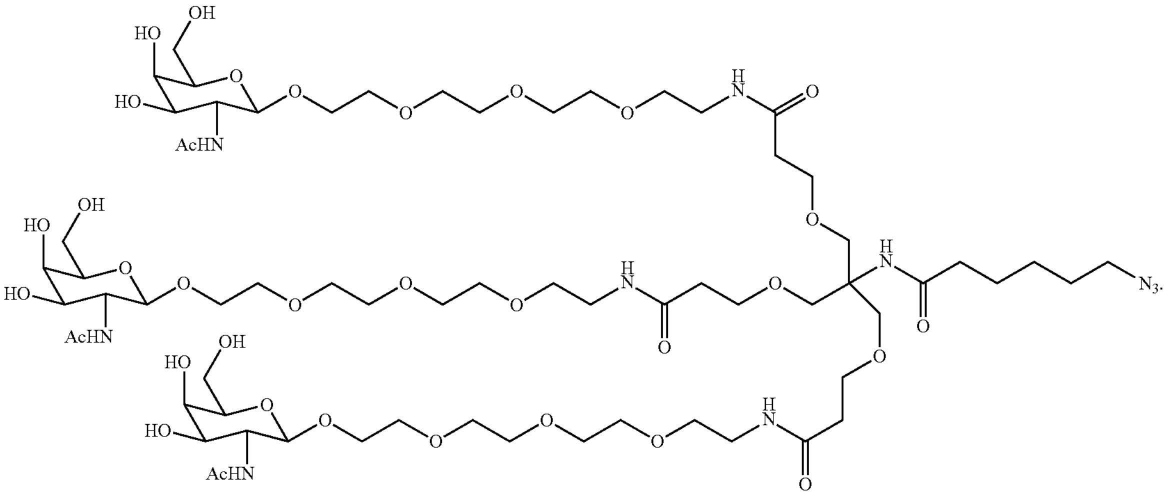

In a particular embodiment, the compound of Formula (I-c-Alk) is of the following formula:

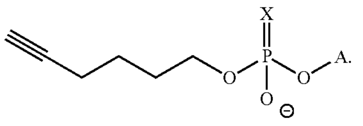

In another aspect, provided herein is a method for preparing a conjugate of Formula (I-j):

(I-j)

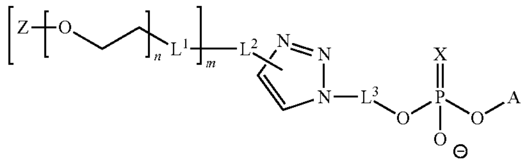

or a pharmaceutically acceptable salt thereof, wherein: A is a group comprising a nucleic acid; X is O or S; Z is a sugar, a folate, or a cell-penetrating peptide; each of $L^1$, $L^2$, and $L^3$ is independently a bond, optionally substituted alkylene, or optionally substituted heteroalkylene; wherein each $L^1$ optionally comprises a triazole; m is an integer from 3 to 10, inclusive; and n is an integer from 1 to 10, inclusive;

comprising contacting a compound of Formula (I-j-Alk):

(I-j-Alk)

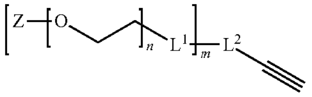

or a salt thereof, with a compound of Formula (I-j-Az):

(I-j-Az)

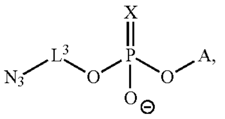

under conditions suitable to yield the conjugate of Formula (I-j).

In an embodiment, the step of contacting is carried out in the presence of copper. In a particular embodiment, the copper is present in a catalytic amount.

In an embodiment, the conjugate of Formula (I-j) is of Formula (I-k):

(I-k)

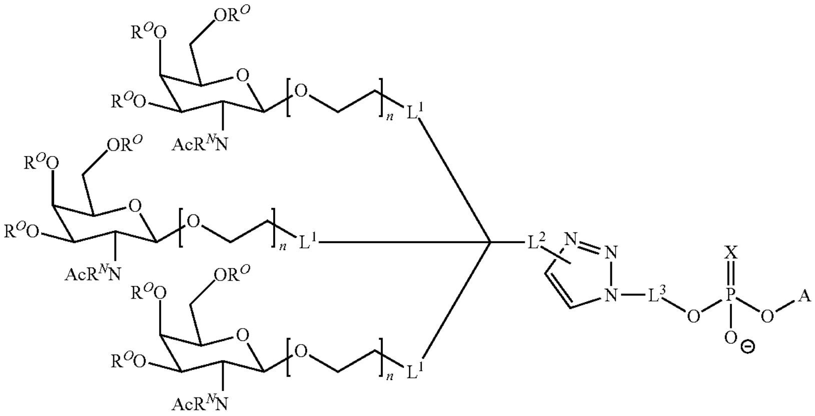

or a pharmaceutically acceptable salt thereof; and the compound of Formula (I-j-Alk) is of Formula (I-k-Alk):

(I-k-Alk)

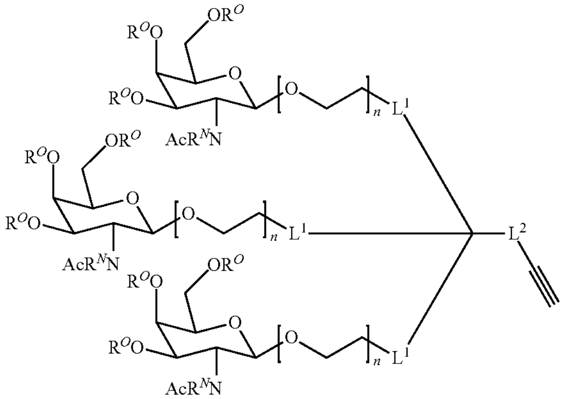

or a salt thereof, and the compound of Formula (I-j-Az) is of the Formula (I-k-Az):

(I-k-Az)

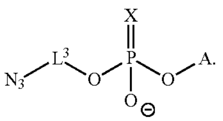

In certain embodiments, the steps of contacting described above comprise contacting the starting materials in the presence of a metal. In certain embodiments, the metal is a copper reagent (e.g., copper salt). In certain embodiments, the copper reagent is present in a catalytic amount. In certain embodiments, the metal is a ruthenium complex. In certain embodiments, the ruthenium complex is present in a catalytic amount. In certain embodiments, the reactions to form a compound of Formula (I) are carried out in the presence of one or more additional reagents. Reagents and conditions useful in the azide-alkyne cycloaddition described herein can be found in the art. Examples of reagents and conditions useful in these methods can be found in, e.g., Folkin, V. V. et al. *Org. Lett.* 2005, 127, 15998-15999; Kraniski, A.; Fokin, V. V. and Sharpless, K. B. *Org. Lett.* 2004, 6, 1237-1240; Padwa, A. 1,3-*Dipolar Cycloaddition Chemistry: 6 Volume* 1, John Wiley, New York, (1984) 1-176; Jorgensen, K. A. *Angew. Chem. Int. Ed.* 2000, 39, 3558-3588; Tietze, L. F. and Kettschau, G. *Top. Curr. Chem.* 1997, 189, 1-120; Tomoe, C. W.; Christensen, C. and Meldal, M. *J. Org. Chem.* 2002, 67, 3057-3064; Chan, T. R. et al. *Org. Lett.* 2004, 6, 2853-2855; Lewis, W. G. et al., *J. Am. Chem. Soc.* 2004, 126, 9152-9153; Mantovani, G. et al. *Chem. Comm.* 2005, 2089-2091; Diez-Gonzalez, S. et al. *Chem. Eur. J.* 2006, 12, 7558-7564; Candelon, N. et al. *Chem. Comm.* 2008, 741-743; Rostovtsev, V. V. et al. *Angew. Chem.* 2002, 114, 2708-2711; *Angew. Chem., Int. Ed.* 2002, 41, 2596-2599; Himo, F. et al. *J. Am. Chem. Soc.* 2005, 127, 210-216; Pachon, L. D. et al. *Adv. Synth. Catal.* 2005, 347, 811-815; Molteni, G. et al. *New J. Chem,* 2006, 30, 1137-1139; Chassaing et al. *Chem. Eur. J.* 2008, 14, 6713-6721; Sharpless, W. D.; Wu, P.; Hansen, T. V.; and Li, J. G. J. *Chem. Ed.* 2005, 82, 1833; Chan, T. R.; Hilgraf, R.; Shrapless, K. B. and Fokin, V. V. *Org. Lett.* 2004, 6, 2853; Rostoctsev, V. V.; Green L. G.; Fokin, V. V. and Shrapless, K. B. *Angew. Chem., Int. Ed.* 2002, 41, 2596-2599. Especially useful are the reagents and conditions described in, e.g., Manoharan, et.al. *Org. let.* 2010, 12, 5410-5413; Manoharan, et.al. *ACS Chem. Biol.* 2015, 10, 1181-1187.

The methods for preparing a compound of Formula (I) describe herein may further comprise one or more addition steps, e.g., to protect or deprotect functional groups. For example, in certain embodiments, after a compound of Formula (I) is formed, a step of deprotection may be carried out to remove protecting groups (e.g., from the sugar moieties).

The present invention also provides intermediates useful in the preparation of conjugates and compounds described herein. In one aspect, the present invention provides compounds of Formula (I-c-Az). In certain embodiments, a compound of Formula (I-c-Az) is a compound of Formula (I-e-Az):

(I-e-Az)

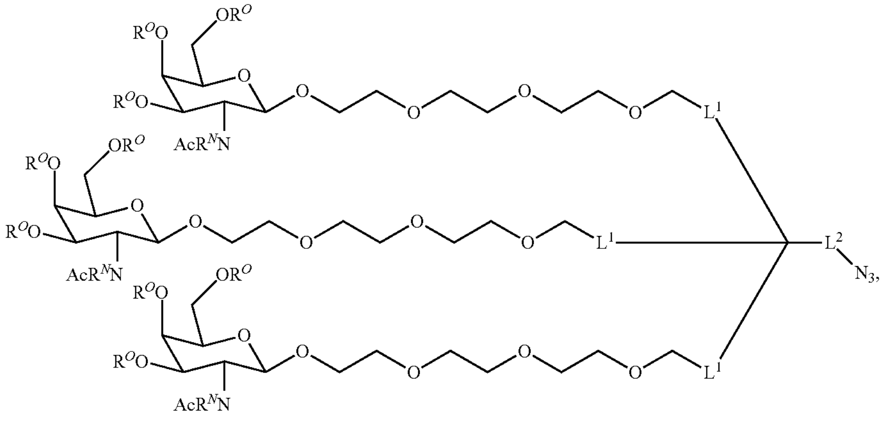

or a salt thereof, wherein $L^1$, $L^2$, $R^N$, and $R^O$ are as defined herein.

In certain embodiments, a compound of Formula (I-e-Az) is of Formula (I-f-Az):
(I-f-Az)
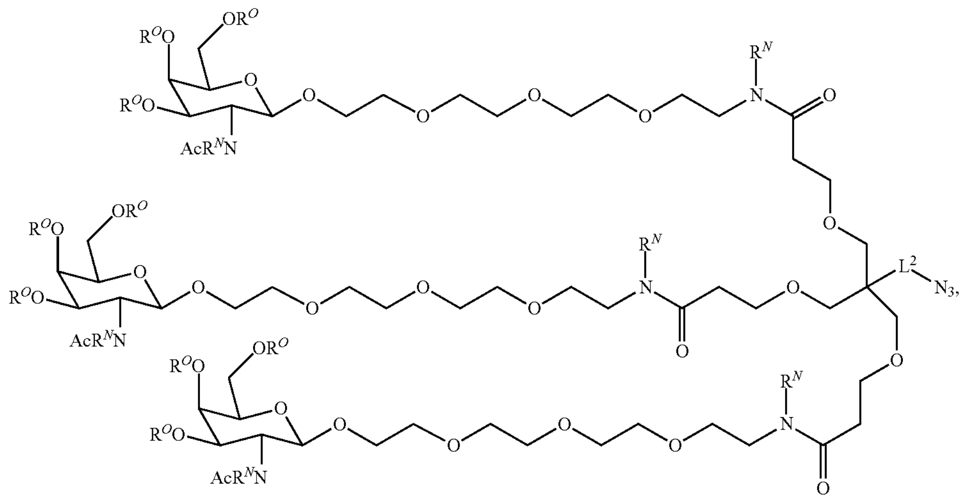
or a salt thereof.
In certain embodiments, a compound of Formula (I-f-Az) is of Formula (I-g-Az):
(I-g-Az)
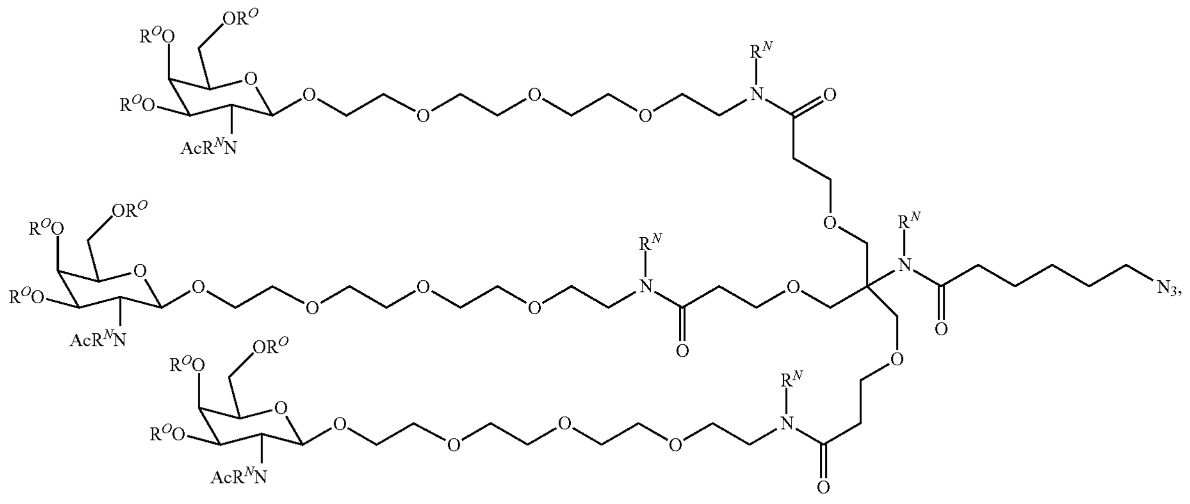
or a salt thereof.
In certain embodiments, a compound of Formula (I-g-Az) is of Formula (I-h-Az):

(I-h-Az)

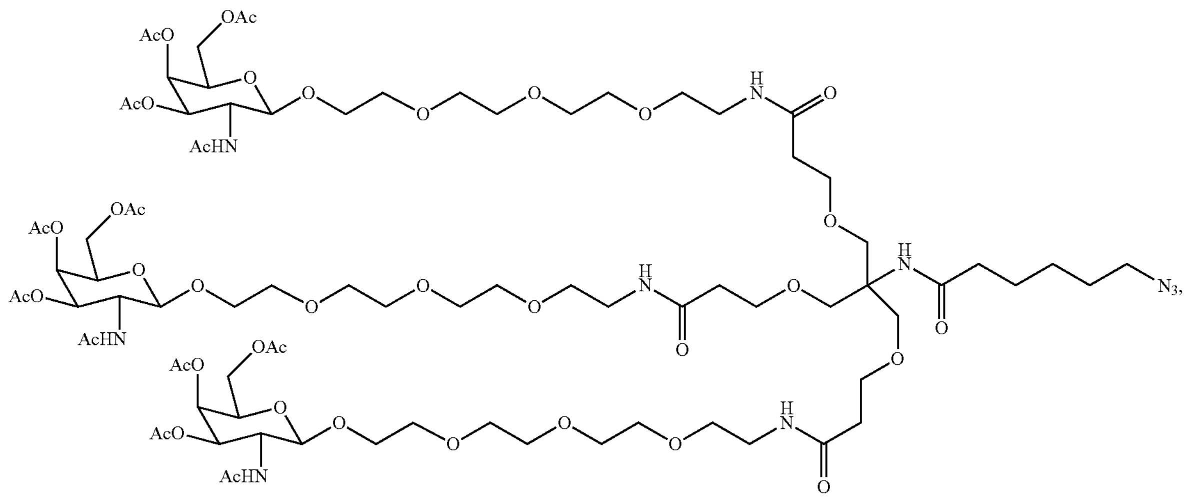

or a salt thereof.

In certain embodiments, a compound of Formula (I-h-Az) is of Formula (I-i-Az):

(I-i-Az)

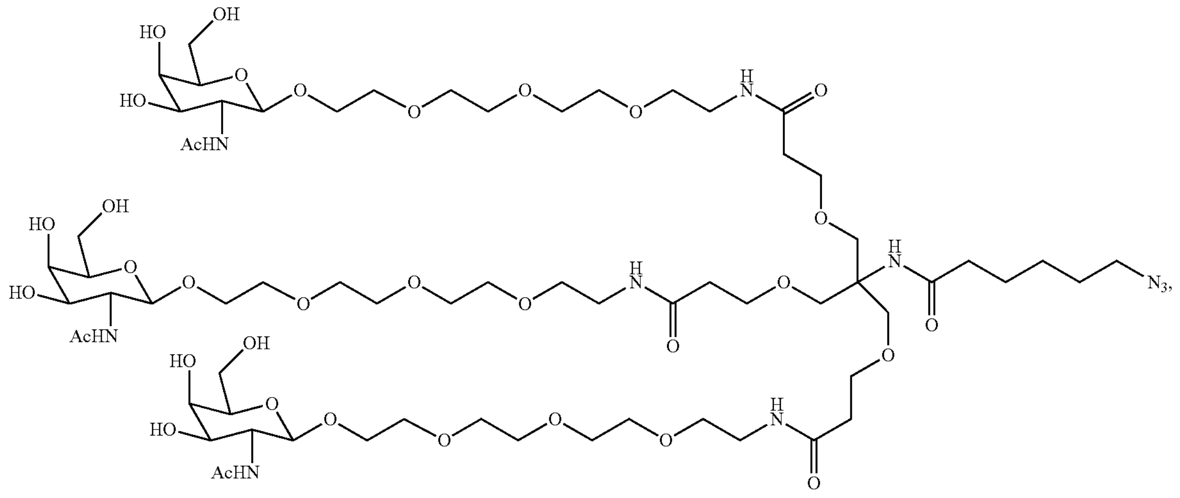

or a salt thereof.

In certain embodiments, the compound of Formula (I-c-Alk) is of the formula:

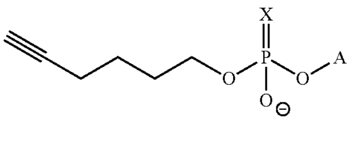

or a salt thereof.

In certain embodiments, the compound of Formula (I-c-Alk) is of the following formula:

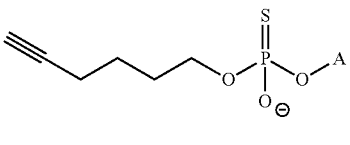

or a salt thereof.

In another aspect, provided herein is a compound of Formula (I-k-Alk):

(I-k-Alk)
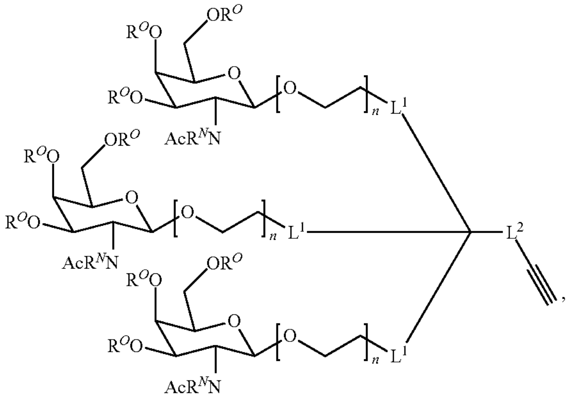
or a salt thereof.
For example, in certain embodiments, a compound of Formula (I-k-Alk) is of one of the following formulae:
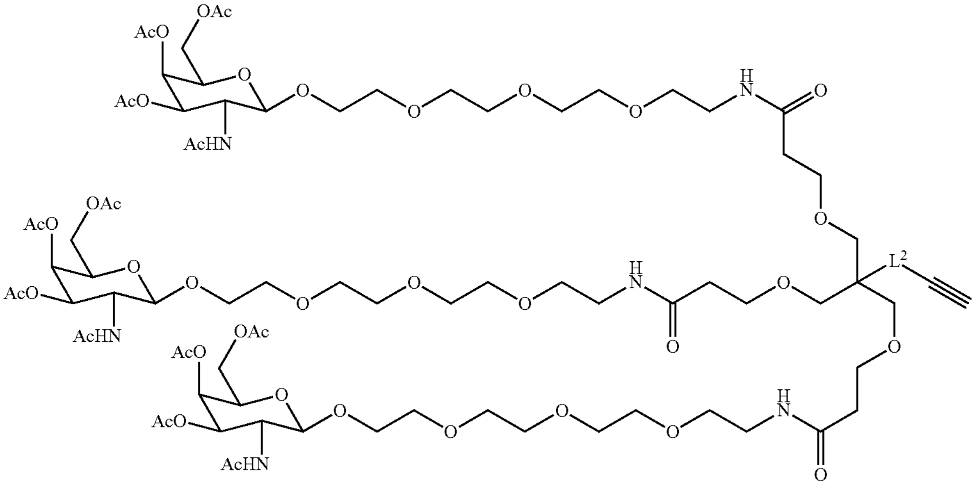
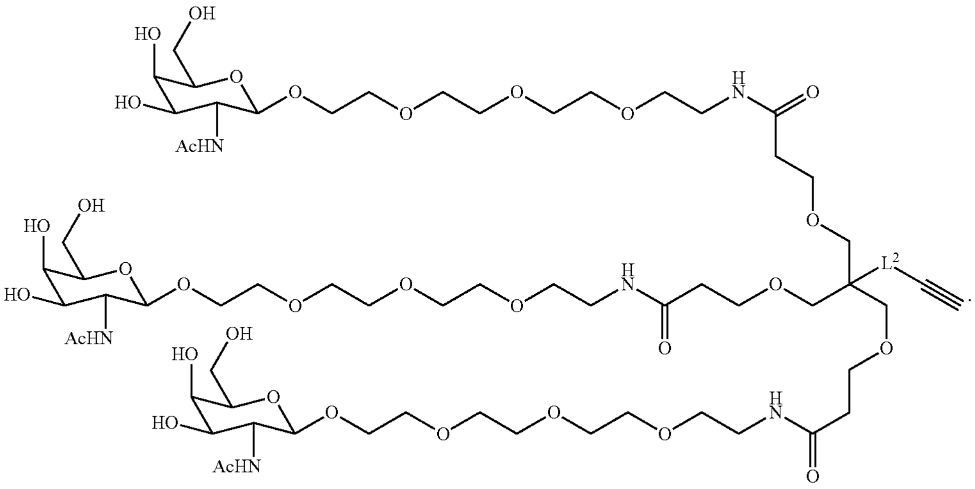
For example, in certain embodiments, a compound of Formula (I-k-Alk) is of one of the following formulae:

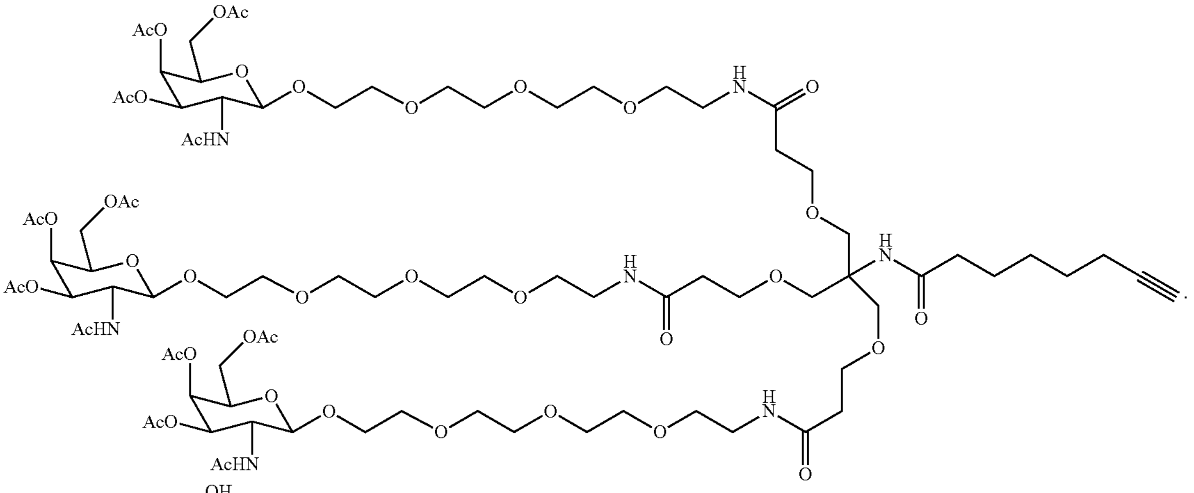

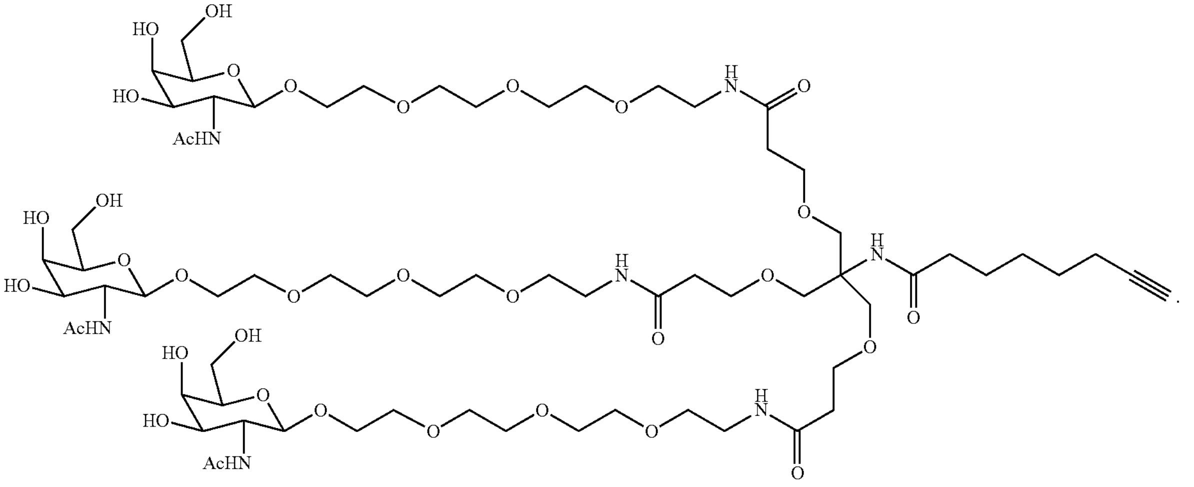

Kits

Also encompassed by the disclosure are kits (e.g., pharmaceutical packs). The kits provided may comprise a conjugate, compound, or composition described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or conjugate/compound described herein. In some embodiments, the pharmaceutical composition or compound described herein provided in the first container and the second container are combined to form one unit dosage form.

Thus, in one aspect, provided are kits including a first container comprising a conjugate, compound, or pharmaceutical composition described herein. In certain embodiments, the kits are useful for treating a disease in a subject in need thereof. In certain embodiments, the kits are useful for preventing a disease in a subject in need thereof. In certain embodiments, the kits are useful for modulating gene expression in a subject in need thereof. In other embodiments, the kits are useful for delivering a nucleic acid as described herein (e.g., an oligonucleotide or mRNA) to a cell (e.g., in vivo, in vitro, or ex vivo)

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease in a subject in need thereof. In certain embodiments, the kits and instructions provide for preventing a disease in a subject in need thereof. A kit described herein may include one or more additional pharmaceutical agents described herein as a separate composition.

The present invention also provides kits for the preparation of conjugates and compounds described herein (e.g., conjugates of Formula (I-a)). Provided herein are kits comprising a targeting moiety functionalized with a click chemistry handle; optionally a compound (e.g., a nucleic acid as described herein such as an oligonucleotide or mRNA) functionalized with a click chemistry handle; optionally one or more reagents for performing a click chemistry reaction; and optionally instructions for use. For example, provided herein is a kit comprising a targeting moiety functionalized with an azide (e.g., a compound of Formula (I-c-Az)); optionally a nucleic acid as described herein (e.g., an oligonucleotide or mRNA) functionalized with an alkyne (e.g., a compound of Formula (I-c-Alk)); optionally a reagent for promoting an alkyne-azide click chemistry reaction (e.g., a copper salt); and optionally instructions for carrying out a click chemistry reaction. In another embodiment, the present invention provides kits comprising a targeting moiety functionalized with an alkyne (e.g., a compound of Formula (I-k-Alk)); optionally a nucleic acid as described herein (e.g., an oligonucleotide or mRNA) functionalized with an azide; optionally a reagent for promoting an alkyne-azide click chemistry reaction (e.g., a copper salt); and optionally instructions for carrying out a click chemistry reaction.

Group A

In the conjugates described herein, group A is a group comprising a nucleic acid or a nanoparticle component (e.g., a lipid nanoparticle component). In a particular embodiment, group A comprises a nucleic acid. In a particular embodiment, group A is a nucleic acid. In another particular embodiment, group A comprises a lipid nanoparticle component. In another particular embodiment, group A is a lipid nanoparticle component. The nucleic acid may be, e.g., an oligonucleotide, a DNA, a DNA/RNA hybrid molecule, or an RNA such as an mRNA, non-coding RNA, or guide RNA.

In some embodiments, where A is a nanoparticle component (e.g., a lipid nanoparticle component), the conjugate further comprises one or more additional nanoparticle components (e.g., additional lipid nanoparticle components), such that the nanoparticle component of A (e.g., a lipid nanoparticle component) and the additional nanoparticle components (e.g., additional lipid nanoparticle components) form a nanoparticle (e.g., a lipid nanoparticle). The nanoparticle may further comprise (e.g., form a complex with) a nucleic acid (e.g., an oligonucleotide, synthetic mRNA, or siRNA). In some embodiments, the lipids form a lipid bilayer surrounding the nucleic acid, e.g., in a micellar structure. However, other lipid nanoparticle and nucleic acid complexes may be formed, including other unilamellar or multilamellar aggregates or vesicles.

In an embodiment, the lipid nanoparticle component is a cationic lipid, a non-cationic lipid, a conjugated lipid, a fusogenic lipid, cholesterol or a cholesterol derivative (e.g., esters or conjugates thereof). In an embodiment, the lipid nanoparticle component is a cationic lipid selected from N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9, 12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1, 1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech Gl), 2,2-Dilinoleyl-4-dimethylaminoethyl-[1,3]-dioxolane, β-L-arginyl-2, 3-L-diaminopropionic acid-N-palmityl-N-oleylamide trihydrochloride, N',N'-dioctadecyl-N-4, 8-diaza-10-aminodecanoylglycine amide[71], 1,2-dilinoleyloxy-3-dimethylaminopropane, DLin-KC2-DMA, amino lipid 2,2-dilinoleyl-4-dimethylaminoethyl-[1,3]-dioxolane (DLin-KC2-DMA, 1), 1,2-distearloxy-N,N-dimethylaminopropane (DSDMA), dilinoleylmethyl-4-dimethylaminobutyrate (DLin-MC3-DMA), DLin-D-DMA, C12-200, 98N12-5, (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimethylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propa-n-2-amine, S—N,N-dimethyl-1-[(9Z,12Z)-octadeca-9,12-dien-1-yloxy]-3-(octy-loxy)propan-2-amine, 1-{2-[(9Z,12Z)-octadeca-9,12-dien-1-yloxy]-1-Roctyloxy)methyl]ethyl}pyrro-lidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azet-idine, (2S)-1-(hexyloxy)-N,N-dimethyl-3-[(9Z,12Z)-octadeca-9,12-dien-1-ylo-xy]propan-2-amine, (2S)-1-

(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy] propan-2-amine, N,N-dimethyl-1-[(9Z)-octadec-9-en-1-yloxy]-3-(octyloxy)propan-2-am-ine; (2S)—N,N-dimethyl-1-[(6Z,9Z,12Z)-octadeca-6,9,12-trien-1-yloxy]-3-(o-ctyloxy)propan-2-amine, (2 S)-1-[(11Z,14Z)-icosa-11,14-dien-1-yloxy]-N,N-dimethyl-3-(pentyloxy)propa-n-2-amine, (2S)-1-(hexyloxy)-3-[(11Z,14Z)-icosa-11,14-dien-1-yloxy]-N,N-di-methylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)pr-opan-2-amine, (2S)-1-[(13Z,16Z)-docosa-13,16-dien-1-yloxy]-3-(hexyloxy)-N,N-dimethylpro-pan-2-amine, (2S)-1-[(13Z)-docos-13-en-1-yloxy]-3-(hexyloxy)-N,N-dimethylpropan-2-amin-e, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy)propan-2-amine, (2R)—N,N-dimethyl-H (1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-di-en-1-yloxy] propan-2-amine, N,N-dimethyl-1-(octyloxy)-3-({8-[(1S,2S)-2-{[(1R,2R)-2-pentylcyclopropyl]-methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-11,20,2-trien-10-amine, 5-carboxyspermylglycine dioctaoleoylamide (“DOGS”), dipalmitoylphosphatidylethanolamine 5-carboxyspermyl-amide (“DPPES”), 1,2-dimyristyloxypropyl-3-dimethyl-hydroxy ethyl ammonium bromide (DMRIE), DMRIE-HP, Lipofectamine (DOSPA), 3b-(N—(N',N'-dimethylamino-ethane)-carbamoyl)cholesterol (“DC-Choi”), N-(1,2-dimyhstyloxyprop-3-yl)-N,N-dimethyl-N-hydroxyethyl ammonium bromide (“DMRIE”), 1,2-Dioleoyl-3-dimethylammonium-propane (“DODAP”), DMDMA, cationic lipid-based transfection reagents TransIT-TKO, LIPOFECTIN, Lipofectamine, OLIGOFECTAMINE or DHARMAFECT, DSDMA, DODMA, DLinDMA, DLenDMA, gamma-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-Bl 1).

In an embodiment, the lipid nanoparticle component is a non-cationic lipid, wherein the non-cationic lipid is an anionic lipid. In an embodiment, the lipid nanoparticle component is a non-cationic lipid, wherein the non-cationic lipid is a neutral lipid.

In an embodiment, the lipid nanoparticle component is a non-cationic lipid selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

In an embodiment, the anionic lipid is 1,2-dioleoyl-sn-glycero-3-phospho-(1'-rac-glycerol). In an embodiment, the neutral lipid is 1,2-dioleoyl-sn-glycero-3-phosphatidylcholine.

In an embodiment, the lipid nanoparticle component is a conjugated lipid that inhibits aggregation of particles. In some embodiments, the conjugated lipid is a PEG lipid. In some embodiments, the PEG lipid is a PEG-diacylglycerol (DAG), a PEG-dialkyloxypropyl (DAA), a PEG-phospholipid, a PEG-ceramide (Cer), or a mixture thereof. In some embodiments, PLGA is conjugated to a lipid-terminating PEG forming PLGA-DSPE-PEG. In some embodiments, a PEG lipid is selected from PEG-c-DOMG and 1,2-Dimyristoyl-sn-glycerol, methoxypolyethylene Glycol (PEG-DMG), 1,2-Distearoyl-sn-glycerol, methoxypolyethylene Glycol (PEG-DSG), PEG-c-DOMG, 1,2-Distearoyl-sn-glycerol, methoxypolyethylene glycol (PEG-DSG) 1,2-Dipalmitoyl-sn-glycerol, methoxypolyethylene glycol (PEG-DPG), PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers (e.g., ATTA-lipid conjugates), and mixtures thereof. In some embodiments, the PEG is a PEG-dilauryloxypropyl (C12), a PEG-dimyristyloxypropyl (C14), a PEG-dipalmityloxypropyl (C16), a PEG-distearyloxypropyl (C18), PEG-c-DOMG, PEG-DMG, or a mixture thereof.

In an embodiment, group A comprises a single-stranded oligonucleotide. In a particular embodiment, group A comprises mRNA. In another particular embodiment, group A comprises an antisense oligonucleotide. In an embodiment, group A comprises a double-stranded oligonucleotide. In a particular embodiment, group A comprises siRNA. In an embodiment, group A comprises a cleavable linker covalently linked to the nucleic acid.

As defined herein, “oligonucleotide” (also referred to as “polynucleotide”) refers to a series of nucleotide bases (also called “nucleotides”) in DNA and RNA, and means any chain of two or more nucleotides. The oligonucleotides can be chimeric mixtures or derivatives or modified versions thereof; and can be single-stranded (including, for example gapmers, mixmers, or uniform chemistries) or double-stranded (including, for example, siRNA and microRNA mimics). The oligonucleotide can be modified at the base moiety, sugar moiety, or phosphate backbone, for example, to improve stability of the molecule, its hybridization parameters, etc. In certain embodiments, the oligonucleotide is an antisense oligonucleotide.

The oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine.

A nucleotide sequence typically carries genetic information, including the information used by cellular machinery to make proteins and enzymes. These terms include double- or single-stranded genomic and cDNA, RNA, any synthetic and genetically manipulated polynucleotides, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone.

Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA.

Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

In some embodiments, the nucleic acid is a synthetic RNA. As used herein the term, "synthetic RNA" refers to a RNA produced through an in vitro transcription reaction or through artificial (non-natural) chemical synthesis or through a combination thereof. In some embodiments, a synthetic RNA is an mRNA. In some embodiments, a synthetic RNA encodes a protein. In some embodiments, the synthetic RNA is a functional RNA (e.g., a tRNA, rRNA, snoRNA, miRNA, ncRNA, long-noncoding RNA, or shRNA). In some embodiments, a synthetic RNA comprises one or more modified nucleotides as described herein. In some embodiments, the synthetic RNA further comprises a poly A tail, a Kozak sequence, a 3' untranslated region, a 5' untranslated region, or any combination thereof. Poly A tails in particular can be added to a synthetic RNA using a variety of art-recognized techniques, e.g., using poly A polymerase (Yokoe, el al. Nature Biotechnology. 1996; 14: 1252-1256), using transcription directly from PCR products, or by ligating to the 3' end of a synthetic RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the poly A tail, the Kozak sequence, the 3' untranslated region, the 5' untranslated region, or the any combination thereof comprises one or more modified nucleotides as described herein.

In some embodiments, a synthetic RNA (e.g., synthetic mRNA) is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, 25 kb, 30 kb or more in length. In some embodiments, a synthetic RNA is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

In some embodiments, the synthetic RNA is unmodified. In some embodiments, the synthetic RNA is modified to include at least one modified nucleotide or modified internucleotide linkage. In some embodiments, a synthetic mRNA provided herein contains modified nucleotides in the open reading frame. In some embodiments, the modified nucleotide is selected from the group consisting of: 2'-amino-2'-deoxynucleotide, 2'-azido-2'-deoxynucleotide, 2'-fluoro-2'-deoxynucleotide, 2'-O-methyl-nucleotide, 2' sugar super modifier, 2'-modified thermostability enhancer, 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, pseudouridine-5'-triphosphate, 2'-O-methylinosine-5'-triphosphate, 2'-amino-2'-deoxycytidine-5'-triphosphate, 2'-amino-2'-deoxyuridine-5'-triphosphate, 2'-azido-2'-deoxycytidine-5'-triphosphate, 2'-azido-2'-deoxyuridine-5'-triphosphate, 2'-O-methylpseudouridine-5'-triphosphate, 2'-O-methyl-5-methyluridine-5'-triphosphate, 2'-azido-2'-deoxyadenosine-5'-triphosphate, 2'-amino-2'-deoxyadenosine-5'-triphosphate, 2'-fluoro-thymidine-5'-triphosphate, 2'-azido-2'-deoxyguanosine-5'-triphosphate, 2'-amino-2'-deoxyguanosine-5'-triphosphate, and N4-methylcytidine-5'-triphosphate. See, e.g., U.S. Pat. No. 8,278,036 or WO2011012316 for a discussion of such residues and their incorporation into a synthetic RNA. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification.

In some embodiments, the synthetic RNA comprises a 5' cap. In some embodiments, the cap is a methyl guanosine (m7G) cap. In some embodiments, the cap is a mRNA cap analogue (e.g., mCAP (m7G(5')ppp(5')G) or Anti-Reverse Cap Analog (ARCA) (3' O-Me-m7G(5')ppp(5')G)). For mRNA capping enzymes and procedures, see, e.g., Fechter, P.; Brownlee, G. G. "Recognition of mRNA cap structures by viral and cellular proteins" J. Gen. Virology 2005, 86, 1239-1249; European patent publication 2 010 659 A2; U.S. Pat. No. 6,312,926. In some embodiments, a 5' cap is added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase.

It should be appreciated that nucleic acid (e.g., an oligonucleotide or mRNA) may be single stranded or double stranded. Single stranded nucleic acids may include secondary structures, e.g., a loop or helix structure, and thus may have one or more double stranded portions under certain physiochemical conditions. In some embodiments, the nucleic acid (e.g., oligonucleotide or mRNA) comprises at least one modified nucleotide or modified internucleoside linkage as described herein.

An oligonucleotide may have a region of complementarity with a target RNA transcript (e.g., a mammalian mRNA transcript) that has less than a threshold level of complementarity with every sequence of nucleotides, of equivalent length, of an off-target RNA transcript. For example, an oligonucleotide may be designed to ensure that it does not have a sequence that targets RNA transcripts in a cell other than the target RNA transcript. The threshold level of sequence identity may be 50%, 60%, 70%, 80%, 85%, 90%, 95%, 99% or 100% sequence identity.

An oligonucleotide may be complementary to RNA transcripts encoded by homologues of a gene across different species (e.g., a mouse, rat, rabbit, goat, monkey, etc.) In some embodiments, oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of an oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a target RNA. In some embodiments, the region of complementarity is complementary with at least 8 consecutive nucleotides of a target RNA.

"Complementary," as the term is used in the art, refers to the capacity for precise pairing between two nucleotides. For example, if a nucleotide at a certain position of an oligonucleotide is capable of hydrogen bonding with a nucleotide at a corresponding position of a target RNA, then the nucleotide of the oligonucleotide and the nucleotide of the target RNA are complementary to each other at that position. The oligonucleotide and target RNA are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and target RNA. For example, if a base at one position of an oligonucleotide is capable of hydrogen bonding with a base at the corresponding position of a target RNA, then the bases are considered to be complementary to each other at that position. 100% complementarity is not required.

An oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a target RNA. In some embodiments an oligonucleotide may contain 1, 2 or 3 base mismatches compared to the portion of the consecutive nucleotides of the target RNA. In some embodiments an oligonucleotide may have up to 3 mismatches over 15 bases, or up to 2 mismatches over 10 bases.

In some embodiments, an oligonucleotide is 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or more nucleotides in length. In some embodiments, the oligonucleotide is 8 to 50, 10 to 30, 9 to 20, 15 to 30 or 8 to 80 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, an oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches. Contiguous runs of three or more Gs or Cs may not be preferable in some embodiments. Accordingly, in some embodiments, the oligonucleotide does not comprise a stretch of three or more guanosine nucleotides.

An oligonucleotide may have a sequence that is has greater than 30% G-C content, greater than 40% G-C content, greater than 50% G-C content, greater than 60% G-C content, greater than 70% G-C content, or greater than 80% G-C content. An oligonucleotide may have a sequence that has up to 100% G-C content, up to 95% G-C content, up to 90% G-C content, or up to 80% G-C content. In some embodiments, GC content of an oligonucleotide is preferably between about 30-60%.

In some embodiments, an oligonucleotide may increase stability of a target RNA by at least about 50% (i.e. 150% of normal or 1.5 fold), or by about 2 fold to about 5 fold. In some embodiments, stability (e.g., stability in a cell) may be increased by at least about 15 fold, 20 fold, 30 fold, 40 fold, 50 fold or 100 fold, or any range between any of the foregoing numbers. In some embodiments, increased mRNA stability has been shown to correlate to increased protein expression. Similarly, in some embodiments, increased stability of non-coding positively correlates with increased activity of the RNA.

Oligonucleotides that are designed to interact with RNA to modulate gene expression are a distinct subset of base sequences from those that are designed to bind a DNA target (e.g., are complementary to the underlying genomic DNA sequence from which the RNA is transcribed).

In some embodiments, oligonucleotides are modified for delivery, hybridization and stability within cells to target RNA transcripts. Furthermore, in some embodiments, oligonucleotides are modified for controlling the pharmacokinetics, biodistribution, bioavailability and/or efficacy of the oligonucleotides. Accordingly, oligonucleotides described herein may be modified, e.g., comprise a modified sugar moiety, a modified internucleoside linkage, a modified nucleotide and/or combinations thereof. Any of the oligonucleotides disclosed herein may be linked to one or more other oligonucleotides disclosed herein by a linker, e.g., a cleavable linker.

Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the oligonucleotide modifications described herein can be combined with each other, and that one, two, three, four, five, or more different types of modifications can be included within the same molecule.

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often an oligonucleotide has one or more nucleotide analogues. For example, an oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. An oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues.

The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

In addition to conjugation to a sugar, folate or cell-penetrating peptide, the nucleic acid (e.g., oligonucleotide or mRNA) may be conjugated with a label. For example, the nucleic acid (e.g., oligonucleotide or mRNA) may be conjugated with a biotin moiety, cholesterol, Vitamin A, folate, sigma receptor ligands, aptamers, peptides, such as CPP, hydrophobic molecules, such as lipids, or ligands of the asialoglycoprotein receptor (ASGP-R).

ASGP-R is expressed in liver cells, including hepatocytes (see, e.g., Park et al. PNAS 2005, 102, 17125-17129). ASGP-R exhibits affinity for the sugar N-acetylgalactosamine (GalNAc), and GalNAc has therefore been used as a targeting moiety for the delivery of agents (e.g., oligonucleotides) to the liver (see, e.g., Winkler, J. Ther Deliv. 2013, 4, 791-809). In particular, agents comprising clusters of three GalNAc ligands are particularly effective binders to ASGP-R, resulting in improved cellular uptake of the agent (see, e.g., Khorev et al. Bioorganic and Medicinal Chemistry 2008, 16, 5216-5231). GalNAc-oligonucleotide conjugates have been used to target oligonucleotides to the liver, and to improve uptake of the oligonucleotides to liver cells. It has been found that the spacing of the sugars on multivalent GalNAc targeting ligands is crucial for effective binding to ASGP-R receptors. Therefore, the design of new GalNAc-based targeting ligands, and conjugates thereof, is of importance to drug delivery.

As described herein, a nucleic acid (e.g., oligonucleotide or mRNA) may comprise one or more modifications comprising: a modified sugar moiety, and/or a modified internucleoside linkage, and/or a modified nucleotide and/or combinations thereof. It is not necessary for all positions in a given nucleic acid (e.g., oligonucleotide or mRNA) to be uniformly modified, and in fact more than one of the modifications described herein may be incorporated in a single nucleic acid (e.g., oligonucleotide or mRNA) or even at within a single nucleoside within the nucleic acid.

In some embodiments, an oligonucleotide is a chimeric oligonucleotide that contains two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, an oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the nucleic acid (e.g., oligonucleotide or mRNA) into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see, e.g., De Mesmaeker et al. *Ace. Chem. Res.* 1995, 28, 366-374); morpholino backbones (see, e.g., Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see, e.g., Nielsen et al. *Science* 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in, e.g., Dwaine A. Braasch and David R. Corey, *Biochemistry* 2002, 41, 4503-4510; Genesis, volume 30, issue 3, 2001; Heasman, J., *Dev. Biol.* 2002, 243, 209-214; Nasevicius et al. *Nat. Genet.* 2000, 26, 216-220; Lacerra et al. *Proc. Natl. Acad. Sci.* 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, *Curr. Opin. Mol. Ther.* 2001, 3, 235-238; and Wang et al. *J. Gene Med.*, 2010, 12, 354-364; the disclosures of which are incorporated herein by reference in their entireties).

Cyclohexenyl nucleic acid oligonucleotide mimetics are described in Wang et al. *J.* Am. Chem. Soc. 2000, 122, 8595-8602.

Modified nucleic acid (e.g., oligonucleotide or mRNA) backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., *Biochem.* 2002, 41, 3457-3467; and Min et al. *Bioorg. Med. Chem. Lett.*, 2002, 12, 2651-2654; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al. *Nucleic Acid Res.* 2001, 1, 241-242; Surono et al., *Hum. Gene Ther.* 2004, 15, 749-757; Koizumi, *Curr. Opin. Mol. Ther.* 2006, 8, 144-149; and Horie et al. *Nucleic Acids Symp. Ser* (*Oxf*) 2005, 49, 171-172; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula:

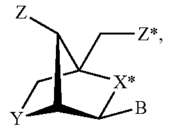

where X* and Y are independently selected from the groups —O—, —S—, —N(H)—, N(R)—, —$CH_2$— or —CH— (if part of a double bond), —$CH_2$—O—, —$CH_2$—S—, —$CH_2$—N(H)—, —$CH_2$—N(R)—, —$CH_2$—$CH_2$— or —$CH_2$—CH— (if part of a double bond), and —CH═CH—; where R is selected from hydrogen and $C_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the nucleic acids (e.g., oligonucleotides or mRNAs) described herein comprises at least one LNA unit according any of the formulas:

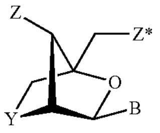
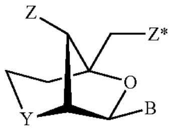
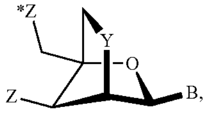

wherein Y is —O—, —S—, —NH—, or N($R^H$); Z and Z* are independently selected among an internucleoside linkage, a terminal group or a protecting group; B constitutes a natural or non-natural nucleotide base moiety, and RH is selected from hydrogen and $C_{1-4}$-alkyl. In some embodiments, the Locked Nucleic Acid (LNA) used in the nucleic acids (e.g., oligonucleotides or mRNAs) described herein comprises at least one Locked Nucleic Acid (LNA) unit according any of the formulas shown in Scheme 2 of PCT/DK2006/000512. In some embodiments, the LNA used in the nucleic acid (e.g., oligonucleotide or mRNA) of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$ O—, —O—P(O)$_2$—S—, —O—P(O,S)—S—, —S—P(O)$_2$—S—, —O—PO($R^H$)—O—, O—PO($OCH_3$)—O—, —O—PO($NR^H$)—O—, —O—PO($OCH_2CH_2S$—R)—O—, —O—PO($BH_3$)—O—, —O—PO($NHR^H$)—O—, —O—P(O)$_2$—$NR^H$—, —$NR^H$—P(O)$_2$—O—, —$NR^H$—CO—O—, where $R^H$ is selected from hydrogen and $C_{1-4}$-alkyl.

Other examples of LNA units are shown below:

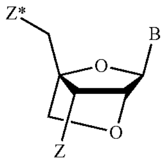

β-D-oxy-LNA

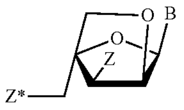

α-L-Oxy-LNA

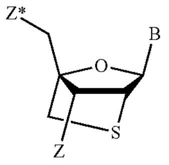

β-D-thio-LNA

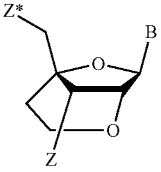

β-D-ENA

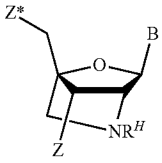

β-D-amino-LNA

The term "thio-LNA" comprises a locked nucleotide in which at least one of X or Y in the general formula above is selected from S or —$CH_2$—S—. Thio-LNA can be in both beta-D and alpha-L-configuration. The term "amino-LNA" comprises a locked nucleotide in which at least one of X or Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration. The term "oxy-LNA" comprises a locked nucleotide in which at least one of X or Y in the general formula above represents —O— or —$CH_2$—O—. Oxy-LNA can be in both beta-D and alpha-L-configuration. The term "ena-LNA" comprises a locked nucleotide in which Y in the general formula above is —$CH_2$—O— (where the oxygen atom of —$CH_2$—O— is attached to the 2'-position relative to the base B). LNAs are described in additional detail herein.

One or more substituted sugar moieties can also be included, e.g., one of the following at the 2' position: —OH; —SH; —$SCH_3$; —F; —OCN; —$OCH_3OCH_3$, —$OCH_3O(CH_2)_uCH_3$, —$O(CH_2)_uNH_2$ or —$O(CH_2)_uCH_3$, wherein u is an integer from 1 to 10, inclusive; $C_1$-$C_{10}$ alkyl; alkoxyalkoxy; substituted lower alkyl; alkaryl or aralkyl; —Cl; —Br; —CN; —$CF_3$; —$OCF_3$; O—, S—, or N-alkyl; O—, S—, or N-alkenyl; $SOCH_3$; $SO_2CH_3$; $ONO_2$; $NO_2$; $N_3$; $NH_2$; heterocyclylalkyl; heterocyclylalkylaryl; aminoalkylamino; polyalkylamino; substituted silyl; an RNA cleaving group; a reporter group; an intercalator; a group for improving the pharmacokinetic properties of a nucleic acid (e.g., oligonucleotide or mRNA); or a group for improving the pharmacodynamic properties of a nucleic acid (e.g., oligonucleotide or mRNA) and other substituents having similar properties. Modifications include 2'-methoxyethoxy [2'-O—$CH_2CH_2OCH_3$, also known as 2'-O-(2-methoxyethyl)](Martin et al. *Helv. Chim. Acta.* 1995, 78, 486). Other modifications include 2'-methoxy (2'-O—$CH_3$), 2'-propoxy (2'-$OCH_2$ $CH_2CH_3$) and 2'-fluoro (2'-F). Similar modifications may also be made at other positions on the nucleic acid (e.g., oligonucleotide or mRNA), particularly the 3' position of the sugar on the 3' terminal nucleotide and the 5' position of 5' terminal nucleotide. Nucleic acids (e.g., oligonucleotides or mRNAs) may also have sugar mimetics such as cyclobutyls in place of the pentofuranosyl group.

Nucleic acids (e.g., oligonucleotides or mRNAs) can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given nucleic acid (e.g., oligonucleotide or mRNA) to be uniformly modified, and in fact more than one of the modifications described herein may be incorporated in a single nucleic acid (e.g., oligonucleotide or mRNA) or even at within a single nucleoside within the nucleic acid.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in, e.g., Nielsen et al. *Science,* 1991, 254, 1497-1500.

Nucleic acids (e.g., oligonucleotides or mRNAs) can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al. *Angew. Chem. Int. Ed.* 1991, 30, 613; and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the nucleic acids (e.g., oligonucleotides or mRNAs) of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, in addition to the GalNAc-containing moiety, the nucleic acids (e.g., oligonucleotides or mRNAs) of the present invention are chemically linked to one or more moieties that enhance the activity, cellular distribution, or cellular uptake of the nucleic acid (e.g., oligonucleotide or mRNA). For example, one or more nucleic acids (e.g., oligonucleotides or mRNAs), of the same or different types, can be conjugated to each other; or nucleic acids (e.g., oligonucleotides or mRNAs) can be conjugated to targeting moieties with enhanced specificity for a cell type or tissue type. Such moieties include, but are not limited to, lipid moieties such as a cholesterol moiety (Letsinger et al. *Proc. Natl. Acad. Sci. USA* 1989, 86, 6553-6556), cholic acid (Manoharan et al. *Bioorg. Med. Chem. Let.* 1994, 4, 1053-1060), a thioether, e.g., hexyl-S-tritylthiol (Manoharan et al *Ann. N. Y. Acad. Sci.* 1992, 660, 306-309; Manoharan et al. *Bioorg. Med. Chem. Let.* 1993, 3, 2765-2770), a thiocholesterol (Oberhauser et al. *Nucl. Acids Res.* 1992, 20, 533-538), an aliphatic chain, e.g., dodecandiol or undecyl residues (Kabanov et al. *FEBS Lett.* 1990, 259, 327-330; Svinarchuk et al, *Biochimie* 1993, 75, 49-54), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651-3654; Shea et al. *Nucl. Acids Res.* 1990, 18, 3777-3783), a polyamine or a polyethylene glycol chain (Mancharan et al. *Nucleosides & Nucleotides,* 1995, 14, 969-973), or adamantane acetic acid (Manoharan et al. *Tetrahedron Lett.* 1995, 36, 3651-3654), a palmityl moiety (Mishra et al. *Biochim. Biophys. Acta* 1995, 1264, 229-237), or an octadecylamine or hexylamino-carbonyl-t oxycholesterol moiety (Crooke et al. *J.* Pharmacol. Exp. Ther. 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552;

5,567,810; 5,574,142; 5,585,481; 5,587,371; 5,595,726; 5,597,696; 5,599,923; 5,599,928 and 5,688,941, each of which is herein incorporated by reference.

Further examples of conjugate groups include intercalators, reporter molecules, polyamines, polyamides, polyethylene glycols, polyethers, groups that enhance the pharmacodynamic properties of nucleic acids (e.g., oligonucleotides or mRNAs), and groups that enhance the pharmacokinetic properties of nucleic acids (e.g., oligonucleotides or mRNAs). Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, nucleic acid (e.g., oligonucleotide or mRNA) modification includes modification of the 5' or 3' end of the nucleic acid (e.g., oligonucleotide or mRNA). In some embodiments, the 3' end of the nucleic acid (e.g., oligonucleotide or mRNA) comprises a hydroxyl group or a thiophosphate. In certain embodiments, the GalNAc targeting moiety is linked to the oligonucleotide through the 3' end of the nucleic acid (e.g., oligonucleotide or mRNA). In certain embodiments, the GalNAc targeting moiety is linked to the oligonucleotide through the 5' end of the nucleic acid (e.g., oligonucleotide or mRNA).

In some embodiments, a nucleic acid (e.g., oligonucleotide or mRNA) comprises locked nucleic acids (LNA), ENA modified nucleotides, 2'-O-methyl nucleotides, or 2'-fluoro-deoxyribonucleotides. In some embodiments, an oligonucleotide comprises alternating deoxyribonucleotides and 2'-fluoro-deoxyribonucleotides. In some embodiments, an oligonucleotide comprises alternating deoxyribonucleotides and 2-O-methyl nucleotides. In some embodiments, an oligonucleotide comprises alternating deoxyribonucleotides and ENA modified nucleotides. In some embodiments, an oligonucleotide comprises alternating deoxyribonucleotides and locked nucleic acid nucleotides. In some embodiments, an oligonucleotide comprises alternating locked nucleic acid nucleotides and 2'-O-methyl nucleotides.

In some embodiments, the 5' nucleotide of the nucleic acid (e.g., oligonucleotide or mRNA) is a deoxyribonucleotide. In some embodiments, the 5' nucleotide of the nucleic acid (e.g., oligonucleotide or mRNA) is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, a nucleic acid (e.g., oligonucleotide or mRNA) comprises phosphorothioate internucleotide linkages. In some embodiments, a nucleic acid (e.g., oligonucleotide or mRNA) comprises phosphorothioate internucleotide linkages between at least two nucleotides. In some embodiments, a nucleic acid (e.g., oligonucleotide or mRNA) comprises phosphorothioate internucleotide linkages between all nucleotides.

It should be appreciated that a nucleic acid (e.g., oligonucleotide or mRNA) can have any combination of modifications as described herein.

In some embodiments, an oligonucleotide described herein may be a mixmer or comprise a mixmer sequence pattern. The term 'mixmer' refers to oligonucleotides which comprise both naturally and non-naturally occurring nucleotides or comprise two different types of non-naturally occurring nucleotides. Mixmers are generally known in the art to have a higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Accordingly, in some embodiments, an oligonucleotide provided herein may be cleavage promoting (e.g., an siRNA or gapmer) or not cleavage promoting (e.g., a mixmer, siRNA, single stranded RNA or double stranded RNA).

In some embodiments, the mixmer comprises or consists of a repeating pattern of nucleotide analogues and naturally occurring nucleotides, or one type of nucleotide analogue and a second type of nucleotide analogue. However, it is to be understood that the mixmer need not comprise a repeating pattern and may instead comprise any arrangement of nucleotide analogues and naturally occurring nucleotides or any arrangement of one type of nucleotide analogue and a second type of nucleotide analogue. The repeating pattern, may, for instance be every second or every third nucleotide is a nucleotide analogue, such as LNA, and the remaining nucleotides are naturally occurring nucleotides, such as DNA, or are a 2' substituted nucleotide analogue such as 2'MOE or 2' fluoro analogues, or any other nucleotide analogues described herein. It is recognised that the repeating pattern of nucleotide analogues, such as LNA units, may be combined with nucleotide analogues at fixed positions—e.g. at the 5' or 3' termini.

In some embodiments, the mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive nucleotide analogues, such as at least two consecutive LNAs. In some embodiments, the mixmer comprises at least a region consisting of at least three consecutive nucleotide analogue units, such as at least three consecutive LNAs. In some embodiments, the mixmer does not comprise a region of more than 7, more than 6, more than 5, more than 4, more than 3, or more than 2 consecutive nucleotide analogues, such as LNAs. It is to be understood that the LNA units may be replaced with other nucleotide analogues, such as those referred to herein. In some embodiments, the mixmer contains a modified nucleotide, e.g., an LNA, at the 5' end. In some embodiments, the mixmer contains a modified nucleotide, e.g., an LNA, at the first two positions, counting from the 5' end.

In some embodiments, the mixmer is incapable of recruiting RNAseH. Oligonucleotides that are incapable of recruiting RNAseH are well known in the literature, in example see WO2007/112754, WO2007/112753, or PCT/DK2008/000344. Mixmers may be designed to comprise a mixture of affinity enhancing nucleotide analogues, such as in non-limiting example LNA nucleotides and 2'-O-methyl nucleotides. In some embodiments, the mixmer comprises modified internucleoside linkages (e.g., phosphorothioate internucleoside linkages or other linkages) between at least two, at least three, at least four, at least five or more nucleotides.

A mixmer may be produced using any method known in the art or described herein. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, the oligonucleotide is a gapmer. A gapmer oligonucleotide generally has the formula 5'-Xg-Yg-Zg-3', with Xg and Zg as flanking regions around a gap region Yg. In some embodiments, the Yg region is a contiguous stretch of nucleotides, e.g., a region of at least 6 DNA nucleotides, which are capable of recruiting an RNAse, such as RNAseH. Without wishing to be bound by theory, it is thought that the gapmer binds to the target nucleic acid, at which point an RNAse is recruited and can then cleave the target nucleic acid. In some embodiments, the Yg region is flanked both 5' and 3' by regions Xg and Zg comprising high-affinity modified nucleotides, e.g., 1-6 modified nucleotides. Exemplary modified oligonucleotides include, but are not limited to, 2' MOE or 2'OMe or Locked Nucleic Acid bases (LNA). The flanks Xg and Zg may be have a of length 1-20 nucleotides, preferably 1-8 nucleotides and even more preferred 1-5 nucleotides. The flanks Xg and Zg may be of similar length or of dissimilar lengths. The gap-segment Yg may be a nucleotide sequence of length 5-20 nucleotides, preferably 6-12 nucleotides and even more preferred 6-10 nucleotides. In some aspects, the gap region of the gapmer oligonucleotides of the invention may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using any method known in the art or described herein. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

In some embodiments, oligonucleotides provided herein may be in the form of small interfering RNAs (siRNA), also known as short interfering RNA or silencing RNA. SiRNA, is a class of RNA molecules (e.g., double stranded), typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using any method known in the art (see, e.g., PCT Publication Nos. WO08124927A1 and WO 2004/016735; and U.S. Patent Publication Nos. 2004/0077574 and 2008/0081791). A number of commercial packages and services are available that are suitable for use for the preparation of siRNA molecules. These include the in vitro transcription kits available from Ambion (Austin, TX) and New England Biolabs (Beverly, MA) as described above; viral siRNA construction kits commercially available from Invitrogen (Carlsbad, CA) and Ambion (Austin, TX), and custom siRNA construction services provided by Ambion (Austin, TX), Qiagen (Valencia, CA), Dharmacon (Lafayette, CO) and Sequitur, Inc (Natick, MA). A target sequence can be selected (and a siRNA sequence designed) using computer software available commercially (e.g. OligoEngine™ (Seattle, Wash.); Dharmacon, Inc. (Lafayette, Colo.); Target Finder from Ambion Inc. (Austin, Tex.) and the siRNA Design Tool from QIAGEN, Inc. (Valencia, Calif.)). In some embodiments, an siRNA may be designed or obtained using the RNAi atlas (available at the RNAiAtlas website), the siRNA database (available at the Stockholm Bioinformatics Website), or using DesiRM (available at the Institute of Microbial Technology website).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 200 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 200 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present invention comprises 3' overhangs of about 1 to about 3 nucleotides on both ends of the molecule.

In some embodiments, an oligonucleotide may be a microRNA (miRNA). MicroRNAs (referred to as "miRNAs") are small non-coding RNAs, belonging to a class of regulatory molecules found in plants and animals that control gene expression by binding to complementary sites on a target RNA transcript. miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34).

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides, although miRNAs of up to 2000 nucleotides can be utilized. In a preferred embodiment the size range of the miRNA is from 70 to 170 nucleotides in length. In another preferred embodiment, mature miRNAs of from 21 to 25 nucleotides in length can be used.

In some embodiments, the miRNA may be a miR-30 precursor. As used herein, an "miR-30 precursor", also called an miR-30 hairpin, is a precursor of the human microRNA miR-30, as it is understood in the literature (e.g., Zeng and Cullen, 2003; Zeng and Cullen, 2005; Zeng et al., 2005; United States Patent Application Publication No. US 2004/005341), where the precursor could be modified from the wild-type miR-30 precursor in any manner described or implied by that literature, while retaining the ability to be processed into an miRNA. In some embodiments, a miR-30 precursor is at least 80 nucleotides long and comprises a stem-loop structure. In some embodiments, the miR-30 precursor further comprises a first miRNA sequence of 20-22 nucleotides on the stem of the stem-loop structure complementary to a portion of a first target sequence.

A miRNA may be isolated from a variety of sources or may be synthesized according to methods well known in the art (see, e.g., Current Protocols in Molecular Biology, Wiley Online Library; U.S. Pat. No. 8,354,384; and Wahid et al. *Biochim Biophys Acta.* 2010, 1803, 1231-43). In some embodiments, a miRNA is expressed from a vector as known in the art or described herein. In some embodiments, the vector may include a sequence encoding a mature miRNA. In some embodiments, the vector may include a sequence encoding a pre-miRNA such that the pre-miRNA is expressed and processed in a cell into a mature miRNA. In some embodiments, the vector may include a sequence encoding a pri-miRNA. In this embodiment, the primary transcript is first processed to produce the stem-loop precursor miRNA molecule. The stem-loop precursor is then processed to produce the mature microRNA.

In some embodiments, oligonucleotides provided herein may be in the form of aptamers. An "aptamer" is any nucleic acid that binds specifically to a target, such as a small molecule, protein, nucleic acid, cell, tissue or organism. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof.

Selection of nucleic acid aptamers may be accomplished by any suitable method known in the art, including an optimized protocol for in vitro selection, known as SELEX (Systemic Evolution of Ligands by Exponential enrichment). Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (*J. Am. Chem. Soc.* 1993, 115, 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (*Biochem.* 1993, 32, 1751-1758; *Nucleic Acids Res.* 1993, 21, 2585-2589) replaced the six nucleotide loop of the TAR ribozyme hairpin with non-nucleotidic, ethylene glycol-related linkers. Thomson et al. (*Nucleic Acids Res.* 1993, 21, 5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

In certain embodiments, an oligonucleotide is one provided in U.S. patent application publication numbers US 2015/0252364, US 2015/0133362, US 2015/0050738; or international publication number WO 2015/051283; the entire contents of each of which is incorporated herein by reference.

It is to be understood that any oligonucleotide provided or described herein may be excluded from the invention.

Group Z

Group Z is a sugar, a folate or a cell-penetrating peptide in the conjugates and compounds described herein. In a particular embodiment, Z is a sugar. In another particular embodiment, Z is a folate. In another particular embodiment, Z is a cell-penetrating peptide.

As used herein, a "sugar" may be a naturally-occurring monosaccharide. In an embodiment, the sugar is an aldohexose (e.g., a pyranose or a furanose) or a ketohexose. In an embodiment, the sugar is a non-natural monosaccharide. In an embodiment, the sugar interacts with a receptor on the surface of a cell. In a particular embodiment, the sugar is mannose. In another particular embodiment, the sugar is GalNAc.

In an embodiment, the sugar has a receptor on a target cell surface. For example, the mannose receptor (Cluster of Differentiation 206, CD206) is a C-type lectin primarily present on the surface of macrophages and immature dendritic cells, but is also expressed on the surface of skin cells such as human dermal fibroblasts and keratinocytes. It is the first member of a family of endocytic receptors that includes Endo180 (CD280), M-type PLA2R, and DEC-205 (CD205).

As used herein, a "folate" is folic acid, or an ester or amide thereof. Based on the natural high affinity of folate for the folate receptor protein (FR), which is commonly expressed on the surface of many cells, including those of human cancers, folate conjugates also bind tightly to the FR and trigger cellular uptake via endocytosis.

As used herein, a "cell-penetrating peptide" is a peptide that facilitates cellular uptake of a conjugated "payload" molecule. Non-limiting examples of cell-penetrating peptides include

KFF (KFFKFFKFFK (SEQ ID NO: 1)),

ANT (RQIKIWFQNRRMKWKK (SEQ ID NO: 2)),

TAT (GRKKKRRQRRRYK (SEQ ID NO: 3)), (RXR)4XB (RXRRXRRXRRXRXB (SEQ ID NO: 4)), (RFR)4XB (RFRRFRRFRRFRXB (SEQ ID NO: 5)),

PKFF (KFFKFFKFFK (SEQ ID NO: 1)-O-cgatcattcaaa (SEQ ID NO: 6)-$NH_2$),

PANT (RQIKIWFQNRRMKWKK (SEQ ID NO: 2)-O-cgatcattcaaa (SEQ ID NO: 6)-$NH_2$),

PTAT (GRKKKRRQRRRYK (SEQ ID NO: 3)-O-cgatcattcaaa (SEQ ID NO: 6)-$NH_2$),

PRXR (RXRRXRRXRRXRXB (SEQ ID NO: 4)-O-cgatcattcaaa (SEQ ID NO: 6)-$NH_2$), and

PRFR (RFRRFRRFRRFRXB (SEQ ID NO: 5)-O-cgatcattcaaa (SEQ ID NO: 6)-$NH_2$).

Group X

As generally defined herein, X is S or O. In certain embodiments, X is O. In other embodiments, X is S.

Linkers L', L'', $L^1$, $L^2$, $L^3$, $L^{3'}$

As generally defined herein, L', L'', $L^1$, $L^2$, $L^3$ and $L^{3'}$ are each independently a bond, optionally substituted alkylene, or optionally substituted heteroalkylene.

In certain embodiments, at least one instance of $L^1$ is a bond. In certain embodiments, at least one instance of $L^1$ is optionally substituted alkylene. In certain embodiments, at least one instance of $L^1$ is optionally substituted $C_{1-20}$ alkylene. In certain embodiments, at least one instance of $L^1$ is optionally substituted $C_{1-10}$ alkylene. In certain embodiments, at least one instance of $L^1$ is optionally substituted $C_{1-6}$ alkylene. In certain embodiments, at least one instance of $L^1$ is unsubstituted alkylene. In certain embodiments, at least one instance of $L^1$ is optionally substituted heteroalkylene. In certain embodiments, at least one instance of $L^1$ is optionally substituted $C_{1-20}$ heteroalkylene. In certain embodiments, at least one instance of $L^1$ is optionally substituted $C_{1-10}$ heteroalkylene. In certain embodiments, at least one instance of $L^1$ is optionally substituted $C_{1-6}$ heteroalkylene. An optionally substituted heteroalkylene linker may contain one or more esters, amides, carbonates, carbamates, phosphodiesters, phosphorothioates, ureas, or other heteroatom-containing groups, in the linker. In certain embodiments, at least one instance of $L^1$ is substituted $C_{1-20}$ heteroalkylene. In certain embodiments, at least one instance of $L^1$ is substituted $C_{1-10}$ heteroalkylene. In certain embodiments, at least one instance of $L^1$ is substituted $C_{1-6}$ heteroalkylene. For example, in certain embodiments, at least one instance of $L^1$ is of the formula:

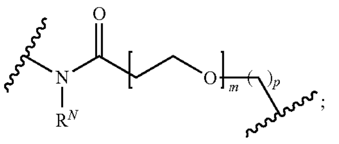

wherein $R^N$, m, and p are as defined herein. In certain embodiments, at least one instance of $L^1$ is of the formula:

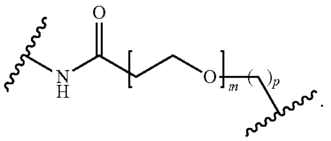

In certain embodiments, at least one instance of $L^1$ is of the formula:

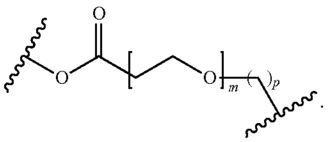

In certain embodiments, at least one instance of $L^1$ is of the formula:

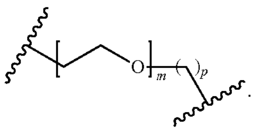

In certain embodiments, at least one instance of $L^1$ is of the formula:

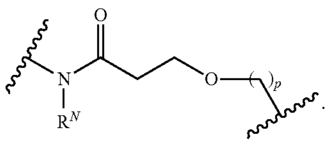

In certain embodiments, at least one instance of $L^1$ is of the formula:

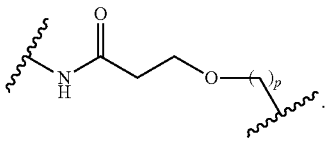

In certain embodiments, at least one instance of $L^1$ is of the formula:

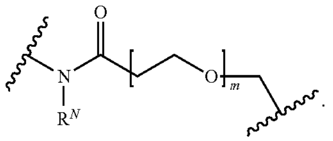

In certain embodiments, at least one instance of $L^1$ is of the formula:

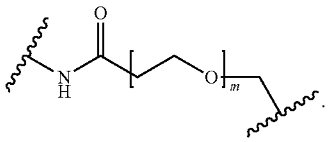

In certain embodiments, at least one instance of $L^1$ is of the formula:

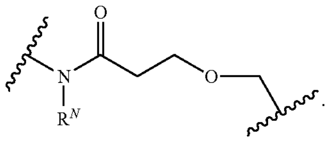

In certain embodiments, at least one instance of $L^1$ is of the formula:

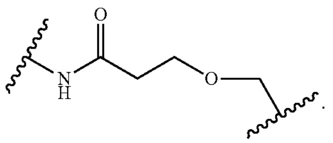 [SMILES: *COCCC(=O)N*]

In certain embodiments, each instance of $L^1$ is of the formula:

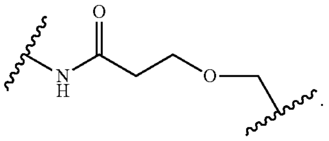 [SMILES: *COCCC(=O)N*]

In certain embodiments, each instance of $L^1$ comprises a triazole. The triazole may be the 1,4 isomer or the 1,5 isomer:

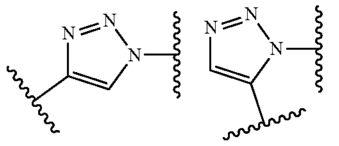

1,4 1,5

In a particular embodiment, each instance of $L^1$ is of the following formula:

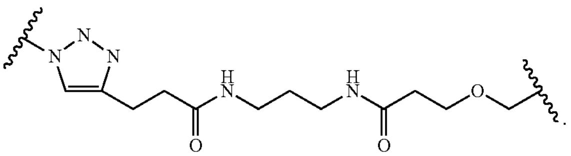 [SMILES: *COCCC(=O)NCCCNC(=O)CCC1=CN(*)NN1]

In certain embodiments, L' and L" are independently a bond, optionally substituted alkylene (e.g., optionally substituted $C_{1-20}$ alkylene, optionally substituted $C_{1-10}$ alkylene, optionally substituted $C_{1-6}$ alkylene, or unsubstituted alkylene). In certain embodiments, at least one instance of L' and L" is optionally substituted heteroalkylene. In certain embodiments, at least one instance of L' and L" is optionally substituted $C_{1-20}$ heteroalkylene. In certain embodiments, at least one instance of L' and L" is optionally substituted $C_{1-10}$ heteroalkylene. In certain embodiments, at least one instance of L' and L" is optionally substituted $C_{1-6}$ heteroalkylene. An optionally substituted heteroalkylene linker may contain one or more esters, amides, carbonates, carbamates, phosphodiesters, phosphorothioates, ureas, or other heteroatom-containing groups, in the linker. In certain embodiments, at least one instance of L' and L" is substituted $C_{1-20}$ heteroalkylene. In certain embodiments, at least one instance of L' and L" is substituted $C_{1-10}$ heteroalkylene. In certain embodiments, at least one instance of L' and L" is substituted $C_{1-6}$ heteroalkylene. For example, in certain embodiments, at least one instance of L' and L" is of the formula:

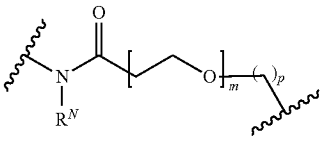

;

wherein $R^N$, m, and p are as defined herein. In certain embodiments, at least one instance of L' and L" is of the formula:

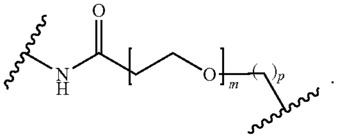

In certain embodiments, at least one instance of L' and L" is of the formula:

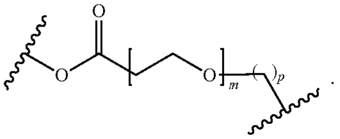

In certain embodiments, at least one instance of L' and L" is of the formula:

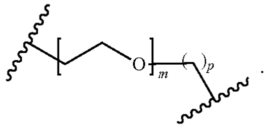

In certain embodiments, at least one instance of L' and L" is of the formula:

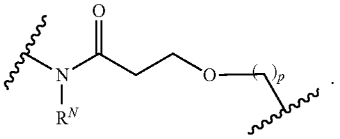

In certain embodiments, at least one instance of L' and L" is of the formula:

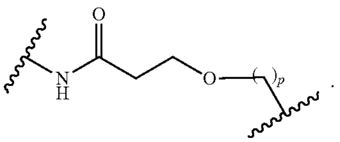

In certain embodiments, at least one instance of L' and L" is of the formula:

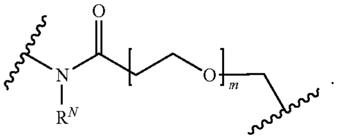

In certain embodiments, at least one instance of L' and L" is of the formula:

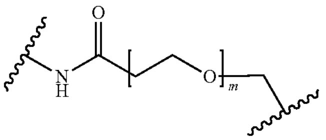.

In certain embodiments, at least one instance of L' and L" is of the formula:

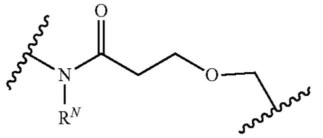.

In certain embodiments, at least one instance of L' and L" is of the formula:

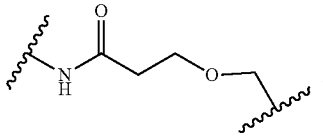.

In certain embodiments, each instance of L' and L" is of the formula:

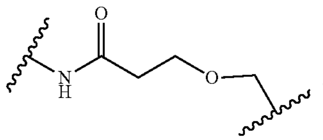.

In certain embodiments, $L^2$ is a bond. In certain embodiments, $L^2$ is optionally substituted alkylene. In certain embodiments, $L^2$ is branched. In certain embodiments, $L^2$ comprises a cycloalkyl or heterocycloalkyl branch point. In certain embodiments, $L^2$ comprises an aryl or heteroaryl branch point. In certain embodiments, $L^2$ comprises a cycloalkyl moiety. In certain embodiments, $L^2$ is optionally substituted $C_{1-20}$ alkylene. In certain embodiments, $L^2$ is optionally substituted $C_{1-10}$ alkylene. In certain embodiments, $L^2$ is optionally substituted $C_{1-6}$ alkylene. In certain embodiments, $L^2$ is unsubstituted alkylene. In certain embodiments, $L^2$ is optionally substituted heteroalkylene. In certain embodiments, $L^2$ is optionally substituted $C_{1-20}$ heteroalkylene. In certain embodiments, $L^2$ is optionally substituted $C_{1-10}$ heteroalkylene. In certain embodiments, $L^2$ is optionally substituted $C_{1-6}$ heteroalkylene. An optionally substituted heteroalkylene linker may contain one or more esters, amides, carbonates, carbamates, ureas, phosphodiesters, phosphorothioates, or other heteroatom-containing groups, in the linker. In certain embodiments, $L^2$ is substituted $C_{1-20}$ heteroalkylene. In certain embodiments, $L^2$ is substituted $C_{1-10}$ heteroalkylene. In certain embodiments, $L^2$ is substituted $C_{1-6}$ heteroalkylene. For example, in certain embodiments, $L^2$ is of the formula:

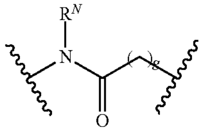;

wherein $R^N$ and q are as defined herein. In certain embodiments, $L^2$ is of the formula:

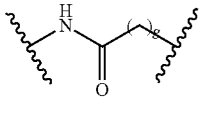.

In certain embodiments, $L^2$ is of the formula:

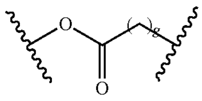.

In certain embodiments, $L^2$ is of one of the following formulae:

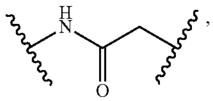, 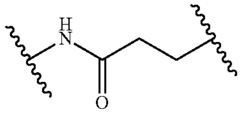,

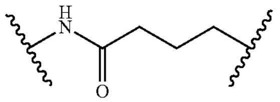,

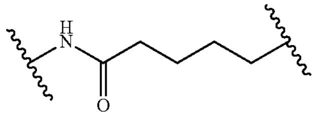,

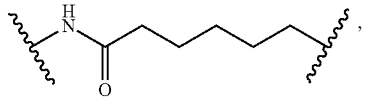,

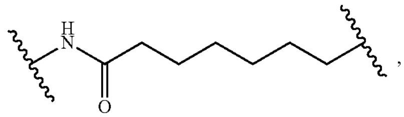,

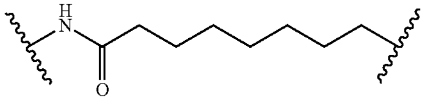,

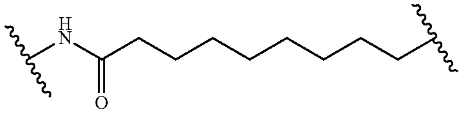,

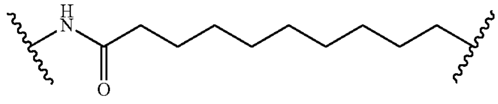.

In certain embodiments, $L^2$ is of the formula:

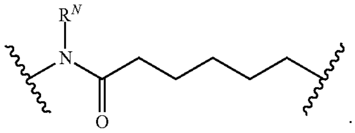.

In certain embodiments, $L^2$ is of the formula:

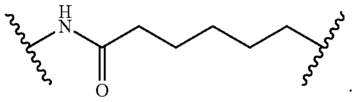 [SMILES: *CCCCCC(=O)N*].

In certain embodiments, $L^3$ is a bond. In certain embodiments, $L^3$ is optionally substituted alkylene. In certain embodiments, $L^3$ is optionally substituted $C_{1-20}$ alkylene. In certain embodiments, $L^3$ is optionally substituted $C_{1-10}$ alkylene. In certain embodiments, $L^3$ is optionally substituted $C_{1-6}$ alkylene. In certain embodiments, $L^3$ is unsubstituted alkylene. In certain embodiments, $L^3$ is unsubstituted $C_{1-20}$ alkylene. In certain embodiments, $L^3$ is unsubstituted $C_{1-10}$ alkylene. In certain embodiments, $L^3$ is unsubstituted $C_{1-6}$ alkylene. In certain embodiments, $L^3$ is optionally substituted heteroalkylene. In certain embodiments, $L^3$ is optionally substituted $C_{1-20}$ heteroalkylene. In certain embodiments, $L^3$ is optionally substituted $C_{1-10}$ heteroalkylene. In certain embodiments, $L^3$ is optionally substituted $C_{1-6}$ heteroalkylene. For example, in certain embodiments, $L^3$ is of the formula:

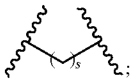;

wherein s is as defined herein. In certain embodiments, $L^3$ is of one of the following formulae:

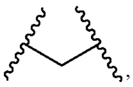, 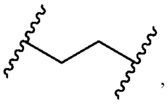, 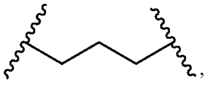,

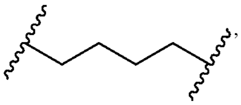, 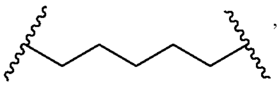,

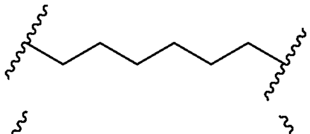,

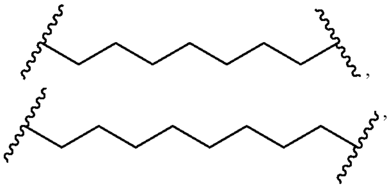,

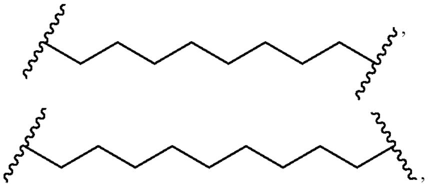,

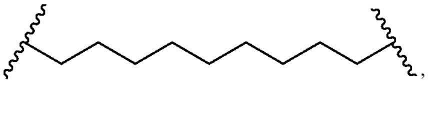,

-continued

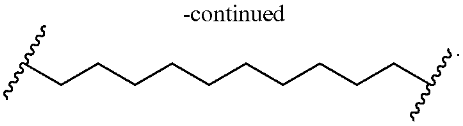.

In certain embodiments, $L^3$ is of the following formula:

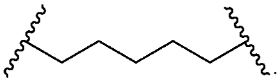 [SMILES: *CCCCC*].

In certain embodiments, $L^{3'}$ is a bond. In certain embodiments, $L^{3'}$ is optionally substituted alkylene. In certain embodiments, $L^{3'}$ is optionally substituted $C_{1-20}$ alkylene. In certain embodiments, $L^{3'}$ is optionally substituted $C_{1-10}$ alkylene. In certain embodiments, $L^3$ is optionally substituted $C_{1-6}$ alkylene. In certain embodiments, $L^{3'}$ is unsubstituted alkylene. In certain embodiments, $L^3$ is unsubstituted $C_{1-20}$ alkylene. In certain embodiments, $L^{3'}$ is unsubstituted $C_{1-10}$ alkylene. In certain embodiments, $L^{3'}$ is unsubstituted $C_{1-6}$ alkylene. In certain embodiments, $L^{3'}$ is optionally substituted heteroalkylene. An optionally substituted heteroalkylene linker may contain one or more esters, amides, carbonates, carbamates, phosphodiesters, phosphorothioates, phosphoramidites, phosphoramidates, ureas, or other heteroatom-containing groups, in the linker. In certain embodiments, $L^3$ is optionally substituted $C_{1-20}$ heteroalkylene. In certain embodiments, $L^{3'}$ is optionally substituted $C_{1-10}$ heteroalkylene. In certain embodiments, $L^{3'}$ is optionally substituted $C_{1-6}$ heteroalkylene.

In an embodiment, $L^{3'}$ comprises a moiety that is enzymatically cleavable (e.g., by a nuclease or protease). In a particular embodiment, the moiety is cleavable by an endopeptidase such as trypsin, chymotrypsin, elastase, thermolysin, pepsin, endopeptidase V8. cathepsin B, cathepsin D, cathepsin L, cathepsin C, papain, cathepsin S or endosomal acidic insulinase.

In an embodiment, $L^{3'}$ comprises comprises a moiety that is labile to low pH, such as imine, a carbamate, a diorthoester, a polyphosphoester, a polyphosphazene, an acetal, a vinyl ether, a hydrazone, an azidomethyl-methylmaleic anhydride, a thiopropionate, a masked endosomolytic agent or a citraconyl group.

$R^O$ and $R^N$

As generally defined herein, each instance of $R^N$ is independently hydrogen, optionally substituted alkyl; optionally substituted acyl; or a nitrogen protecting group. In certain embodiments, at least one instance of $R^N$ is hydrogen. In certain embodiments, at least one instance of $R^N$ is optionally substituted alkyl. In certain embodiments, at least one instance of $R^N$ is optionally substituted acyl. In certain embodiments, at least one instance of $R^N$ is a nitrogen protecting group. In certain embodiments, each instance of $R^N$ is hydrogen.

As geerally defined herein, each instance of $R^O$ is independently hydrogen, optionally substituted alkyl; optionally substituted acyl; or an oxygen protecting group. In certain embodiments, at least one instance of $R^O$ is hydrogen. In certain embodiments, each instance of $R^O$ is hydrogen. In certain embodiments, at least one instance of $R^O$ is optionally substituted alkyl. In certain embodiments, at least one instance of $R^O$ is optionally substituted acyl. In certain embodiments, at least one instance of $R^O$ is an oxygen protecting group. In certain embodiments, each instance of $R^O$ is an oxygen protecting group. In certain embodiments, at least one instance of $R^O$ is optionally substituted —C(=O)alkyl or —C(=O)aryl (e.g., —C(=O)phenyl). In certain embodiments, at least one instance of $R^O$ is optionally substituted —C(=O)$C_{1-6}$ alkyl. In certain embodiments, at least one instance of $R^O$ is unsubstituted —C(=O)$C_{1-6}$ alkyl. In certain embodiments, at least one instance of $R^O$ is optionally substituted —C(=O)$C_{1-3}$ alkyl. In certain embodiments, at least one instance of $R^O$ is unsubstituted —C(=O)$C_{1-3}$ alkyl. In certain embodiments, at least one instance of $R^O$ is —C(=O)$CH_3$ (acetyl). In certain embodiments, each instance of $R^O$ is —C(=O)$CH_3$.

n, m, p, q, and s

As generally defined herein, n is an integer from 1 to 10, inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

As generally defined herein, m is an integer from 0 to 10, inclusive. In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10.

As generally defined herein, p is an integer from 0 to 10, inclusive. In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

As generally defined herein, q is an integer from 0 to 20, inclusive. In certain embodiments, q is 0. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10. In certain embodiments, q is 11. In certain embodiments, q is 12. In certain embodiments, q is 13. In certain embodiments, q is 14. In certain embodiments, q is 15. In certain embodiments, q is 16. In certain embodiments, q is 17. In certain embodiments, q is 18. In certain embodiments, q is 19. In certain embodiments, q is 20.

As generally defined herein, s is an integer from 0 to 20, inclusive. In certain embodiments, s is 0. In certain embodiments, s is 1. In certain embodiments, s is 2. In certain embodiments, s is 3. In certain embodiments, s is 4. In certain embodiments, s is 5. In certain embodiments, s is 6. In certain embodiments, s is 7. In certain embodiments, s is 8. In certain embodiments, s is 9. In certain embodiments, s is 10. In certain embodiments, s is 11. In certain embodiments, s is 12. In certain embodiments, s is 13. In certain embodiments, s is 14. In certain embodiments, s is 15. In certain embodiments, s is 16. In certain embodiments, s is 17. In certain embodiments, s is 18. In certain embodiments, s is 19. In certain embodiments, s is 20.

Formulation, Delivery, and Dosing

The conjugates and compounds described herein can be formulated for administration to a subject for treating and/or preventing a disease or condition. The formulations may conveniently be presented in unit dosage form and may be prepared by any methods well known in the art of pharmacy. The amount of active ingredient (e.g., nucleic acid such as oligonucleotide or mRNA, compound, or conjugate of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated composition can assume a variety of states. In some examples, the composition is at least partially crystalline, uniformly crystalline, and/or anhydrous (e.g., less than 80, 50, 30, 20, or 10% water). In another example, a conjugate or compound is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, a composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A conjugate or compound preparation can be formulated or administered (together or separately) in combination with another agent, e.g., another therapeutic agent or an agent that stabilizes a conjugate or compound, e.g., a protein that complexes with a nucleic acid (e.g., oligonucleotide or mRNA). Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, a conjugate preparation includes a second nucleic acid (e.g., oligonucleotide or mRNA), e.g., a second oligonucleotide that modulates expression of a second gene or a second oligonucleotide that modulates expression of the first gene. Still other preparation can include at least 3, 5, ten, twenty, fifty, or a hundred or more different nucleic acid (e.g., oligonucleotide or mRNA) species. Such nucleic acids (e.g., oligonucleotides or mRNAs) can mediated gene expression with respect to a similar number of different genes. In one embodiment, a conjugate or compound preparation includes at least a second therapeutic agent (e.g., an agent other than an oligonucleotide).

Any of the formulations, excipients, vehicles, etc. disclosed herein may be adapted or used to facilitate delivery of a conjugate or compound to a cell. Formulations, excipients, vehicles, etc. disclosed herein may be adapted or used to facilitate delivery of a conjugate or compound to a cell in vitro or in vivo. For example, a conjugate or compound may be formulated with a nanoparticle, poly(lactic-co-glycolic acid) (PLGA) microsphere, lipidoid, lipoplex, liposome, polymer, carbohydrate (including simple sugars), cationic lipid, a fibrin gel, a fibrin hydrogel, a fibrin glue, a fibrin sealant, fibrinogen, thrombin, rapidly eliminated lipid nanoparticles (reLNPs) and combinations thereof. In some embodiments, a conjugate or compound may be delivered to a cell gymnotically.

A conjugate or compound of the invention can be incorporated into pharmaceutical compositions suitable for administration. Such compositions typically include one or more conjugates or compounds of the present invention, and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A composition that includes conjugate or compound described herein can be delivered to a subject by a variety of routes. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration. A "therapeutically effective amount" of a compound described herein is an amount sufficient to provide a therapeutic benefit in the treatment of a condition or to delay or minimize one or more symptoms associated with the condition. The term "physiologically effective amount" is that amount delivered to a subject to give the desired palliative or curative effect.

The term "pharmaceutically acceptable carrier" means that the carrier can be administered to a subject with no significant adverse toxicological effects to the subject.

The route and site of administration may be chosen to enhance targeting. For example, to target muscle cells, intramuscular injection into the muscles of interest would be a logical choice. Lung cells might be targeted by administering a conjugate or compound in aerosol form. The vascular endothelial cells could be targeted by coating a balloon catheter with a conjugate or compound and mechanically introducing the conjugate or compound.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver a conjugate or compound to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, conjugates or compounds administered through these membranes may have a rapid onset of action, provide therapeutic plasma levels, avoid first pass effect of hepatic metabolism, and avoid exposure of the nucleic acids (e.g., oligonucleotides or mRNAs) to the hostile gastrointestinal (GI) environment. Additional advantages include easy access to the membrane sites so that the conjugate or compound can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of a conjugate or compound may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the conjugates or compounds described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. A nucleic acid (e.g., oligonucleotide or mRNA) can also be administered to the interior of the eye, and can be introduced by a needle or other delivery device which can introduce it to a selected area or structure.

Pulmonary delivery compositions can be delivered by inhalation by the patient of a dispersion so that the composition, preferably conjugates or compounds, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A nucleic acid (e.g., oligonucleotide or mRNA) composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 μm in diameter preferably with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar nucleic acid (e.g., oligonucleotide or mRNA) formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a conjugate or compound, e.g., a device can release insulin.

In one embodiment, unit doses or measured doses of a composition that includes a conjugate or compound are dispensed by an implanted device. The device can include a sensor that monitors a parameter within a subject. For example, the device can include pump, e.g., and, optionally, associated electronics.

Tissue, e.g., cells or organs can be treated with a conjugate or compound, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, nucleic acid (e.g., oligonucleotide or mRNA) treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a nucleic acid (e.g., oligonucleotide or mRNA).

Exemplary devices include condoms, diaphragms, IUD (implantable uterine devices, sponges, vaginal sheaths, and birth control devices.

In one aspect, the invention features a method of administering an conjugate or compound (e.g., as a compound or as a component of a composition) to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with low/high levels of an RNA or protein. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a conjugate or compound. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the nucleic acid (e.g., oligonucleotide or mRNA) may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some cases, a patient is treated with an conjugate or compound in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of a conjugate or compound composition is an amount sufficient to be effective in treating or preventing a disorder or to regulate a physiological condition in humans. The concentration or amount of a conjugate or compound administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a conjugate or compound can include a single treatment or, preferably, can include a series of treatments. It will also be appreciated that the effective dosage of a conjugate or compound used for treatment may increase or decrease over the course of a particular treatment. For example, the subject can be monitored after administering a conjugate or compound composition. Based on information from the monitoring, an additional amount of a nucleic acid (e.g., oligonucleotide or mRNA) composition can be administered.

Dosing is dependent on severity and responsiveness of the disease condition to be treated, with the course of treatment lasting from several days to several months, or until a cure is effected or a diminution of disease state is achieved. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models.

Methods of Treatment and Use

The present invention also provides methods of using the conjugates and compounds (e.g., GalNAc-nucleic acid conjugates such as conjugates of Formula (I)) described herein, and pharmaceutically acceptable salts, solvates, hydrates, polymorphs, co-crystals, tautomers, stereoisomers, isotopically labeled derivatives, and prodrugs thereof, and pharmaceutical compositions thereof, for the treatment and/or prevention of diseases or conditions. In certain embodiments, the disease or conditions is a genetic disease, proliferative disease (e.g., cancer), a disease associated with angiogenesis, a neoplasm, inflammatory disease, autoimmune disease, liver disease, spleen disease, pulmonary disease, hematological disease, neurological disease, painful condition, psychiatric disorder, ocular condition, cardiovascular disease, or metabolic disorder (e.g., a diabetic condition).

In certain embodiments, the method for treating a disease or condition in a subject in need thereof described herein comprises administering to a subject a therapeutically effective amount of a conjugate or compound described herein (e.g., a GalNAc-nucleic acid conjugate such as conjugate of Formula (I)), or a pharmaceutically acceptable salt, solvate, hydrate, polymorph, co-crystal, tautomer, stereoisomer, isotopically labeled derivative, or prodrug thereof, or a pharmaceutical composition thereof. A "therapeutically effective amount" of a compound described herein is an amount sufficient to provide a therapeutic benefit in the treatment of a condition or to delay or minimize one or more symptoms associated with the condition.

In another aspect, the present invention provides a method of preventing a disease or condition in a subject in need thereof, the method comprising administering to a subject a prophylactically effective amount compound of a conjugate or compound described herein (e.g., a GalNAc-nucleic acid conjugate such as conjugates of Formula (I)), or a pharmaceutically acceptable salt, solvate, hydrate, polymorph, co-crystal, tautomer, stereoisomer, isotopically labeled derivative, or prodrug thereof, or a pharmaceutical composition thereof. A "prophylactically effective amount" of a compound described herein is an amount sufficient to prevent a condition, or one or more symptoms associated with the condition or prevent its recurrence.

The present invention also provides methods for delivering a nucleic acid (e.g., oligonucleotide or mRNA) to a cell, the methods comprising contacting the cell with a conjugate described herein. In certain embodiments, the cell is contacted in vivo. In certain embodiments, the cell is contacted in vitro. In certain embodiments, the cell is contacted ex vivo.

The present invention also provides methods for delivering a nucleic acid (e.g., oligonucleotide or mRNA) to a subject, the methods comprising administering a conjugate as described herein to the subject.

The present invention also provides methods for modulating (e.g., increasing or decreasing as discussed below) gene expression in a subject or cell. The methods comprise administering to a subject and/or contacting a cell with a conjugate or compound described herein, or a pharmaceutically acceptable salt, solvate, hydrate, polymorph, co-crystal, tautomer, stereoisomer, isotopically labeled derivative, or prodrug thereof, or a pharmaceutical composition thereof.

In one aspect, the invention relates to methods for increasing gene expression in a cell for research purposes (e.g., to study the function of the gene in the cell that is silenced or downregulated). In another aspect, the invention relates to methods for increasing gene expression in a cell for therapeutic purposes (e.g., for the treatment or prevention of a disease described herein). The cells can be in vitro, ex vivo, or in vivo (e.g., in a subject in need thereof, such a as a subject who has a disease resulting from reduced expression or activity of a target gene). In some embodiments, methods for increasing gene expression in a cell comprise contacting the cell with a conjugate or compound described herein (e.g., a GalNAc-nucleic acid conjugate such as a conjugate of Formula (I)), or a pharmaceutically acceptable salt, solvate, hydrate, polymorph, co-crystal, tautomer, stereoisomer, isotopically labeled derivative, or prodrug thereof, or a pharmaceutical composition thereof. In some embodiments, gene expression is increased by at least 5%, 10%, 20%, 30%, 40%, 50%, 60%, 70%, 80%, 90%, 100%, 200% or more greater than gene expression in a control cell or control subject. An appropriate control cell or subject may be a cell, tissue or subject to which a conjugate to compound has not been delivered or to which a negative control has been delivered (e.g., a scrambled oligo, a carrier, etc.). In some embodiments, gene expression includes an increase of protein expression by at least 5%, 10%, 20%, 30%, 40%, 50%, 60%, 70%, 80%, 90%, 100%, 200%, or more, higher than the amount of a protein in the subject (e.g., in a cell or tissue of the subject) before administering a conjugate or compound or in a control subject which has not been administered the conjugate or compound or that has been administered a negative control.

In another aspect, the invention relates to methods for decreasing (e.g., mitigating, silencing) gene expression in a cell for research purposes (e.g., to study the function of the gene in the cell that is amplified or upregulated). In another aspect, the invention relates to methods for decreasing gene expression in a cell for therapeutic purposes (e.g., for the treatment or prevention of a disease described herein). The cells can be in vitro, ex vivo, or in vivo (e.g., in a subject in need thereof, such a as a subject who has a disease resulting from aberrant expression or activity of a target gene). In some embodiments, methods for decreasing gene expression in a cell comprise contacting the cell with a conjugate or compound described herein (e.g., a conjugate such as the conjugate of Formula (I-a)), or a pharmaceutically acceptable salt, solvate, hydrate, polymorph, co-crystal, tautomer, stereoisomer, isotopically labeled derivative, or prodrug thereof, or a pharmaceutical composition thereof. In some embodiments, gene expression is decreased by at least 5%, 10%, 20%, 30%, 40%, 50%, 60%, 70%, 80%, 90%, 100%, 200% or compared to gene expression in a control cell or control subject. An appropriate control cell or subject may be a cell, tissue or subject to which a conjugate to compound has not been delivered or to which a negative control has been delivered (e.g., a scrambled oligo, a carrier, etc.). In some embodiments, gene expression includes an decrease of protein expression by at least 5%, 10%, 20%, 30%, 40%, 50%, 60%, 70%, 80%, 90%, 100%, 200%, or more, less than the amount of a protein in the subject (e.g., in a cell or tissue of the subject) before administering a conjugate or compound or in a control subject which has not been administered the conjugate or compound or that has been administered a negative control.

In certain embodiments, the methods described herein include contacting a biological sample with a compound or conjugate described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include contacting a target tissue with a compound or conjugate described herein, or a pharmaceutically acceptable salt, solvate, hydrate, polymorph, co-crystal, tautomer, stereoisomer, isotopically labeled derivative, or prodrug thereof, or a pharmaceutical composition thereof.

A conjugate, compound, or composition provided herein may be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. In certain embodiments, the compounds, conjugates, or pharmaceutical compositions described herein can be administered in combination with an anti-cancer therapy including, but not limited to, surgery, radiation therapy, transplantation (e.g., stem cell transplantation, bone marrow transplantation), immunotherapy, and chemotherapy.

EXAMPLES

These and other aspects of the present invention will be further appreciated upon consideration of the following Examples, which are intended to illustrate certain particular embodiments of the invention but are not intended to limit its scope, as defined by the claims.

Synthesis of Trivalent GalNAc-Conjugated RaNA-Oligonucleotides

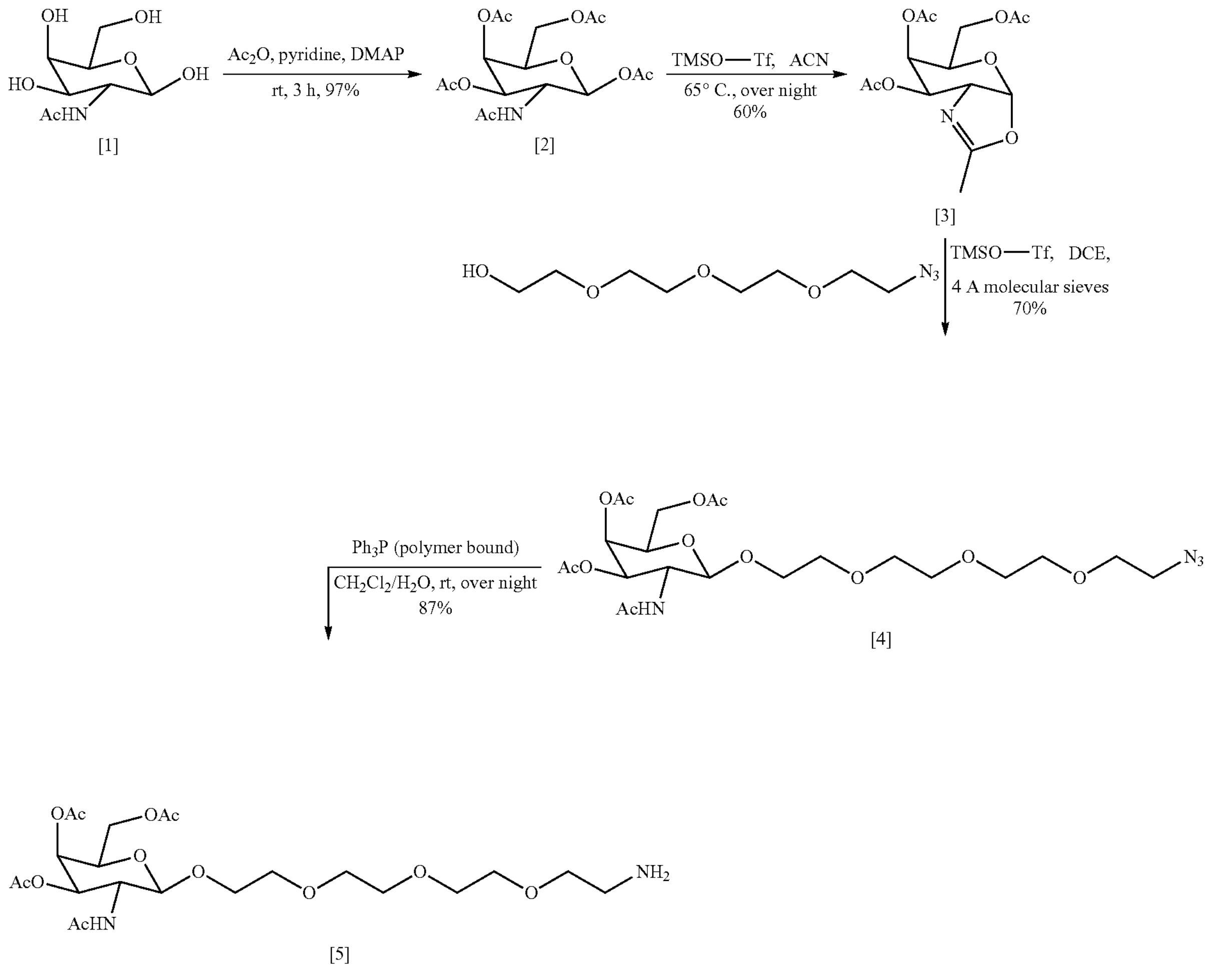

Synthesis of Acetylated GalNAc [2]

See, e.g., Guo, et. al. *Bioconjug. Chem.* 2006, 17, 1537-1544. GalNAc (10 g, 45.2 mmol) was dissolved in pyridine (100 mL). DMAP (1.4 g, 11.3 mmol) was added in it. Acetic anhydride (46.2 mL, 452 mmol) was added into the reaction mixture and stirred for next three hours. Reaction was completed within three hours based on TLC. After completion of reaction the crude mixture was evaporated off to dryness and purified via column chromatography (0-100% Ethyl acetate in Pet ether). The product comes at 100% Ethyl acetate. Pure product (17 g, 97%) was isolated as white foam and characterized based on Mass analysis. Results: ESI-MS analysis: Calculated $C_{16}H_{23}NO_{10}$. $Na^+$, $[M+Na^+]=412.13$, Observed=412.12.

Synthesis of Oxazoline [3]

See, e.g., Guo, et. al. *Bioconjug. Chem.* 2006, 17, 1537-1544; Manoharan, et.al. *J. Am. Chem. Soc.* 2014, 136, 16958-16961. Compound 2 (17 g, 43.7 mmol) was dissolved in anhydrous acetonitrile (100 mL). 4 Å molecular sieves were added in to the reaction mixture to keep it under complete anhydrous condition. Reaction mixture was cooled to zero degree and TMSOTf (11.84 mL, 65.5 mmol) was added in it. Reaction was then slowly warmed up to room temperature and then heated to 65° C. over night. After completion of reaction, triethylamine (~17 mL) was added to quench the reaction. Molecular sieves were filtered off and the reaction mixture was evaporated off to dryness. It was then diluted with ethyl acetate (~250 mL). Organic layer was washed with sodium bicarbonate (3×100 mL) and with brine solution (2×100 mL). Organic layer was dried over anhydrous sodium sulfate and evaporated off to obtain a crude product (12.6 g) as brown color foam. MS analysis confirmed the formation of desired oxazoline derivative 3. The crude mixture was taken into the next step without further purification. Results: ESI-MS analysis: Calculated $C_{14}H_{19}NO_8$, $[M+H^+]=329.10$, Observed=329.0.

Synthesis of [4]

See, e.g., Guo, et. al. *Bioconjug. Chem.* 2006, 17, 1537-1544; Manoharan, et.al. *J. Am. Chem. Soc.* 2014, 136, 16958-16961. Compound 3 (9.0 g, 27.3 mol) was co-evaporated with 1,2-dichloroethane (3×50 mL) and then re-dissolved in to the same solvent (250 mL). Reaction mixture was then stirred with 4 Å molecular sieves (2 g) for 5 min at room temperature. Azido-dPEG$_4$-OH (6.59 g, 30.1 mmol) was added and stirring was continued for 30 min. TMS-triflate (2.5 mL, 13.7 mmol) was added drop-wise under constant stirring over 10 min. Stirring was continued over night at 45° C. followed by quenching with saturated $NaHCO_3$ solution (100 mL). The organic layer was separated, diluted with dichloromethane 200 mL, and washed with water (2×100 mL) and brine (2×100 mL) solution. Finally, the organic layer was dried over anhydrous $Na_2SO_4$, and evaporated to dryness under reduced pressure. The crude product was purified via column chromatography (1-2% methanol in dichloromethane). Pure product 4 (10.5 g, 70%) was isolated as light yellow oil and characterized based on Mass and $^1$HNMR analysis. Results: ESI-MS analysis: Calculated $C_{22}H_{36}N_4O_{12}$. $Na^+$, [M+$Na^+$]=571.22, Observed=571.20.

Synthesis of [5]

To a stirred solution of compound 4 (2.3 g, 41.9 mmol) in dichloromethane (50 mL), polymer bound triphenylphosphine (6.60 g, 83.9 mmol, loading 3 mmol/g) was added at room temperature and stirred for 2 h. Water (2.3 mL, 126 mmol) was added into the reaction mixture and continued for another 3 h at room temperature. After completion of reaction the crude mixture was filtered off and evaporated to complete dryness under high vacuum to obtain compound 5 (1.9 g, 87%) as a pale yellow sticky solid. Compound 5 was taken to the next step almost immediately without further purification. Compound 5 was characterized based on mass analysis. Results: ESI-MS analysis: Calculated $C_{22}H_{39}N_2O_{12}$, [M+$H^+$]=523.25, Observed=523.20.

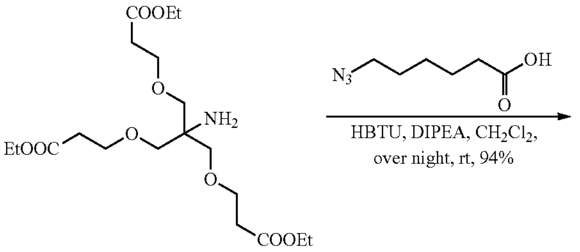

[6]

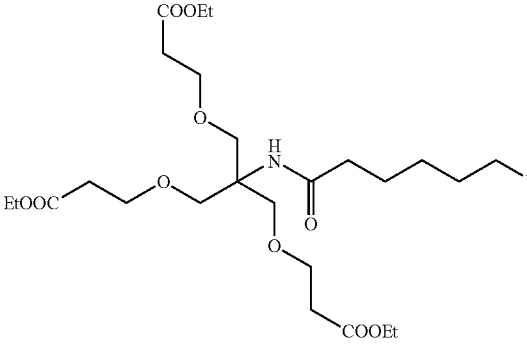

[7]

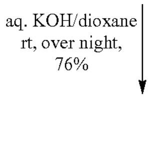

-continued

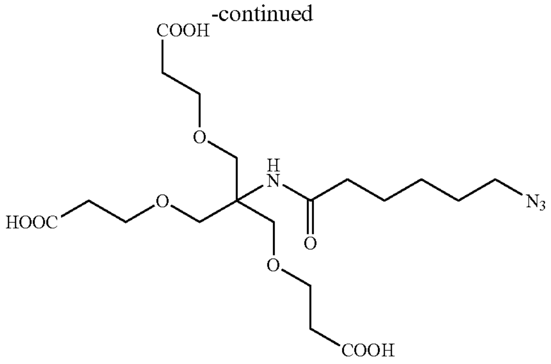

[8]

Synthesis of [7]

HBTU (7.95 g, 7.0 mmol) was added to a mixture of azido hexanoicacid (3.0 g, 19.1 mmol) and compound 6 (8.82 g, 7.0 mmol; synthesis: see, e.g., Biessen, et. al. *J. Med. Chem.* 1999, 42, 609-618) in anhydrous dichloromethane (150 mL) under argon atmosphere at room temperature. DIPEA (13.2 mL, 25.5 mmol) was added in to the reaction mixture slowly and dropwise. Reaction was completed within six hours based on TLC. After the completion of reaction, crude mixture was evaporated off and diluted with ethylacetate (200 mL). Organic layer was washed with water (2×50 mL), brine solution (2×50 mL) and then dried over anhydrous sodium sulphate. Organic layer was further evaporated to dryness and purified via column chromatography (0-100% Ethyl acetate in Pet ether). The product comes at 30-50% ethyl acetate. Pure product 7 (10 g, 94%) was isolated as a colorless liquid and characterized based on NMR and Mass analysis. Results: ESI-MS analysis: Calculated $C_{25}H_{44}N_4O_{10}$. $Na^+$, [M+$Na^+$]=583.30, Observed=583.30.

Synthesis of [8]

See, e.g., Biessen, et. al. *J. Med. Chem.* 1999, 42, 609-618. Compound 7 (3.4 g, 6.07 mmol) was dissolved in a mixture (3:1) of doxane (150 mL) and water (50 mL) at room temperature. Aqueous sodium hydroxide (4M, 12 mL) was added into the reaction mixture and continued overnight at same temperature. Reaction mixture was neutralized and acidified further with excess acetic acid and extracted with ethyl acetate (5×100 mL). Combined organic layer was dried over sodium sulfate and evaporated to dryness to obtain compound 8 (2.2 g, 76%) as a colorless oil. Formation of compound 8 was confirmed based on MS analysis. Results:

ESI-MS analysis: Calculated $C_{19}H_{31}N_4O_{10}$, [M−H]=75.20, Observed=475.10

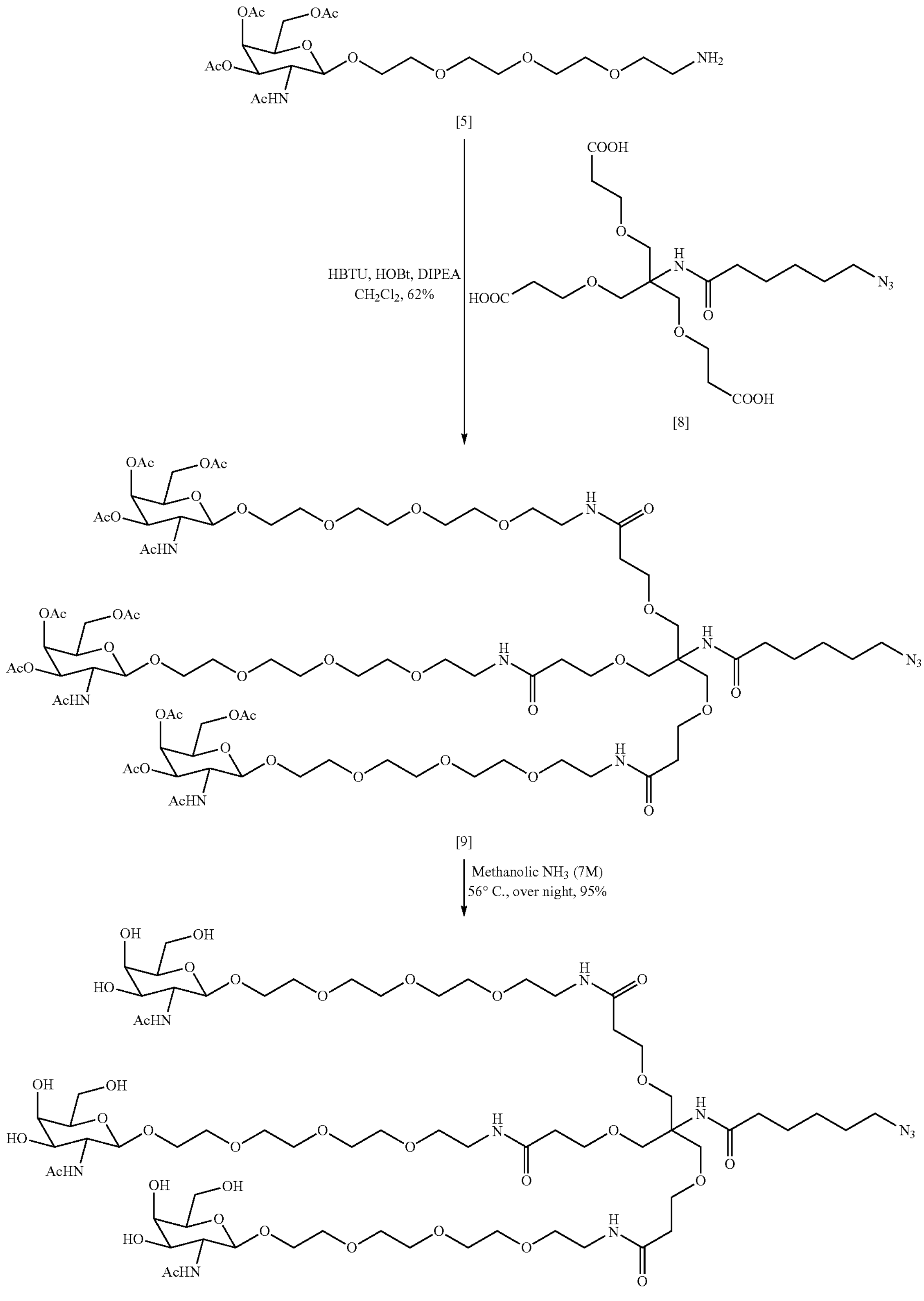
[10]

Synthesis of [9]

See, e.g., Manoharan, et.al. *J. Am. Chem. Soc.* 2014, 136, 16958-16961. To a solution of compound 8 (0.5 g, 1.05 mmol) and 5 (2.74 g, 5.25 mmol) in DMF (30 mL) were added HOBt (0.57 g, 4.20 mmol) and HBTU (1.99 g, 5.25 mmol) followed by slow addition of DIEA (1.83 mL, 10.5 mmol). The reaction was stirred overnight at room temperature and diluted with water. The mixture was extracted with ethyl acetate (2×100 mL). The water phase was separated, extracted with DCM (4×100 mL); and the combined organic layers were washed consecutively with saturated $NaHCO_3$ (2×50 mL), water (2×50 mL), and brine (50 mL). After drying over anhydrous $Na_2SO_4$, the solvent was evaporated under reduced pressure, and the residue was purified by silica gel chromatography (eluent: 10-15% MeOH in DCM) to obtain the compound 9 as a pale yellow foam (1.3 g, 62%). Isolation of pure trivalent GalNAc compound 9 was confirmed based on MS and NMR analysis. Results: ESI-MS analysis: Calculated $C_{85}H_{140}N_{10}O_{43}\cdot Na^+$, $[M+Na^+]$ =2011.89, Observed=2011.60.

Synthesis of [10]

Compound 9 (1.3 g, 0.65 mmol) was dissolved in methanolic ammonia (7M, 50 mL) in a sealed vial and left over night inside the oven at 56° C. Reaction mixture was then evaporated to dryness and washed with ether (3×10 mL) and left on a high vacuum pump to obtain pale yellow sticky solid compound 10 (1.1 g, 95%). Formation of pure compound 10 was confirmed based on mass and NMR analysis. Results: ESI-MS analysis: Calculated $C_{67}H_{122}N_{10}O_{34}$ $Na^+$, $[M+Na^+]$=1633.80, Observed=1633.60. $^1H$ NMR (DMSO-$d_6$): δ 7.91-7.94 (m, 2H), 7.59-7.61 (m, 2H), 7.27 (s, 3H), 6.67 (s, 3H), 4.49-4.60 (m, 7H), 4.26-4.28 (m, 2H), 3.16-3.79 (m, 65H), 2.27-2.30 (m, 3H), 2.06-2.08 (m, 2H), 1.74-1.79 (m, 14H), 1.44-1.52 (m, 2H), 1.22-1.29 (m, 2H).

Synthesis of Trivalent GalNAc Conjugated Oligonucleotides (at the 5'-End of a Fully Phosphothioated Oligonucleotides and Phosphothioated Phosphodiester Compounds (e.g., RN-10486))

MerMade 192X could be used to synthesize various oligonucleotides. Oligonuclotides could be characterized by MS. IEX chromatography, as an orthogonal method, could be used to evaluate purity and also to detect failure sequences.

General Protocol

For a general scheme, see FIG. 1.

5'-alkyne modified fully phosphothioated oligo nucleotides and phosphothioated phosphodiester compounds (e.g., RN-10486) were synthesized using AKTA oligopilot 100 on a 245 μM scale following standard solid phase oligo synthesis protocol. Three oligos were initially synthesized including one control oligo without any $GalNAc_3$-conjugate at the 5'-end. 5-hexyl-1-yl-cyanoethyl amidite was purchased from Glen Research Corporation, USA and was incorporated on to the 5'-end of the oligonucleotides. Oligonucleotides were cleaved from the solid support using 30% aq. ammonium hydroxide (45 mL) at 56° C. overnight inside the oven. Crude oligonucleotide was purified via Hi Prep Q HP 16/10 column [with a solvent gradient 10-100% of eluent B, where, eluent A: 10 mM aq. NaOH and eluent B: aq. NaCl (2.5 M)+NaOH (10 mM)] and then desalted (via Sephadex G25) on an AKTA pure system. Finally, the mass and purity of purified oligonucleotides were identified using Agilent 6130 Quadrupole LC/MS system. 5'-alkyne functionalized oligos were reacted with Trivalent GalNAc azides ($GalNAc_3$—$N_3$; e.g., compound 10) following click reaction conditions. See, e.g., Manoharan, et.al. *Org. let.* 2010, 12, 5410-5413; Manoharan, et.al. *ACS Chem. Biol.* 2015, 10, 1181-1187. Finally, trivalent GalNAc-conjugated oligos were purified, desalted using AKTA pure system and characterized by LCMS analysis. Following are the example of 5'-$GalNAc_3$-conjugated RaNA oligonucleotides (Table 1).

TABLE 1

Exemplary GalNAc-conjugated and non-conjugated oligonucleotides

| Oligo | Sequence (5'-3') | Expected [M + H] | Observed [M + H] |
|---|---|---|---|
| RN-02999 | lnamCs dCs lnaAs dTs dTs lnaGs lnaTs dCs dAs lnamCs dAs lnamCs dTs lnamCs lnamCs (SEQ ID NO: 7) | 4967 | 4967 |
| RN-10485 | GalNAc(PS) dAo dAo lnamCs dCs lnaAs dTs dTs lnaGs lnaTs dCs dAs lnamCs dAs lnamCs dTs lnamCs lnamCs (SEQ ID NO: 8) | 7381 | 7381 |
| RN-10486 | GalNAc(PO) dAo dAo lnamCs dCs lnaAs dTs dTs lnaGs lnaTs dCs dAs lnamCs dAs lnamCs dTs lnamCs lnamCs (SEQ ID NO: 9) | 7365 | 7365 |
| RN-11028 | GalNAc(PS) dARp dARp lnamCs dCs lnaAs dTs dTs lnaGs lnaTs dCs dAs lnamCs dAs lnamCs dTs lnamCs lnamCs (SEQ ID NO: 10) | 7413 | 7413 |
| RN-11029 | GalNAc(PS) dASp dASp lnamCs dCs lnaAs dTs dTs lnaGs lnaTs dCs dAs lnamCs dAs lnamCs dTs lnamCs lnamCs (SEQ ID NO: 11) | 7413 | 7413 |
| RN-11507 | GalNAc(PS) dAo dAo lnamCs lnaAs lnaAs dGs dAs dTs dCs dCs dAs dAs dAs dGs lnamCs lnamCs lnaTs (SEQ ID NO: 12)a | 7379 | 7379 |

o = phosphodiester,
s = phosphorothioate,
lna = locked nucleic acid,
d = DNA,
Rp = phosphorothioate linkage with R stereochemistry at that linkage and
Rs = phosphorothioate linkage with S stereochemistry at that linkage,
m = 5-methyl Synthesis of RN-10485 and RN-10486

RN-10485

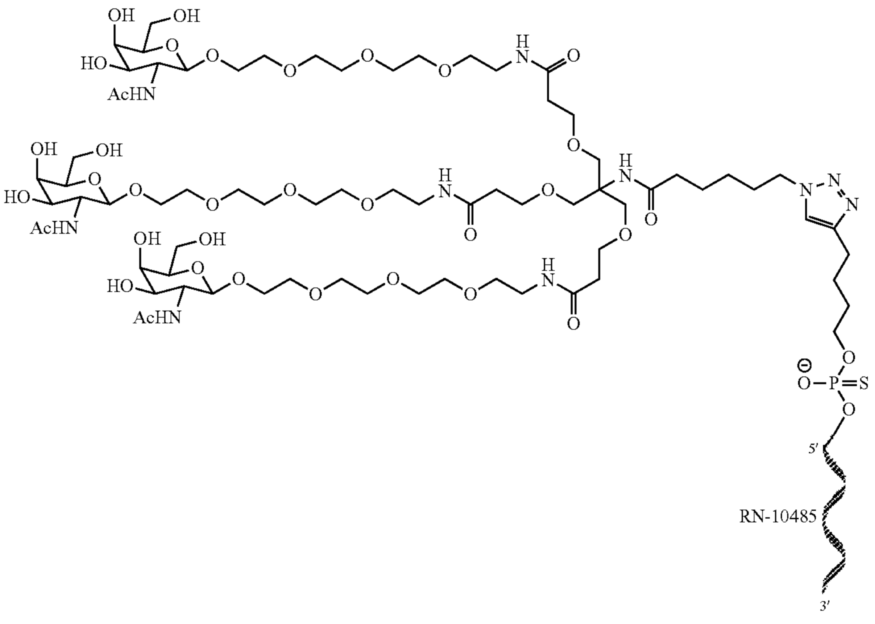

RN-10486

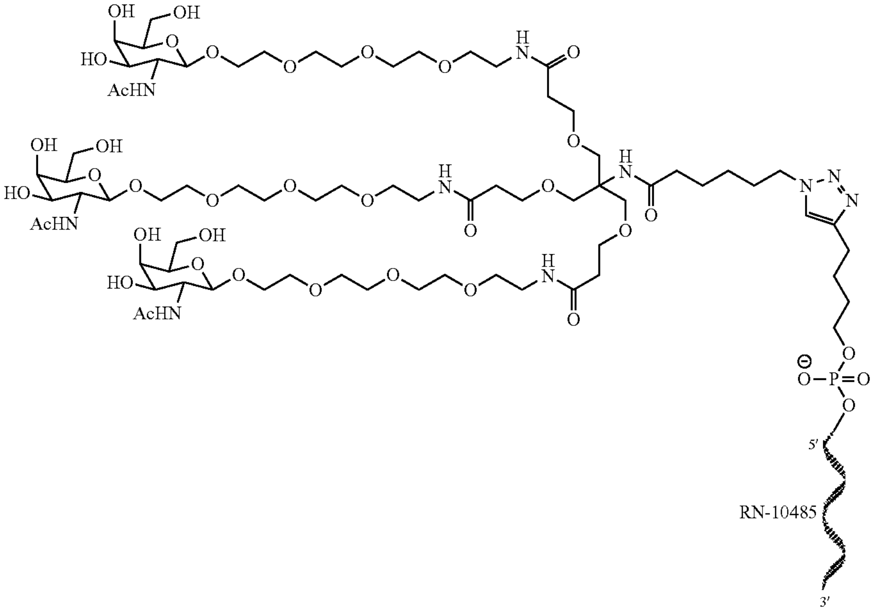

RN-10485 was synthesized in a manner similar to the general protocol described above. The corresponding 5'-alkyne modified oligo (4 mM) was reacted with compound 10 (50 mM) in the presence of 0.1 M CuBr, 0.1 M THBTA in DMSO/BuOH (3:1) at 80° C. for 45 min and then at room temperature for 12 h. Complete conversion was observed. Crude reaction mixture was precipitated from cold ethanol (loosing oligo). It was then dissolved in 2 mL of 0.5 M EDTA (pH 8.0) and vortexed. It was passed through NAP column, purified on AKTA Pure (Hi Prep Q HP, 16/10), desalted on a Shephadex G25 column, and was placed on lyophilizer for 3-4 days.

RN-10486 was synthesized in the manner similar to RN-10485.

In Vivo and In Vitro Experiments

In Vivo Assessment of GalNAc-Conjugated Compound RN-10485

RN-02999 is a well characterized LNA/DNA oligo that has been tested in Phase II trials for the treatment of HCV. RN-02999 targets miR-122, a hepatocyte-specific miRNA. Inhibition of miR-122 by RN-02999 is expected to result in de-repression/upregulation of miR-122 target genes, e.g. AldoA and CD320, as well as downstream cholesterol lowering effects. GalNAc conjugation of RN-02999 was used to assess the activity profile of GalNAc-linker chemistry both in vitro and in vivo. The linker cleavability was also assessed in vivo.

Male C57BL6 (8 wks) mice were used; compounds were dosed at 0.3, 1, 3, and 10 mg/kg. PBS was used for comparison. Single subcutaneous administration was performed. Study was terminated at day 7.

Figure 2:
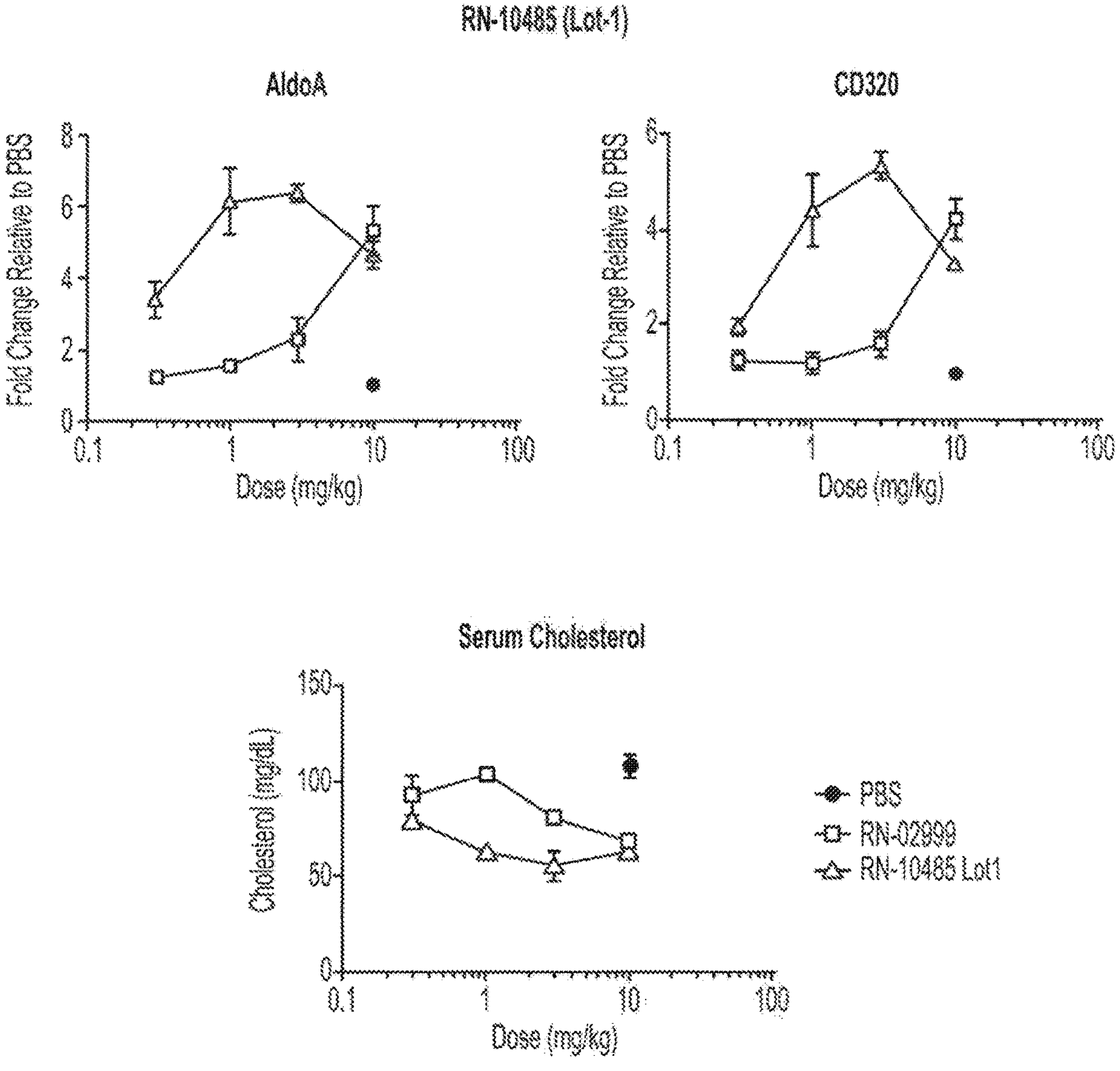
FIG. 2 exemplifies RN-10485 in vivo activity as compared to RN-02999.
Figure 3:
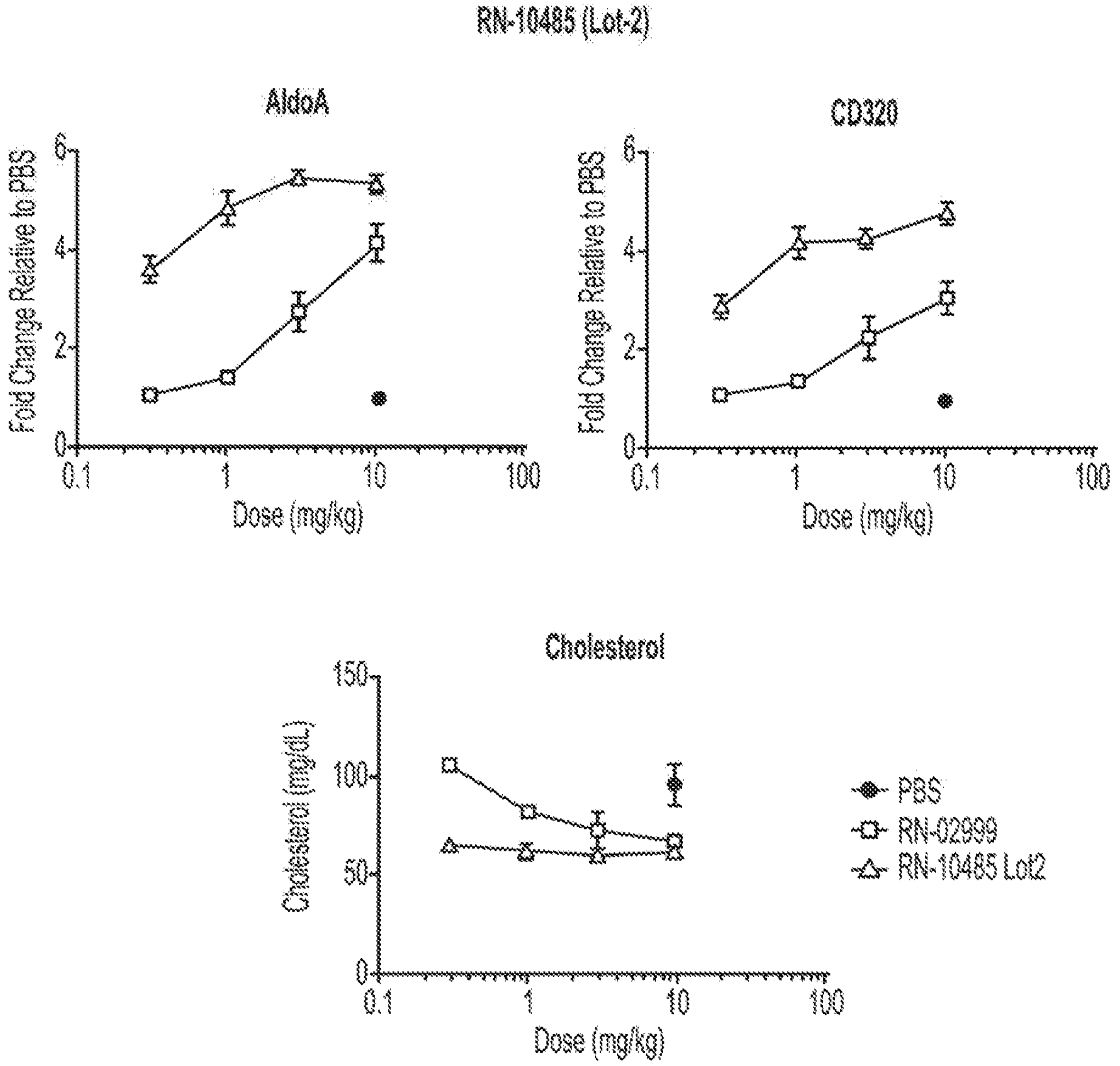
FIG. 3 exemplifies RN-10485 in vivo activity as compared to RN-02999.
Figure 4:
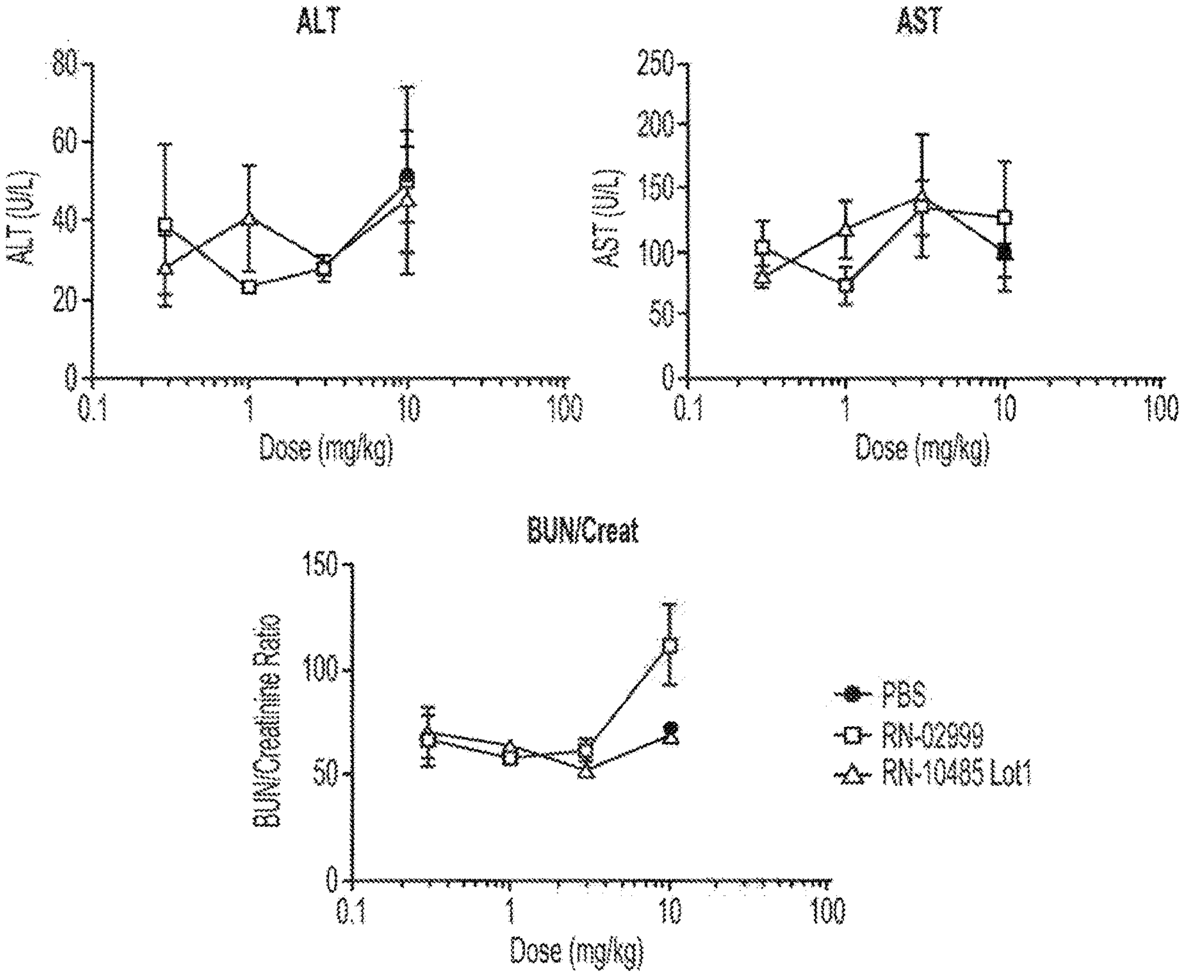
FIG. 4 exemplifies no elevation of liver and kidney injury markers for RN-10485 in in vivo experiments.

The results are shown in FIGS. 2-4. GalNAc-conjugation of RN-02999 resulted in significant enhancement in vivo activity (see FIGS. 2 and 3). Robust upregulation of liver mRNA targets AldoA and CD320 and reduced serum cholesterol levels (downstream biomarker) were observed. ~10-fold enhanced potency was observed with GalNAc-conjugated compound in liver mRNA and serum PD markers. No elevation of liver and kidney injury markers was observed (see FIG. 4). Based on the data, in vivo toxicity is not expected at these dose levels.

In Vivo PK/PD Assessment of GalNAc-Conjugated Compound RN-10485

PK Assay (Quantitation): GalNAc Conjugate RN-10485 and its parent 15-mer RN-02999 were analyzed in mouse kidney and liver samples from a prior study.

Figure 5:
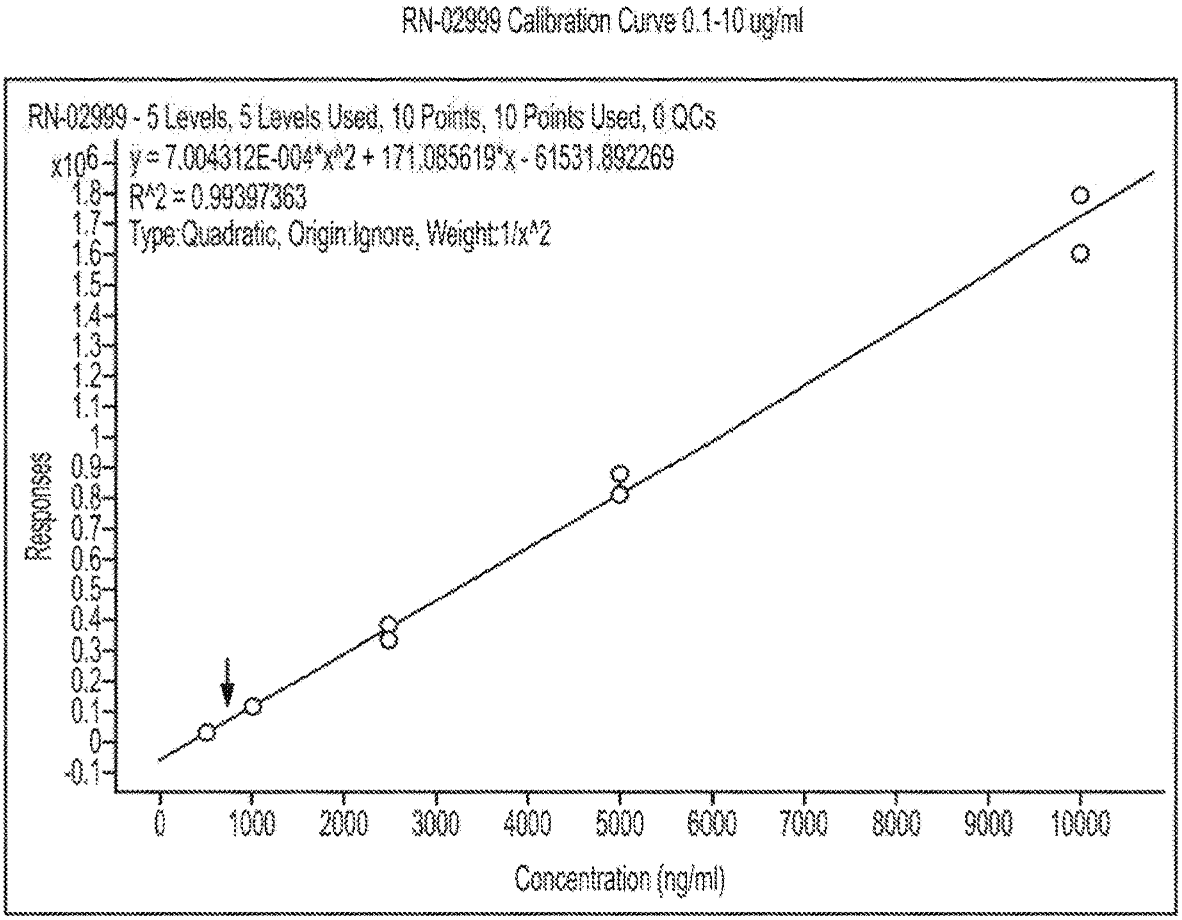
FIG. 5 exemplifies calibration curve of RN-02999 in mouse kidney tissue samples.

Calibration curve of RN-02999 in mouse kidney tissue samples was established. See FIG. 5. Mouse kidney and liver samples were then analyzed. See Table 2. Conjugate RN-10485 showed improved liver tissue uptake of oligo RN-02999 between 5 to 26 folds. Low dose level improved more than high dose level (high level potential uptake saturation).

TABLE 2

R-02999 concentration summary in mouse kidney and liver samples

| Test compound | Dose mg/kg | Dose Route | Mean Kidney Conc (ug/g) | Mean Liver Conc (ug/g) | Kidney/Liver ratio |
|---|---|---|---|---|---|
| RN-02999 | 0.3 | SC | 5.14 | 0.195 | 26 |
| | 1.0 | SC | 9.29 | 0.573 | 16 |
| | 3.0 | SC | 19.4 | 1.53 | 13 |
| | 10.0 | SC | 65.8 | 5.91 | 11 |
| RN-10485 | 0.45 | SC | 0 | 1.08 | ND (1 ug/kg detected in liver-none in kidney) |
| | 1.5 | SC | 0 | 4.13 | ND (4 ug/kg detected in liver-none in kidney) |
| | 4.5 | SC | 11.2 | 7.46 | 1.5 |
| | 14.5 | SC | 32.3 | 14.1 | 2.3 |

Figure 6:
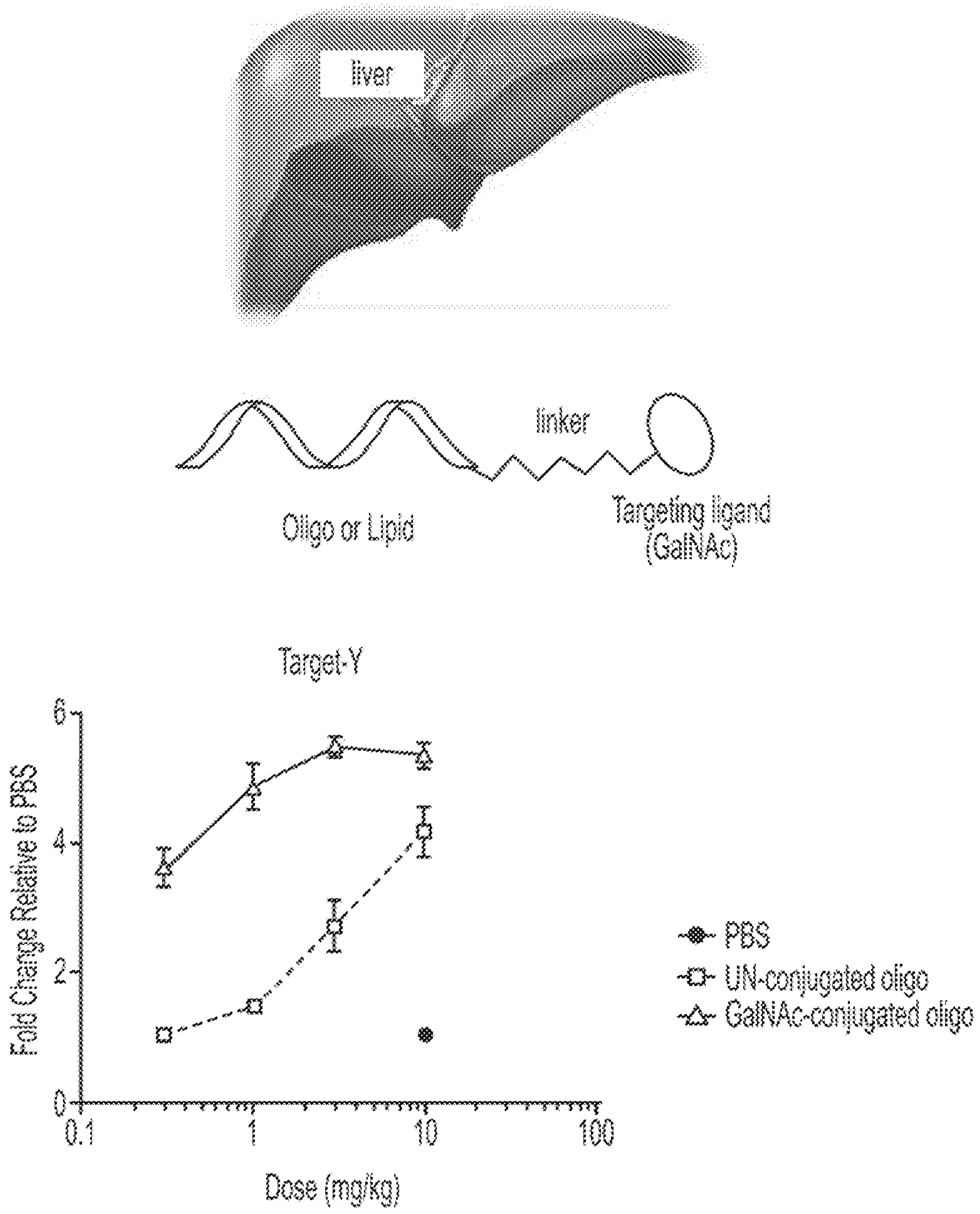
FIG. 6 exemplifies RN-10485 in vivo activity as compared to RN-02999.

The results showed that conjugation to $GalNAc_3$ moiety enhances in vivo potency 15-20 fold in mouse liver and reduces oligo exposure in kidney (see FIG. 6 and Table 2).

In Vivo Assessment of GalNAc-Conjugated Compound RN-11507

Figure 7:
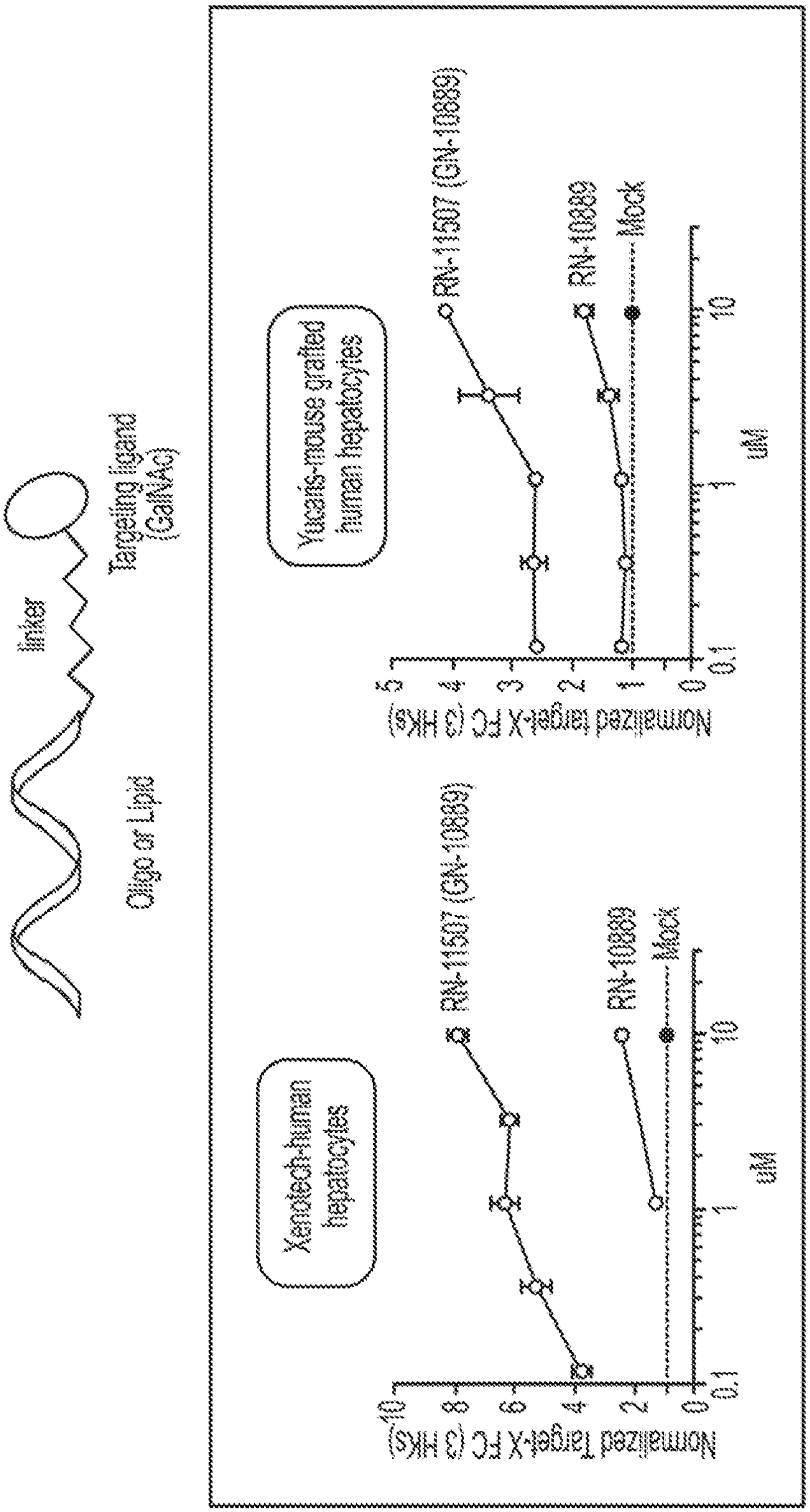
FIG. 7 exemplifies conjugation potency enhancement applicability to other liver disease targets.

RN-11507 was tested in a mouse model (see FIG. 7). The results showed that potency enhancement is broadly applicable to other liver disease targets. Excellent enhancement in target X mRNA upregulation in primary hepatocytes with GalNAc conjugated oligo.

Chiral Phosphorothioate Linked $GalNAc_3$-Conjugated Oligonucleotides for the Liver Target Properties Exemplary chiral phosphorothioates and the expected cleavage patterns are shown in FIG. 8. Individual phosphorotioate stereoisomers possess differential biophysical and biological properties. Rp isomer: higher $T_m$ and lower exonuclease stability. Sp isomer: lower $T_m$ and higher exonuclease stability.

Synthesis of Chiral Phosporothioates

Chiral phosphorotioates can be synthesized using Sp-oxazaphospholidine and Rp-oxazaphospholidine building blocks.

Sp-oxazaphospholidine building block $A^{Bz}$ ($A^{Bz}$(Sp)) was synthesized according to the following procedure (see *J. Org. Chem,* 2003, 68, 9747-9752).

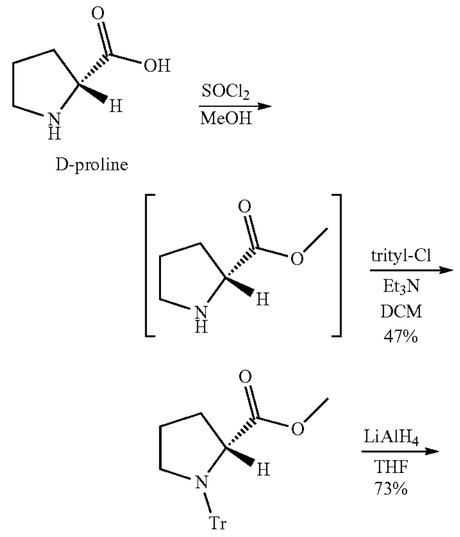

D-proline

-continued

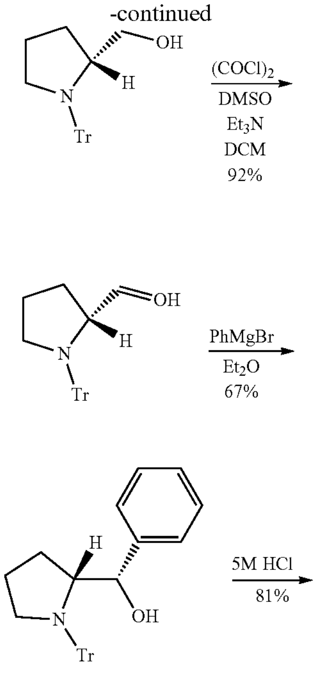

-continued
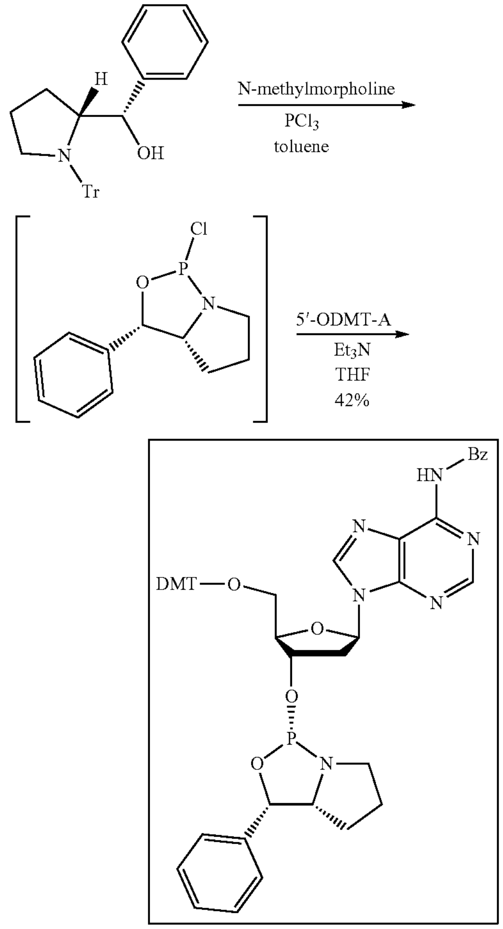
Sp-oxazaphospholidine
($A^{Bz}$)
4.2 g isolated
Rp-oxazaphospholidine building block $A^{Bz}$ ($A^{Bz}$(Rp)) can be synthesized according to the following procedure (see J. Org. Chem, 2003, 68, 9747-9752 and Nucleic Acids Research, 2014, 42(22), 13456-13458).
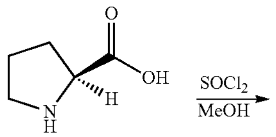
L-proline
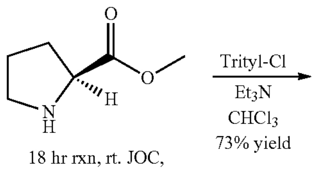
18 hr rxn, rt. JOC, 2003, 68, 9747-9752
-continued
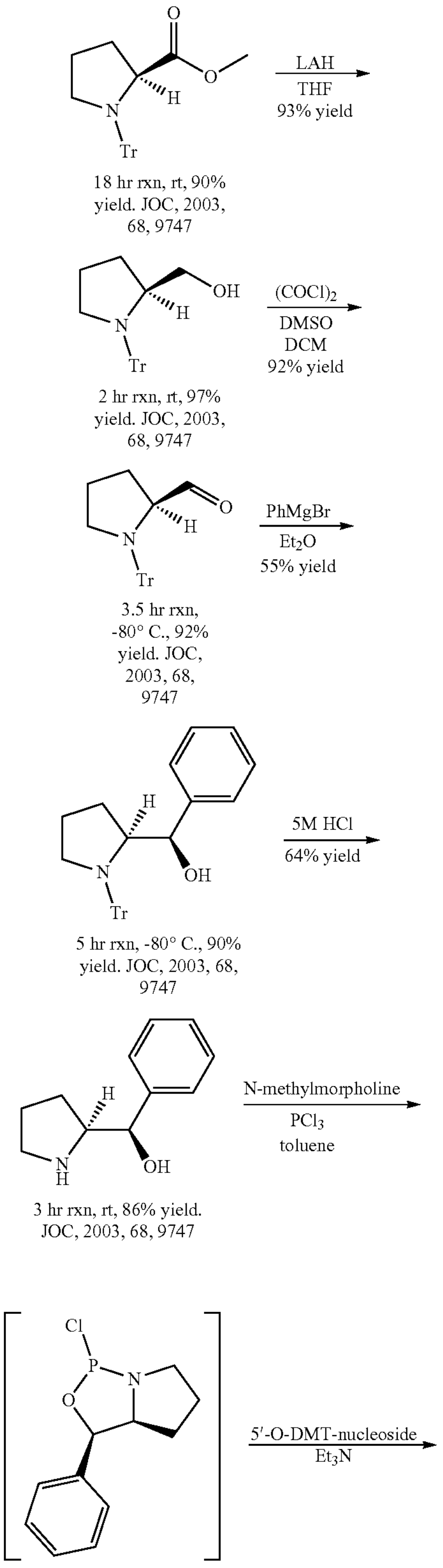
2.5 hr rxn, -70° C., 86-95% yields. Nucleic Acids Research, 42(22), 13456-13468, 2014

-continued
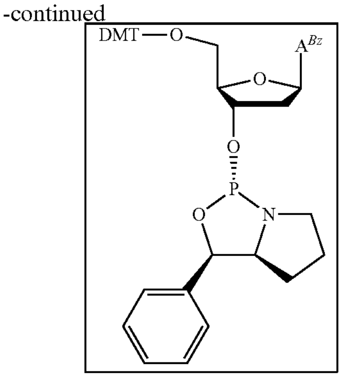
Mannose conjugated oligos can enhance the functional delivery to variety of cells of therapeutic interest. Mannose Receptor (MR) is a carbohydrate-binding receptor expressed by selected populations of macrophages and dendritic cells (DCs) and nonvascular endothelium.
The following compound can be evaluated for its biological activity.

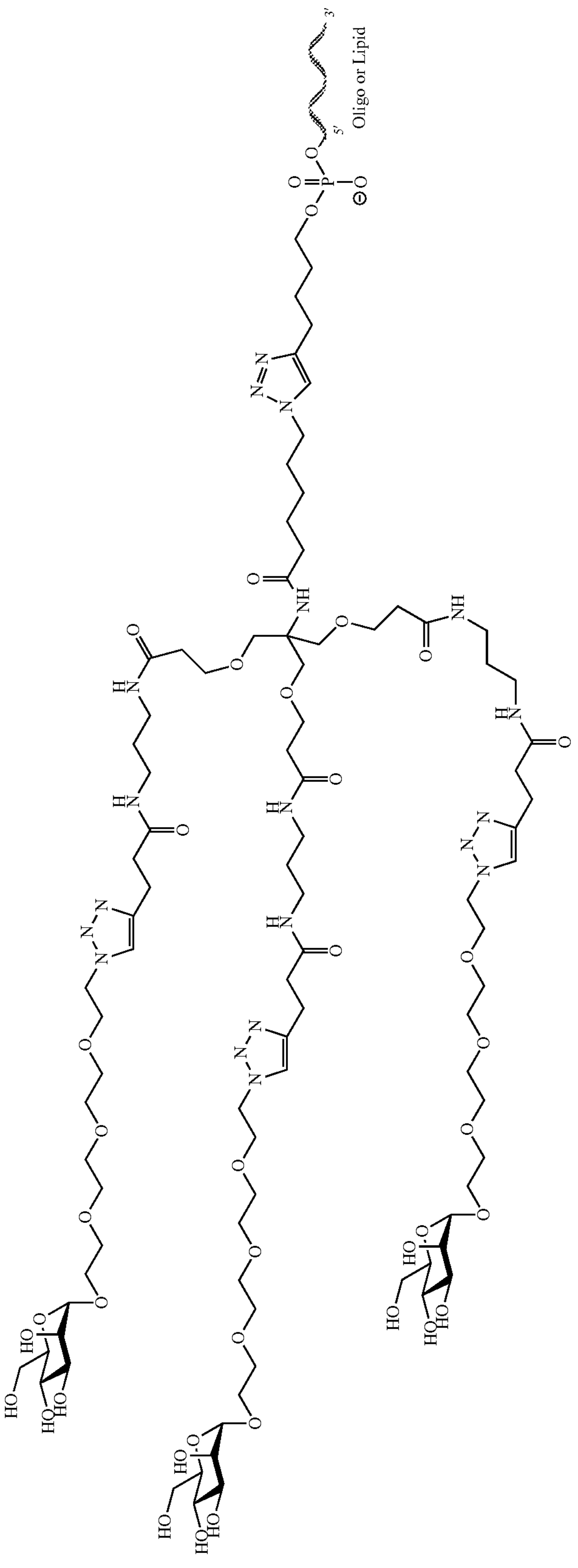

The compound can be synthesized via click chemistry conjugation approach similar to the one described for GalNAc conjugates above.

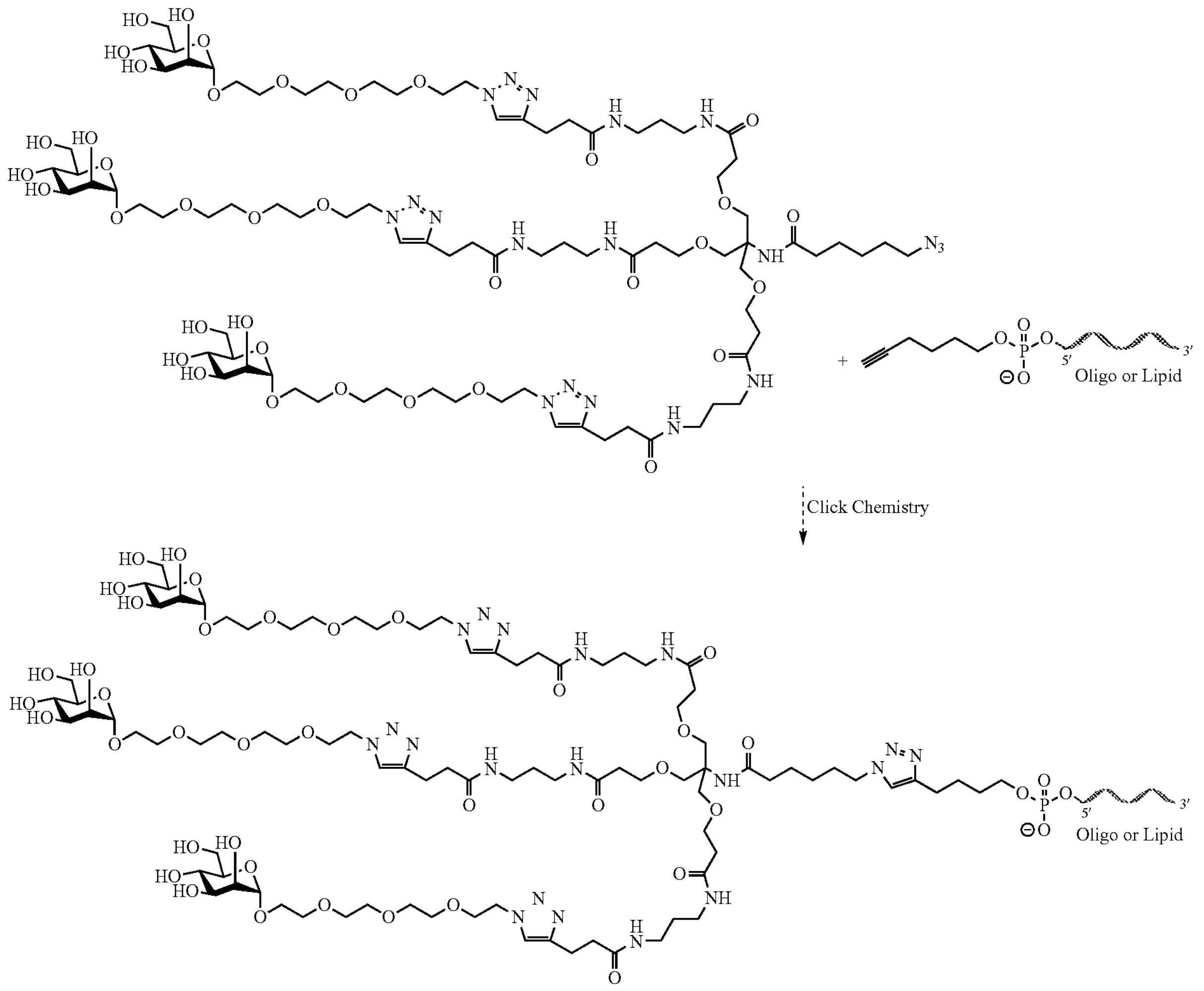

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A conjugate of Formula (I):

(I)

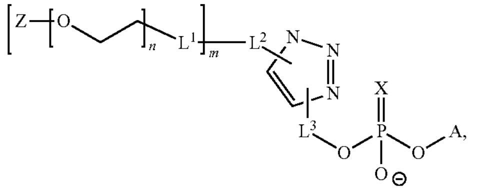

or a pharmaceutically acceptable salt thereof, wherein:

A is a nucleic acid;

X is O or S;

each Z independently is a sugar, a folate, or a cell-penetrating peptide;

each of $L^2$ and $L^3$ is independently a bond, optionally substituted alkylene, or optionally substituted heteroalkylene;

wherein each $L^1$ comprises a triazole;

m is an integer from 3 to 10, inclusive; and n is an integer from 4 to 10, inclusive.

2. The conjugate of claim 1 having the structure of Formula (II):

(II)

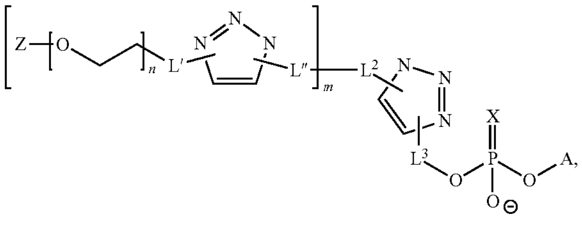

or a pharmaceutically acceptable salt thereof, wherein:

each of L' and L" is independently a bond, optionally substituted alkylene, or optionally substituted heteroalkylene.

3. The conjugate of claim 1, wherein m is 3, each Z independently is a sugar, and the conjugate is of Formula (III):

(III)

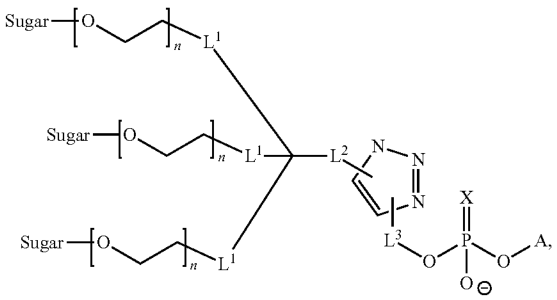

or a pharmaceutically acceptable salt thereof.

4. The conjugate of claim 2, wherein m is 3, each Z independently is a sugar, and the conjugate is of Formula (IV):

(IV)

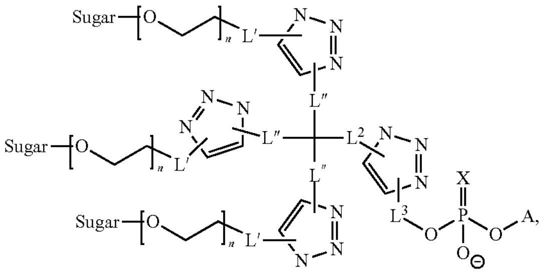

or a pharmaceutically acceptable salt thereof.

5. The conjugate of claim 1, wherein each Z is GalNAc or a derivative thereof or a mannose or a derivative thereof.

6. The conjugate of claim 4, wherein (i) the conjugate is of Formula (IV-a):

(IV-a)

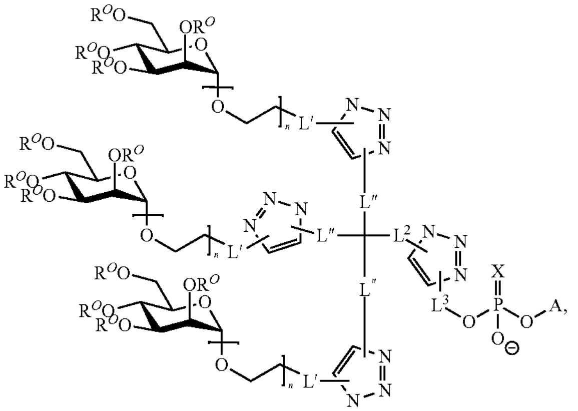

wherein each instance of $R^O$ is independently hydrogen, optionally substituted alkyl, optionally substituted acyl, or an oxygen protecting group (IV-b).

7. The conjugate of claim 1, wherein each instance of $L^1$ is independently optionally substituted heteroalkylene.

8. The conjugate of claim 1, wherein $L^2$ is optionally substituted heteroalkylene.

9. The conjugate of claim 1, wherein $L^3$ is optionally substituted alkylene.

10. The conjugate of claim 6, wherein each instance of $R^O$ is hydrogen or an oxygen protecting group.

11. The conjugate of claim 1, wherein group A is:

(ii) a single-stranded oligonucleotide;

(iii) a double-stranded oligonucleotide;

(iv) an antisense oligonucleotide; or (v) an mRNA.

12. A pharmaceutical composition comprising a conjugate of claim 1, and a pharmaceutically acceptable carrier or excipient.

13. A method for preparing a conjugate of Formula (I-a):

(I-a)

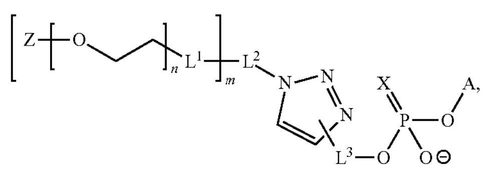

or a pharmaceutically acceptable salt thereof, wherein:

A is a group comprising a nucleic acid;

X is O or S;

Z is a sugar, a folate, or a cell-penetrating peptide;

each of $L^2$, and $L^3$ is independently a bond, optionally substituted alkylene, or optionally substituted heteroalkylene;

wherein each $L^1$ comprises a triazole;

m is an integer from 3 to 10, inclusive; and n is an integer from 1 to 10, inclusive;

comprising contacting a compound of Formula (I-a-Az):

(I-a-Az)

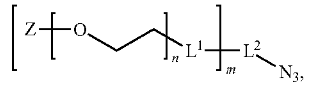

or a salt thereof, with a compound of Formula (I-a-Alk):

(I-a-Alk)

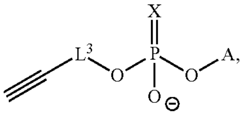

under conditions suitable to yield the conjugate of Formula (I-a).

14. A method for preparing a conjugate of Formula (I-h):

(I-h)

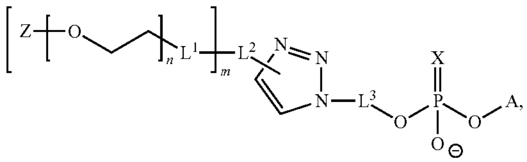

or a pharmaceutically acceptable salt thereof, wherein:

A is a group comprising a nucleic acid;

X is O or S;

Z is a sugar, a folate, or a cell-penetrating peptide;

each of $L^2$, and $L^3$ is independently a bond, optionally substituted alkylene, or optionally substituted heteroalkylene;

wherein each $L^1$ comprises a triazole;

m is an integer from 3 to 10, inclusive; and n is an integer from 1 to 10, inclusive;

comprising contacting a compound of Formula (I-h-Alk):

(I-h-Alk)

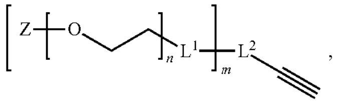

or a salt thereof, with a compound of Formula (I-h-Az):

(I-h-Az)

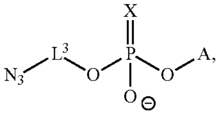

under conditions suitable to yield the conjugate of Formula (I-h).

15. The conjugate of claim 4, wherein the conjugate is of Formula (IV-b):

(IV-b)
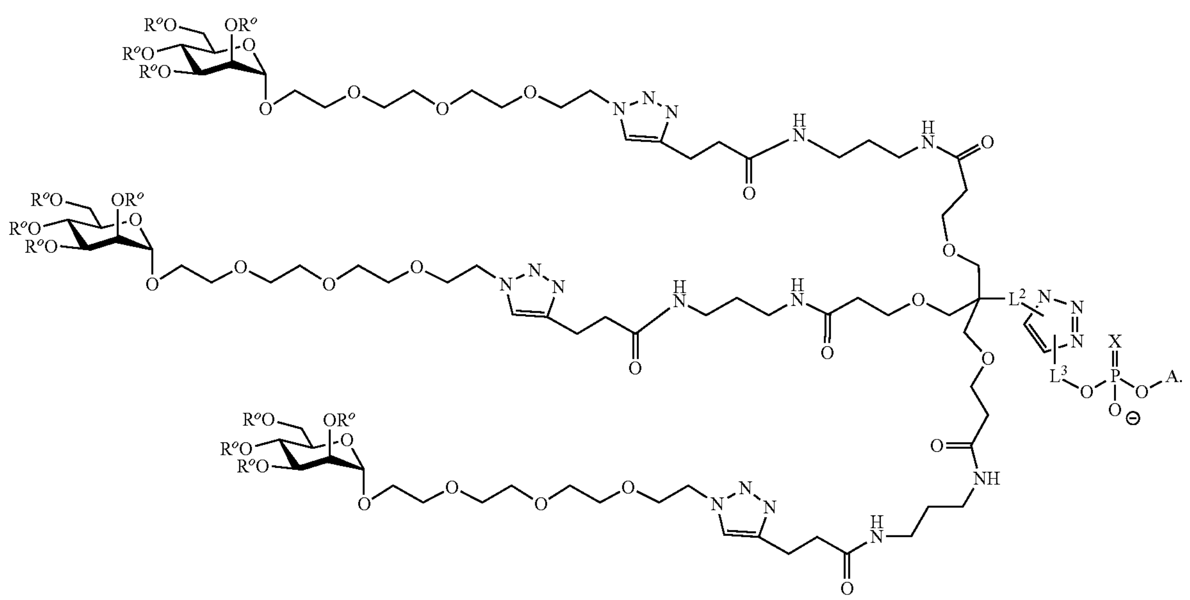
16. The conjugate of claim 4, wherein the conjugate is of Formula (IV-c):

(IV-c)
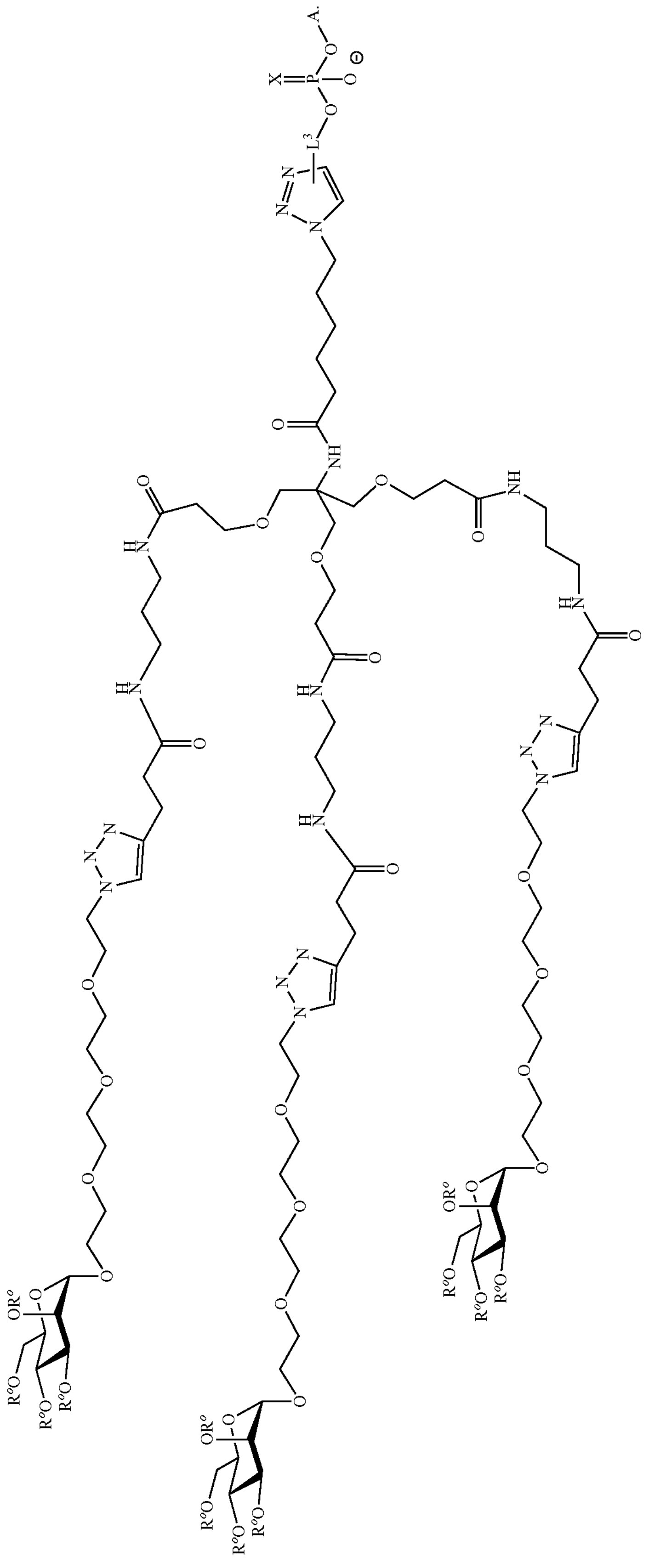

17. The conjugate of claim 4, wherein the conjugate is of Formula (IV-d):

(IV-d)
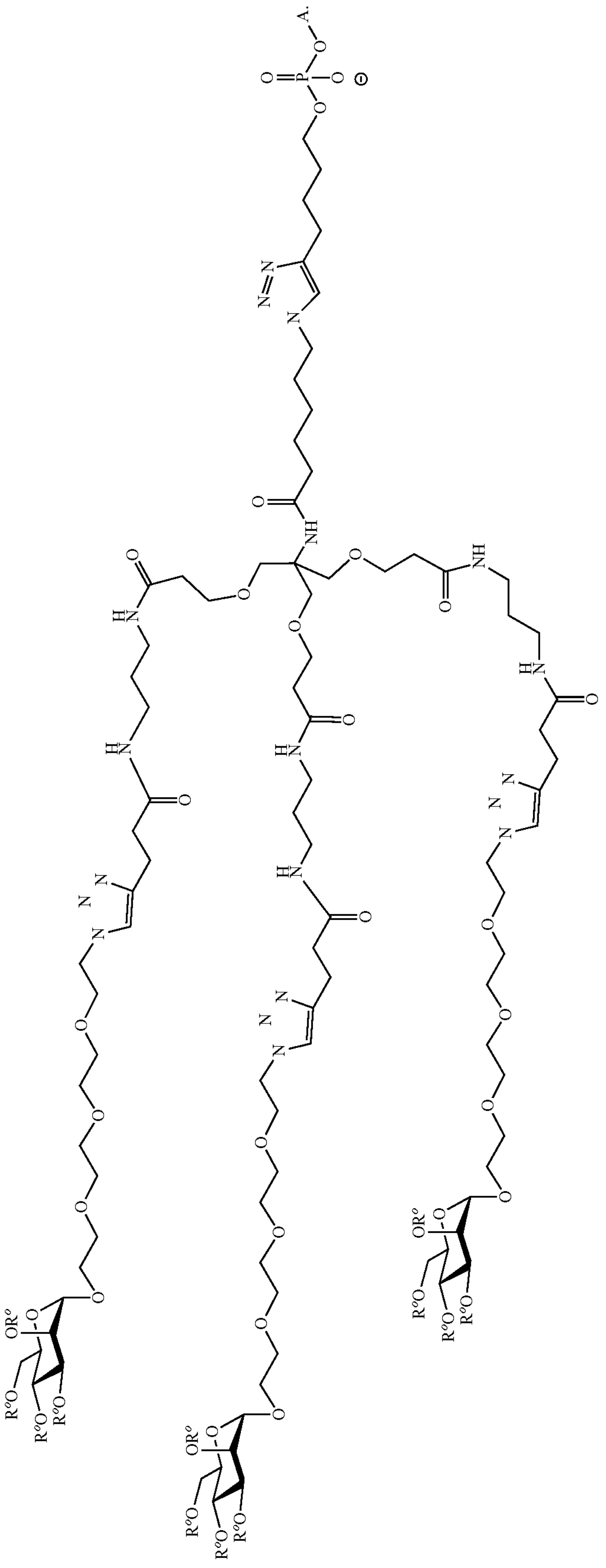

18. The conjugate of claim 4, wherein the conjugate is of Formula (IV-e):

(IV-e)
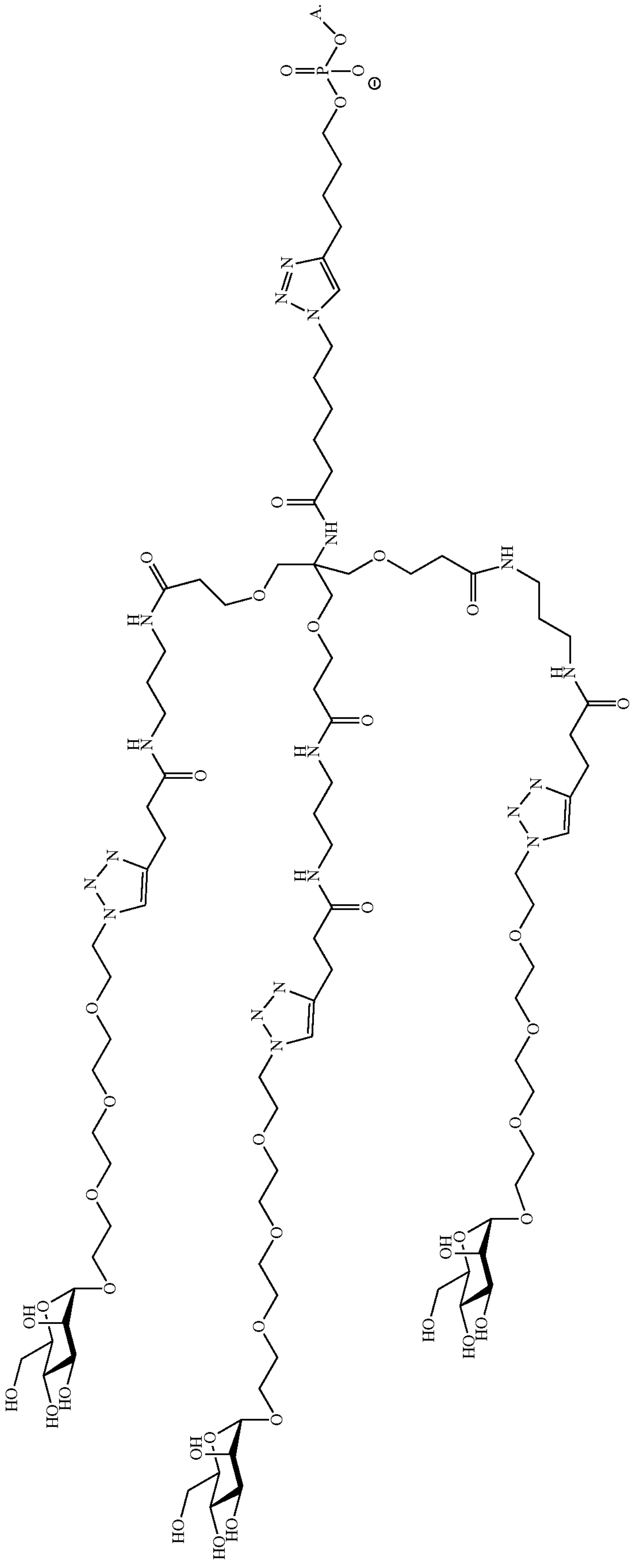
* * * * *